US009555061B2

(12) United States Patent
Shiota et al.

(10) Patent No.: US 9,555,061 B2
(45) Date of Patent: Jan. 31, 2017

(54) SYNTHESIS AND ANALYSIS OF COMPOUNDS CAPABLE OF INDUCING DIFFERENTIATION OF HUMAN MESENCHYMAL STEMS CELLS INTO HEPATOCYTES

(75) Inventors: Goshi Shiota, Yonago (JP); Yoshiko Hoshikawa, Yonago (JP); Noriko Matsumoto, Yonago (JP); Yoshiaki Matsumi, Yonago (JP); Minoru Morimoto, Tottori (JP); Takayuki Tonoi, Tottori (JP); Hiroyuki Saimoto, Tottori (JP); Kazuo Ohashi, Shinjuku-ku (JP); Teruo Okano, Shinjuku-ku (JP)

(73) Assignees: National University Corporation Torrori University, Tottori-shi (JP); Tokyo Women's Medical University, Shinjuku-ku, Tokyo (JP)

( * ) Notice: Subject to any disclaimer, the term of this patent is extended or adjusted under 35 U.S.C. 154(b) by 408 days.

(21) Appl. No.: 14/111,757

(22) PCT Filed: Apr. 2, 2012

(86) PCT No.: PCT/JP2012/059021
§ 371 (c)(1),
(2), (4) Date: Dec. 31, 2013

(87) PCT Pub. No.: WO2012/141038
PCT Pub. Date: Oct. 18, 2012

(65) Prior Publication Data
US 2014/0112892 A1 Apr. 24, 2014

(30) Foreign Application Priority Data
Apr. 15, 2011 (JP) ................................. 2011-091599

(51) Int. Cl.
| *A01N 63/00* | (2006.01) |
| *A61K 35/407* | (2015.01) |
| *C07C 251/86* | (2006.01) |
| *C07C 43/225* | (2006.01) |
| *C07D 487/04* | (2006.01) |
| *C07D 307/52* | (2006.01) |
| *A61L 27/38* | (2006.01) |

(52) U.S. Cl.
CPC .......... *A61K 35/407* (2013.01); *A61L 27/3804* (2013.01); *A61L 27/3834* (2013.01); *C07C 43/225* (2013.01); *C07C 251/86* (2013.01); *C07D 307/52* (2013.01); *C07D 487/04* (2013.01); *A61L 2430/28* (2013.01)

(58) Field of Classification Search
CPC .............. A61L 35/407; A61L 27/3804; A61L 27/3834; A61L 2430/28; C07C 42/224; C07C 251/186; C07D 307/62; C07D 487/04
See application file for complete search history.

(56) References Cited

U.S. PATENT DOCUMENTS 5,610,192 A * 3/1997 Cohen ................... A61K 31/135
514/614
2005/0059628 A1 3/2005 Kahn
2007/0249045 A1 10/2007 Gimble
2008/0269206 A1 10/2008 Russell
2009/0215783 A1 8/2009 Oh

FOREIGN PATENT DOCUMENTS

| JP | 2007-503816 A | 3/2007 |
| JP | 2009-538903 A | 11/2008 |
| JP | 2009-535035 A | 10/2009 |
| JP | 2010-075631 A | 4/2010 |
| JP | 2010-523579 A | 7/2010 |
| JP | 2011-219435 A | 11/2011 |
| WO | WO 87/16127 A1 * | 4/1987 |
| WO | 2007/139346 A1 | 12/2007 |

OTHER PUBLICATIONS

Himmel et al. Chemical Biology (2006) 1(11); 702-712.*
Supplementary Partial European Search Report mailed Dec. 11, 2014, issued in corresponding European Patent Application No. EP 12 77 1389, filed Apr. 2, 2012, 9 pages.
McMillan, M., and M. Kahn, "Investigating Wnt Signaling: A Chemogenomic Safari," Drug Discovery Today 10(21):1467-1474, Nov. 2005.
Piergentili, A., et al., "Solution-Phase Synthesis of ICG-001, a β-Turn Peptidomimetic Molecule Inhibitor of β-Catenin-Tcf-Mediated Transcription," Tetrahedron 63(52):12912-12916, Dec. 2007.
Japanese First Office Action, mailed Jan. 5, 2016, issued in corresponding Japanese Application No. 2013-509857, filed Oct. 11, 2013, 12 pages.
Shiota, G., "Present and Future Views of Hepatic Regenerative Medicine Using Human Mesenchymal Stem Cells," Regenerative Medicine 8(1):95-103, Color Gravure pp. 12-14, 2009.
Emami, K.H., et al., "A Small Molecule Inhibitor of β-Catenin/CREB-Binding Protein Transcription," Proceedings of the National Academy of Sciences of the United States of America (PNAS) 101(34):12682-12687, Aug. 2004.
Ishii, K., et al., "Hepatic Differentiation of Human Bone Marrow-Derived Mesenchymal Stem Cells by Tetracycline-Regulated Hepatocyte Nuclear Factor 3β," Hepatology 48(2):597-606, Aug. 2008.
Lepourcelet, M., et al., "Small-Molecule Antagonists of the Oncogenic Tcf/β-Catenin Protein Complex," Cancer Cell 5(1):91-102, Jan. 2004.

(Continued)

*Primary Examiner* — Susan Hanley
(74) *Attorney, Agent, or Firm* — Christensen O'Connor Johnson Kindness PLLC

(57) ABSTRACT

The invention relates to low-molecular-weight compounds which are capable of inducing differentiation of mesenchymal stem cell into hepatocytes.

13 Claims, 23 Drawing Sheets

(56) References Cited

OTHER PUBLICATIONS

Matsumi, Y. et al., "Hito Kotsuzui Yurai Kan'yo-kei Kansaibo o Kinosei Kansaibo e Bunka Yudo Sayo o Motsu Wnt/β-Catenin Signal Yokuseisei Teibunshi Kagobutsu no Dotei ni yoru Kan Saisei Iryo Kaihatsu (The Liver Regenerative Medicine Development Through Identification of Wnt/β-Catenin Signaling Inhibitory Low-Molecular-Weight Compounds With Differentiation-Inducing Activity Into Functional Liver Cells Derived From Human Bone Marrow Mesenchymal Stem Cells)," Acta Hepatologica Japonica 51(Suppl. 1):A259-A260, Apr. 2010.

Park, S., et al., "Hexachlorophene Inhibits Wnt/β-Catenin Pathway by Promoting Siah-Mediated β-Catenin Degradation," Molecular Pharmacology 70(3):960-966, Sep. 2006.

Shan, J., et al., "Identification of a Specific Inhibitor of the Dishevelled PDZ Domain," Biochemistry 44(47):15495-15503, Nov. 2005.

Shimomura, T., et al., "Hepatic Differentiation of Human Bone Marrow-Derived UE7T-13 Cells: Effects of Cytokines and CCN Family Gene Expression," Hepatology Research 37(12):1068-1079, Dec. 2007.

Trosset, J.Y., et al., "Inhibition of Protein—Protein Interactions: The Discovery of Druglike β-Catenin Inhibitors by Combining Virtual and Biophysical Screening," Proteins: Structures, Function, and Bioinformatics 64(1):60-67, Jul. 2006.

Yanagitani, A., et al., "Retinoic Acid Receptor Dominant Negative Form Causes Steatohepatitis and Liver Tumors in Transgenic Mice," Hepatology 40(2):366-375, Aug. 2004.

Yoshida, Y., et al., "A Role of Wnt/β-Catenin Signals in Hepatic Fate Specification of Human Umbilical Cord Blood-Derived Mesenchymal Stem Cells," American Journal Physiology: Gastrointestinal and Liver Physiology 293(5):G1089-G1098, Nov. 2007.

International Search Report mailed Jun. 26, 2012, in corresponding PCT/JP2012/059021, filed Mar. 22, 2012, 4 pages.

\* cited by examiner mp 94-96 °C
IR (KBr): 3366, 3361, 3028, 2924, 1647, 1539, 1489, 1464, 1412, 1362, 1294, 1258, 1217, 1193, 1030, 758, 738, 700 cm$^{-1}$.
MS (EI): m/z (%) = 532; Exact mass: 532.35
$^1$H NMR (400 MHz, DMSO-d$_6$) δ = 2.06 (m, 2H), 3.11-3.40 (m, 5H), 3.59 (t, J = 11 Hz, 1H), 3.86 (m, 1H), 4.19 (qt, J = 5, 15 Hz, 1H), 4.32 (dd, J = 5, 15 Hz, 1H), 4.93 (d, J = 15 Hz, 1H), 5.14 (d, J = 15 Hz, 1H), 5.22 (m, 1H), 5.77 (dd, J = 4, 11 Hz, 1H), 7.14-8.16 (m, 17H).

IC-2

(6S,9aS)-6-phenyl-8-naphthalen-1-ylmethyl-4,7-dioxo-hexahydro-pyrazino[1,2-a]pyrimidine-1-carbocylic acid benzylamide

HC-1 hexachlorophene methyl ether
bis(2,3,5-trichloro-6-methoxyphenyl)methane

PN-3-4

N'-[(E)-1-naphtylmethylidene]-2-phenoxybenzohydrazide

PN-3-13

N'-[(E)-pentafluoropheylmethylidene]-2-phenoxybenzohydrazide

FIG. 10
Hepatic differentiation (RT-PCR)
PN-1-2 / PN-3-4 / PN-3-13
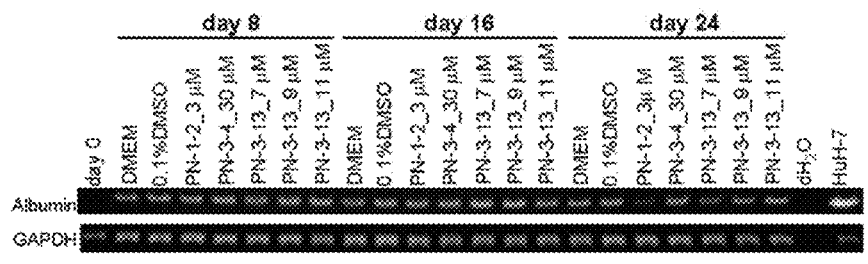
HC-1 / IC-2
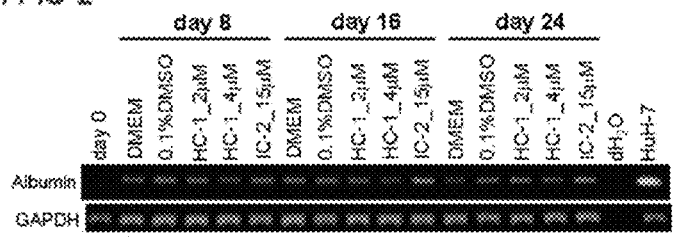
FIG. 11
Comparison with original compounds (RT-PCR)
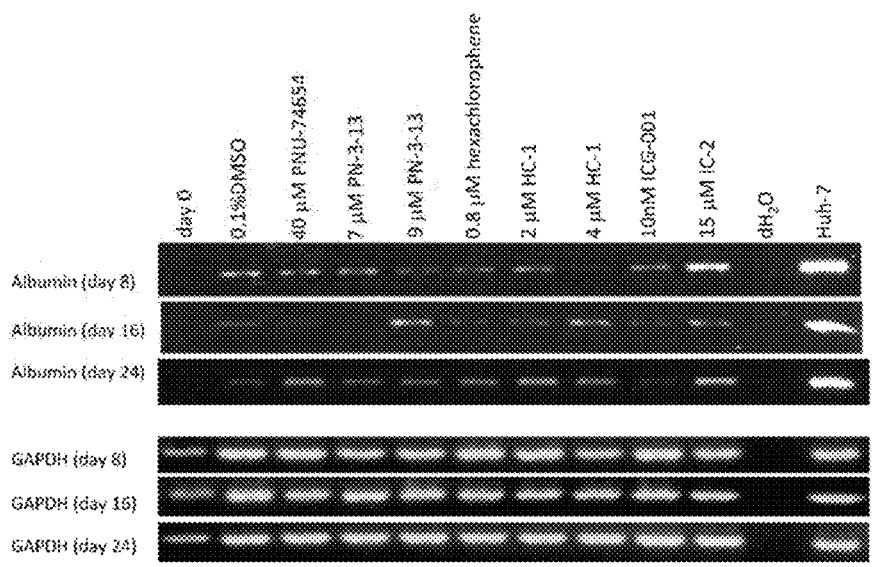

Gene Expression of Liver-specific Secretory Proteins and Cytokines When Hexachlorophene or IC-2 Was Used to Induce Differentiation into Hepatocytes Neovascularization Effect of bFGF-containing Device

FIG. 18

Transplantation of Cell Sheet under Skin of Mouse with Acute Liver Dysfunction

- animal: NOD-SCID (7-weeks old male mice)
- experimental group:
    - group 1: sham operation (n=8)
    - group 2: 1 layer transplantation (n=8)
    - group 3: 2 layers transplantation (n=8)
    - group 4: 3 layers transplantation (n=8)
- operation: cell sheets transplanted into <u>one site of neovascularized subcutaneous space on the back</u>

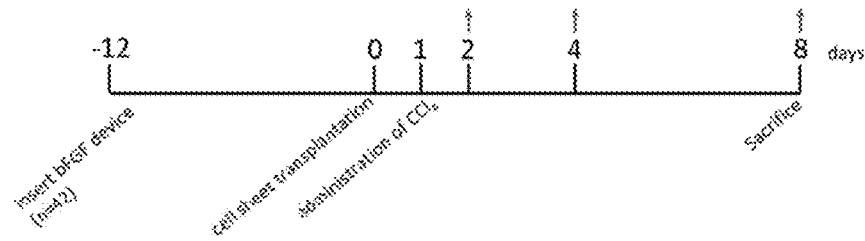

FIG. 19

How Liver Functions Changed When Cell Sheet Was Transplanted under Skin of Mouse with Acute Liver Dysfunction

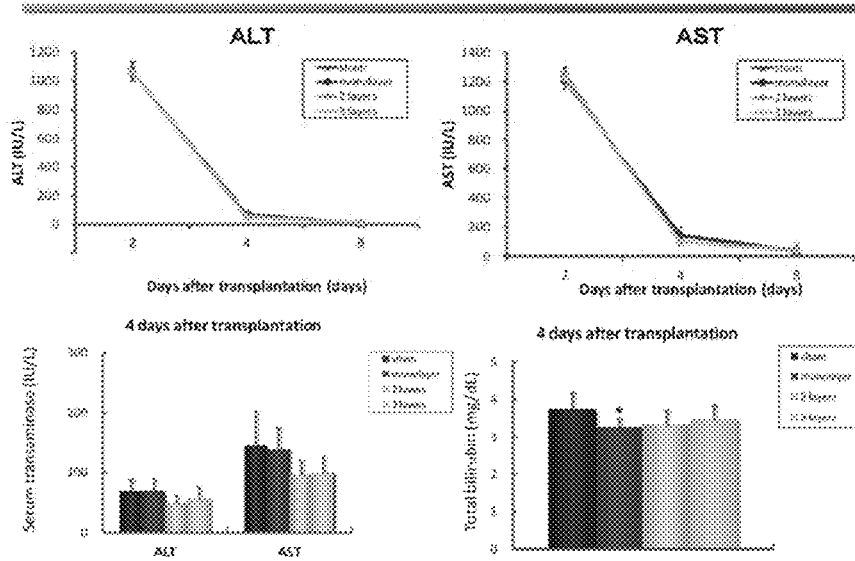

FIG. 20

Images of Hexachlorophene-induced Cell Sheet Transplanted on Liver Surface

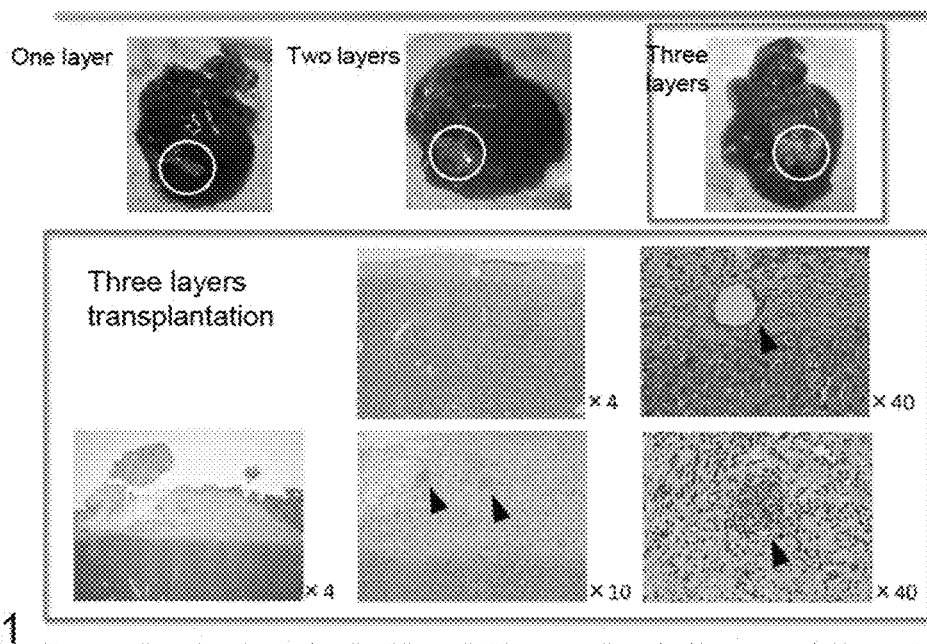

FIG. 21

Examination of Cell Sheet Transplantation on Liver Surface of Mouse with Acute Liver Dysfunction

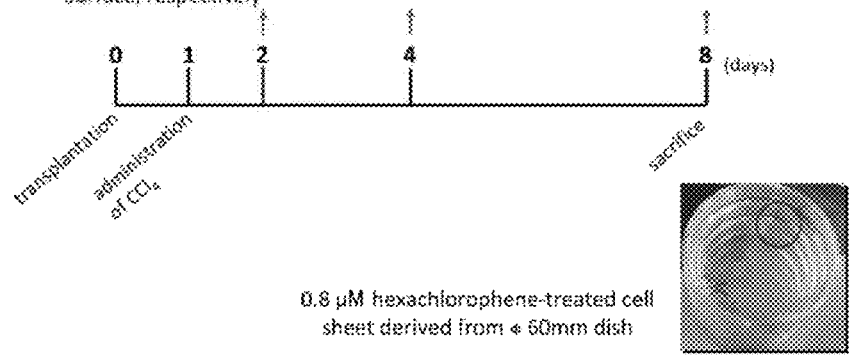

- animal : NOD/SCID (9-weeks old male mice)
- experimental group :
  - group 1 : sham operation (n=13)
  - group 2 : monolayer transplantation (n=10)
  - group 3 : 2 layers transplantation (n=13)
  - group 4 : 3 layers transplantation (n=13)
- operation : 0.8 µM hexachlorophene-tereated cell sheets transplanted into two sites of liver surface, respectively 0.8 µM hexachlorophene-treated cell sheet derived from Φ 60mm dish Effects of Transplanting Cell Sheet on Liver Surface in Acute Liver Dysfunction Model Decrease in Levels of Serum Transaminases After Cell Sheet Was Transplanted on Liver Surface in Acute Liver Dysfunction Model Decrease in Levels of Serum Bilirubin After Cell Sheet Was Transplanted on Liver Surface in Acute Liver Dysfunction Model Improvement in Survival Rate After Cell Sheet Was Transplanted on Liver Surface in Acute Liver Dysfunction Model Gene Expression Analysis Using Tissue Piece Containing Cell Sheet Transplanted on Liver Surface in Acute Liver Dysfunction Model Expression of Human Liver-specific Protein in Tissue Piece Containing Cell Sheet Transplanted on Liver Surface in Acute Liver Dysfunction Model Sorting Bone Marrow-derived CD90+CD271+ Mesenchymal Stem Cell with High Differentiation Efficiency and Proliferation Potential Effect of Inhibiting Wnt/β-catenin Signal by Low-molecular-weight Compound in Human Bone Marrow CD90+CD271+ Cells (Lonza Inc.)

Inducing Differentiation of Human Bone Marrow Mononuclear Cells (Lonza Inc.)-derived CD90+CD271+ Cells into Hepatocytes by Using Low-molecular-weight Compound

FIG. 31

Sampling of Clinical Specimen-derived Human Bone Marrow CD90+CD271+ Cells

| Age | Sex | Disease Name | Complication | Operation Site | Sample | Number of Nucleated cells | CD90+ CD271+ Cells |
|---|---|---|---|---|---|---|---|
| 79 | Female | Osteo-arthritis | No | Knee Joint Replacement Arthroplasty | Bone Marrow Aspirate 14 ml | $4.2 \times 10^8$ cells | 1,040 cells |
| 60 | Female | Osteo-arthritis | No | Hip Joint Replacement Arthroplasty | Bone Marrow Aspirate 18 ml | $5.0 \times 10^7$ cells | 374 cells |
| 55 | Female | Osteo-arthritis | No | Hip Joint Replacement Arthroplasty | Bone Marrow Aspirate 18 ml | $4.0 \times 10^7$ cells | 100 cells |
| 47 | Female | Osteo-arthritis | No | Hip Joint Replacement Arthroplasty | Bone Marrow Aspirate 10 ml | $5.4 \times 10^7$ cells | 2,342 cells |
| 67 | Female | Osteo-arthritis | No | Hip Joint Replacement Arthroplasty | Bone Marrow Aspirate 18 ml | $1.8 \times 10^8$ cells | 9,300 cells |
| 62 | Female | Osteo-arthritis | No | Hip Joint Replacement Arthroplasty | Bone Marrow Aspirate 7 ml | $5.0 \times 10^7$ cells | 10,620 cells |

FIG. 32

Inducing Differentiation of Clinical Specimen-derived Human Bone Marrow CD90+CD271+ Cells into Hepatocytes by Using Low-molecular-weight Compound

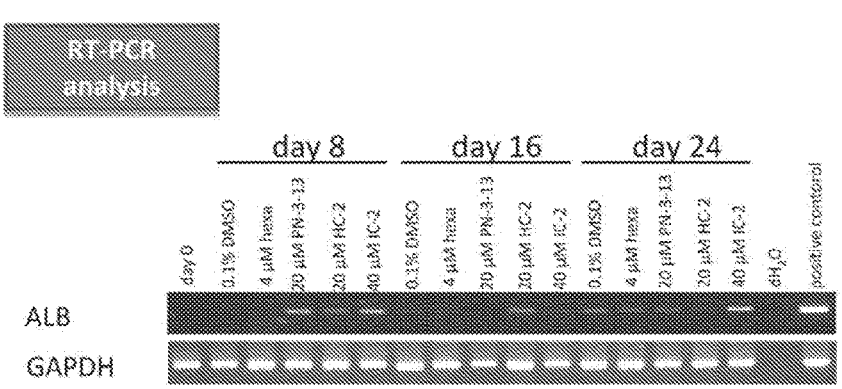

Inducing Differentiation of Clinical Specimen-derived Human Bone Marrow CD90+CD271+ Cells into Hepatocytes by Using Low-molecular-weight Compound Ability of Urea Synthesis when Bone Marrow CD90+CD271+ Cells Derived From 60 Years Old Female Patient With Osteoarthritis Were Differentiated into Hepatocytes $*P < 0.05$, $**P < 0.01$ compared with 0.1% DMSO as control Inducing Differentiation of Bone Marrow CD90+CD271+ Cells Derived from 60 Years Old Female Patient with Osteoarthritis into Hepatocytes PAS Staining Decrease in Levels of Serum Transaminases After Cell Sheet Was Transplanted on Liver Surface in Acute Liver Dysfunction Model Improvement in Survival Rate Was Compared between Transplantation of Cell Sheet on Liver Surface and Transplantation of Cells via Splenic/Portal Vein in Mouse with Acute Liver Dysfunction Effects of Transplantation of Cell Sheet on Liver Surface vs. Transplantation of Cells via Splenic/Portal Vein in Mouse with Acute Liver Dysfunction

SYNTHESIS AND ANALYSIS OF COMPOUNDS CAPABLE OF INDUCING DIFFERENTIATION OF HUMAN MESENCHYMAL STEMS CELLS INTO HEPATOCYTES

TECHNICAL FIELD

The present invention relates to a novel compound, an inducer of differentiation of mesenchymal stem cells into hepatocytes, and a Wnt/β-catenin signaling pathway inhibitor, and also relates to a method for producing hepatocytes using these compounds and hepatocytes as produced by the production method, etc.

BACKGROUND ART

Liver disease is said to be a disease so prevalent as to harm the nation as a whole in our country. Many patients are suffering from liver disease. In addition, about 34,000 people died of hepatocarcinoma in a year. Recently, because therapeutic intervention has advanced, a clinical outcome for treatment of hepatocarcinoma has been improved. As the number of patients with advanced cancer increases, the number of people dying of what is called liver failure caused by a decrease in liver functions due to combined hepatic cirrhosis increases. Liver transplantation is ideal for treatment of liver failure. In our country, however, it is difficult to obtain sufficient number of donors. Accordingly, stem cells should be used for development of liver regenerative therapy.

Tissue stem cells such as bone marrow cells and umbilical cord blood cells are promising as stem cells that may differentiate into hepatocytes. Accordingly, many research institutes have been conducting R&D so as to realize regenerative medicine using hepatocyte transplantation therapy for patients with chronic liver failure and so as to develop a genuinely clinically applicable, efficient differentiation-inducing technology that can differentiate human tissue stem cells into functional hepatocytes.

For example, the laboratory of Prof. Shiota of Tottori University Faculty of Medicine has reported differentiation into hepatocytes by inhibiting a Wnt/β-catenin signaling pathway by using RNA interference during differentiation induction from human mesenchymal stem cells into hepatocytes (Non Patent Literatures 1 and 3 to 5). In addition, other research institutes have also been researching the differentiation induction into hepatocytes (Non Patent Literature 2 and Patent Literatures 1 and 2).

Meanwhile, a large compound library containing 4,000 or more compounds has been recently screened. Then, five low-molecular-weight compounds capable of inhibiting a Wnt/β-catenin signaling pathway have been identified (Non Patent Literatures 6 to 9).

CITATION LIST

Patent Literature

Patent Literature 1: JP2009-535035A
Patent Literature 2: JP2010-75631A

Non Patent Literature

Non Patent Literature 1: Atsushi Yanagitani et al., "Retinoic Acid Receptor Dominant Negative Form Causes Steatohepatitis and Liver Tumors in Transgenic Mice", HEPATOLOGY, Vol. 40, No. 2, 2004, p. 366-375

Non Patent Literature 2: Seoyoung Park et al., "Hexachlorophene Inhibits Wnt/β-Catenin Pathway by Promoting Siah-Mediated β-Catenin Degradation", Mol Pharmacol Vol. 70, No. 3, 960-966, 2006

Non Patent Literature 3: Yoko Yoshida et al., "A role of Wnt/β-catenin signals in hepatic fate specification of human umbilical cord blood-derived mesenchymal stem cells", Am J Physiol Gastrointest Liver Physiol 293: G1089-G1098, 2007

Non Patent Literature 4: Shimomura T et al., "Hepatic differentiation of human bone marrow-derived UE7T-13 cells: Effects of cytokines and CCN family gene expression", Hepatol Res., 37, 1068-79, 2007

Non Patent Literature 5: Ishii K et al., "Hepatic differentiation of human bone marrow-derived mesenchymal stem cells by tetracycline-regulated hepatocyte nuclear factor 3 beta" Hepatology, 48, 597-606, 2008

Non Patent Literature 6: Maina Lepourcelet et al., "Small-molecule antagonists of the oncogenic Tcf/β-catenin protein complex", CANCER CELL, JANUARY 2004, VOL. 5, 91-102

Non Patent Literature 7: Emami K H et al., "A small molecule inhibitor of beta-catenin/CREB-binding protein transcription", Proc Natl Acad Sci USA. 2004 Aug. 24; 101(34):12682-7.

Non Patent Literature 8: Jufang Shan et al., "Identification of a Specific Inhibitor of the Dishevelled PDZ Domain", Biochemistry. 2005 Nov. 29; 44 (47): 15495-503

Non Patent Literature 9: Trosset J Y et al., "Inhibition of protein-protein interactions: the discovery of druglike beta-catenin inhibitors by combining virtual and biophysical screening", Proteins. 2006 Jul. 1; 64 (1): 60-7

SUMMARY OF INVENTION

Technical Problem

Unfortunately, the conventional technologies as described in the above literatures have had room for improvement regarding the following points.

Patent Literatures 1 and 2 describe proteins that induce hepatocytes from non-liver stem cells. Since a protein preparation has been used as a differentiation inducer, there is room for further improvement regarding aspects of stability and safety.

Non Patent Literatures 1 and 3 to 5 report differentiation induction from human mesenchymal stem cells into hepatocytes. Since siRNA has been used as a differentiation inducer, there is room for further improvement regarding aspects of stability and safety. Non Patent Literatures 2 and 6 to 9 are silent on a method for inducing differentiation into hepatocytes.

The present invention has been completed in light of the above situations. It is an object of the present invention to provide a low-molecular-weight compound effective in inducing differentiation of mesenchymal stem cells into hepatocytes. Also, it is another object of the present invention to provide a safe method for inducing differentiation of mesenchymal stem cells into hepatocytes with excellent differentiation efficiency, the method using the foregoing low-molecular-weight compound.

Solution to Problem

An aspect of the present invention provides at least one compound, a salt thereof, or a solvate of them, the compound being selected from the group consisting of compounds represented by formulae (1) and (2):

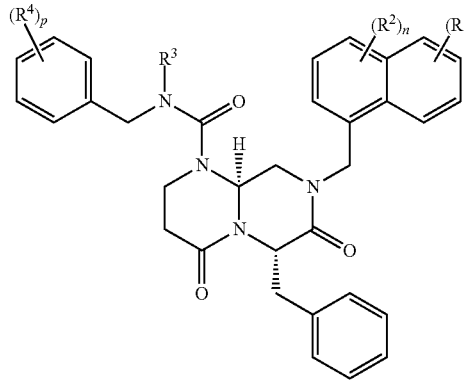

(1)

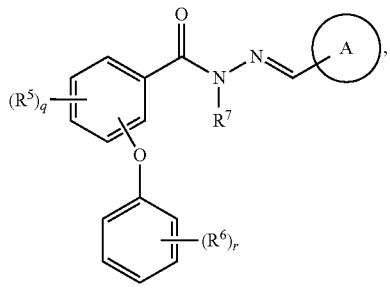

(2)

wherein $R^1$, $R^2$, $R^4$, $R^5$, and $R^6$ are the same or different from each other and each represents H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl;
$R^3$ and $R^7$ each represents H, optionally substituted $C_{1-6}$ alkyl, or optionally substituted $C_{2-6}$ alkenyl;
ring A is optionally substituted aryl or optionally substituted heteroaryl;
m and q are integers of any of 1 to 4;
n is an integer of any of 1 to 3; and
p and r are integers of any of 1 to 5,
with the proviso that N-[(5-methyl-2-furyl)methylideneamino]-2-phenoxy-benzamide is excluded.

When this compound, the salt thereof, or the solvate of them is used, differentiation of mesenchymal stem cells into hepatocytes can be induced as demonstrated in the following Examples. In addition, this compound, the salt thereof, or the solvate of them is a low-molecular-weight organic compound, and thus has better stability and safety than a protein preparation and/or a nucleic acid preparation. This allows for a safe differentiation-inducing method with excellent efficiency of differentiation of mesenchymal stem cells into hepatocytes.

In addition, another aspect of the present invention provides an inducer of differentiation of mesenchymal stem cells into hepatocytes, comprising at least one compound selected from the group consisting of compounds represented by formulae (1) and (2), a salt thereof, or a solvate of them. In addition, another aspect of the present invention provides a differentiation inducer comprising a compound, a salt thereof, or a solvate of them, the compound being represented by formula (8):

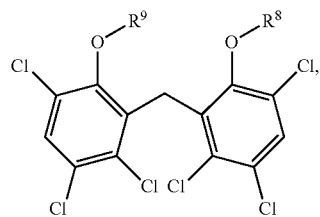

(8)

wherein $R^8$ and $R^9$ are the same or different from each other and each represents optionally substituted $C_{1-6}$ alkyl or optionally substituted $C_{2-6}$ alkenyl.

When this differentiation inducer is used, differentiation of mesenchymal stem cells into hepatocytes can be induced as demonstrated in the following Examples. In addition, a low-molecular-weight organic compound is used for this differentiation inducer, thereby imparting better stability and safety than a protein preparation and/or a nucleic acid preparation. This allows for a safe differentiation-inducing method with excellent efficiency of differentiation of mesenchymal stem cells into hepatocytes.

In addition, another aspect of the present invention provides a Wnt/β-catenin signaling pathway inhibitor comprising at least one compound selected from the group consisting of compounds represented by formulae (1) and (2), a salt thereof, or a solvate of them. In addition, another aspect of the present invention provides a Wnt/β-catenin signaling pathway inhibitor comprising a compound represented by formula (8), a salt thereof, or a solvate of them.

These Wnt/β-catenin signaling pathway inhibitors can inhibit a Wnt/β-catenin signaling pathway. Also, a low-molecular-weight organic compound is used for the inhibitors, thereby imparting better stability and safety than a protein preparation and/or a nucleic acid preparation.

In addition, another aspect of the present invention provides a method for producing hepatocytes from mesenchymal stem cells, comprising a step of treating mesenchymal stem cells with at least one compound selected from the group consisting of compounds represented by formulae (1) and (2), a salt thereof, or a solvate of them. Also, another aspect of the present invention provides a production method comprising a step of treating mesenchymal stem cells with the above differentiation inducer.

A low-molecular-weight organic compound is used for this production method, thereby imparting better stability and safety than a protein preparation and/or a nucleic acid preparation. This makes it possible to efficiently induce differentiation of mesenchymal stem cells into hepatocytes.

In addition, another aspect of the present invention provides hepatocytes differentiated from mesenchymal stem cells, comprising hepatocytes produced by treating mesenchymal stem cells with at least one compound selected from the group consisting of compounds represented by formulae (1) and (2), a salt thereof, or a solvate of them. Also, another aspect of the present invention provides hepatocytes produced by treating mesenchymal stem cells with the above differentiation inducer.

These hepatocytes are differentiated from mesenchymal stem cells by using a low-molecular-weight organic compound, so that this case has better stability and safety during production than the case of differentiation induction using a protein preparation and/or a nucleic acid preparation.

In addition, another aspect of the present invention provides a liver tissue or liver for regenerative medicine, comprising the above hepatocytes. This liver tissue or liver uses hepatocytes differentiated from mesenchymal stem cells by using a low-molecular-weight organic compound, so that this case has better stability and safety during production than the case of using stem cells for differentiation induction using a protein preparation and/or a nucleic acid preparation. Hence, the hepatocytes can be suitably used for a liver tissue or liver for regenerative medicine.

In addition, another aspect of the present invention provides a cell sheet comprising the above hepatocytes. Use of this cell sheet can suppress liver dysfunction as demonstrated in the following Examples. Also, this case has better stability and safety during production than the case of using stem cells for differentiation induction using a protein preparation and/or a nucleic acid preparation.

In addition, another aspect of the present invention provides a transplantation material comprising the above cell sheet and a support for collecting the cell sheet. Use of this transplantation material can suppress liver dysfunction as demonstrated in the following Examples. Also, this case has better stability and safety during production than the case of using stem cells for differentiation induction using a protein preparation and/or a nucleic acid preparation.

In addition, another aspect of the present invention provides a method for producing a transplantation material, comprising a step of treating stem cells with at least one compound selected from the group consisting of compounds represented by formulae (1) and (2), a salt thereof, or a solvate of them. In addition, another aspect of the present invention provides a production method comprising a step of performing treatment with a compound represented by formula (8), a salt thereof, or a solvate of them. Since a low-molecular-weight organic compound is used, these production methods have better stability and safety than a method using a protein preparation and/or a nucleic acid preparation.

In addition, another aspect of the present invention provides a method for producing a cell sheet for transplantation on a liver surface, comprising an induction step of treating mesenchymal stem cells with hexachlorophene, a derivative thereof, a salt of them, or a solvate of them to induce the mesenchymal stem cells into hepatocytes. Since a low-molecular-weight organic compound is used, this production method has better stability and safety than a method using a protein preparation and/or a nucleic acid preparation. Also, the cell sheet as prepared using this production method can exert an excellent effect of suppressing liver dysfunction when transplanted on a liver surface as demonstrated in the following Examples. Therefore, this production method is an excellent production method for producing a cell sheet for transplantation on a liver surface.

In addition, another aspect of the present invention provides a method for producing a cell sheet for transplantation on a liver surface, comprising an induction step of treating mesenchymal stem cells with a Wnt/β-catenin signaling pathway inhibitor to induce the mesenchymal stem cells into hepatocytes. The cell sheet as prepared using this production method can exert an excellent effect of suppressing liver dysfunction when transplanted on a liver surface as demonstrated in the following Examples. Therefore, this production method is an excellent production method for producing a cell sheet for transplantation on a liver surface.

Advantageous Effects of Invention

According to the present invention, a particular low-molecular-weight organic compound is used, thereby imparting better stability and safety than a protein preparation and/or a nucleic acid preparation. This makes it possible to efficiently induce differentiation of mesenchymal stem cells into hepatocytes. Also, a Wnt/β-catenin signaling pathway can be inhibited.

BRIEF DESCRIPTION OF DRAWINGS

FIG. 10 is electrophoresis gel images illustrating hepatocyte differentiation induction using IC-2, etc.

FIG. 11 is electrophoresis gel images illustrating hepatocyte differentiation induction using IC-2, etc.

FIG. 18 illustrates how to conduct an experiment for suppression of liver dysfunction when a cell sheet was transplanted under the skin.

FIG. 19 is graphs illustrating the results of how liver functions changed when a cell sheet was transplanted under the skin.

FIG. 20 is photographs of a liver and pictures illustrating the results of immunohistochemistry staining when a cell sheet was transplanted on a surface of liver.

FIG. 21 illustrates how to conduct an experiment for suppression of liver dysfunction when cell sheets were transplanted on two sites of a liver surface.

FIG. 31 is a table listing information on clinical specimens.

FIG. 32 is images illustrating the results of examining gene expression of a hepatocyte differentiation marker.

DESCRIPTION OF EMBODIMENTS

Figure 1:
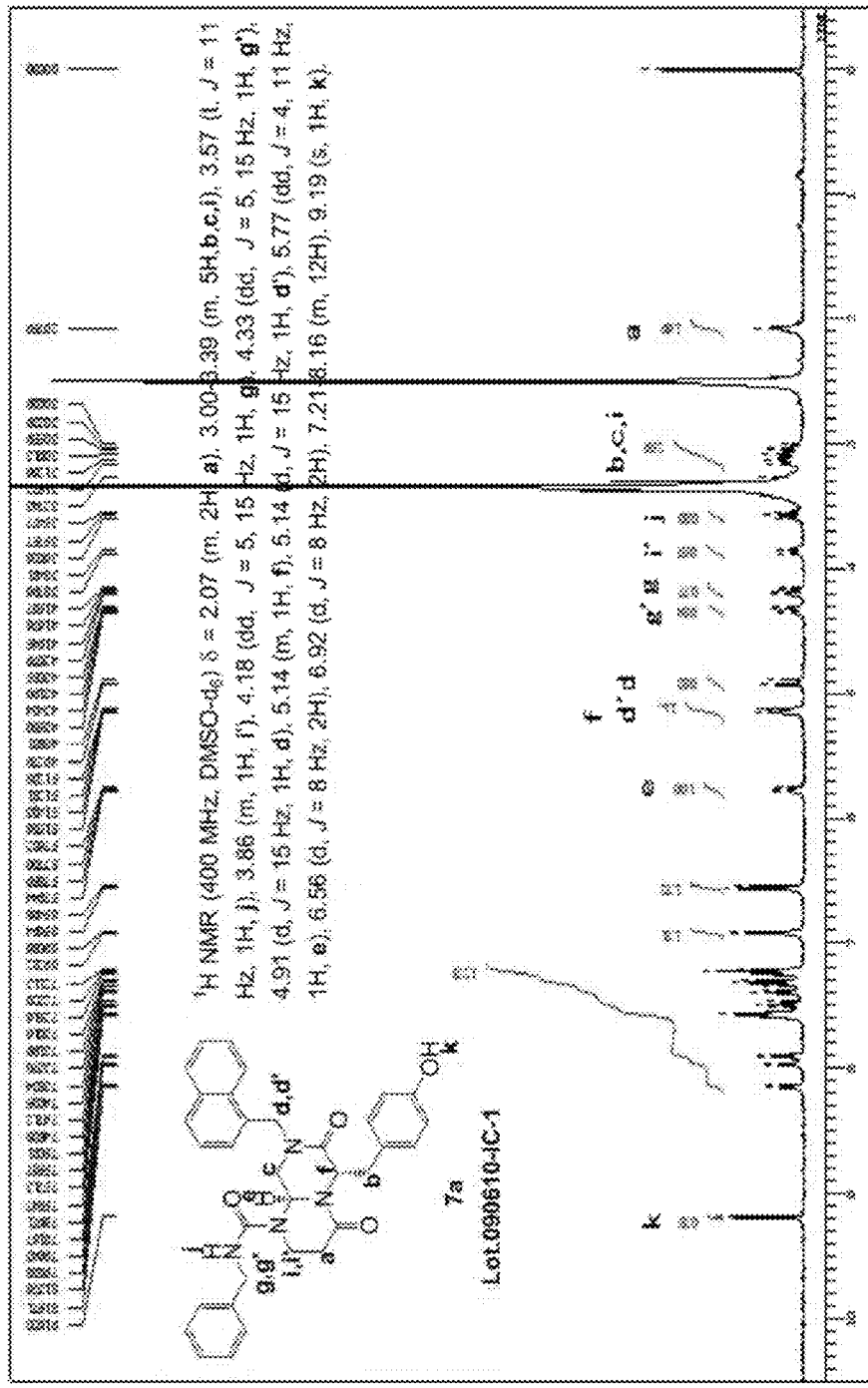
FIG. 1 shows spectrum data of ICG-001 described in Examples.

Hereinafter, embodiments of the present invention will be described in detail.

<Compounds>

A compound according to an embodiment of the present invention is at least one compound selected from the group consisting of compounds represented by formulae (1) and (2), a salt thereof, or a solvate of them. This compound, the salt thereof, or the solvate of them is a low-molecular-weight organic compound, and thus has better stability and safety than a protein preparation and/or a nucleic acid preparation. This allows for a safe differentiation-inducing method with excellent efficiency of differentiation of mesenchymal stem cells into hepatocytes.

In the formulae (1) and (2), $R^1$, $R^2$, $R^4$, $R^5$, and $R^6$ are the same or different from each other and each represents H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl. In addition, $R^3$ and $R^7$ each represents H, optionally substituted $C_{1-6}$ alkyl, or optionally substituted $C_{2-6}$ alkenyl. In addition, ring A is optionally substituted aryl or optionally substituted heteroaryl. In addition, m and q are integers of any of 1 to 4. In addition, n is an integer of any of 1 to 3. In addition, p and r are integers of any of 1 to 5. In this regard, however, N-[(5-methyl-2-furyl)methylideneamino]-2-phenoxy-benzamide is excluded.

The above $R^1$, $R^2$, $R^4$, $R^5$, and $R^6$ are the same or different from each other and may each represent H, halogen, nitro, cyano, OH, $C_{1-6}$ alkyl, halogeno $C_{1-6}$ alkyl, hydroxy $C_{1-4}$ alkyl, $C_{1-6}$ alkyl amino, $C_{1-6}$ alkoxy, halogeno $C_{1-6}$ alkoxy, hydroxy $C_{1-6}$ alkoxy, or $C_{1-6}$ alkoxy amino. The above $R^3$ and $R^7$ may each represent H. Also, the above ring A may be optionally substituted naphthyl, phenyl substituted with five halogens, or furyl substituted with one methyl.

As used herein, the term "halogen" means F, Cl, Br, or I.

As used herein, unless otherwise indicated, the terms "alkyl" and "alkenyl" mean a linear or branched hydrocarbon chain.

As used herein, the term "$C_{1-6}$" refers to hydrocarbon containing 1, 2, 3, 4, 5, or 6 carbon atoms. That is, the term "$C_{1-6}$ alkyl" refers to alkyl containing 1, 2, 3, 4, 5, or 6 carbon atoms. Examples of $C_{1-6}$ alkyl include methyl, ethyl, n-propyl, isopropyl, n-butyl, isobutyl, sec-butyl, tert-butyl, n-pentyl, and n-hexyl.

As used herein, examples of "alkenyl" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

As used herein, examples of "alkoxy" include methoxy, ethoxy, propoxy, isopropoxy, butoxy, isobutoxy, sec-butoxy, tert-butxy, pentoxy, isopentoxy, and hexoxy.

As used herein, the term "optionally substituted" means that a compound is unsubstituted or has 1, 2, 3, 4, or 5 substituents at positions which can be substituted. Note that when a plurality of substituents are included, these substituents may be the same or different from each other. In addition, the position of each substitution may be position 1, 2, 3, 4, 5, 6, 7, 8, or 9. Here, examples of the substituents include H, halogen, nitro, cyano, OH, $C_{1-6}$ alkyl, halogeno $C_{1-6}$ alkyl, hydroxy $C_{1-6}$ alkyl, $C_{1-6}$ alkyl amino, $C_{3-6}$ cycloalkyl, $C_{2-6}$ alkenyl, halogeno $C_{2-6}$ alkenyl, hydroxy $C_{2-6}$ alkenyl, $C_{2-6}$ alkenylamino, $C_{3-6}$ cycloalkenyl, $C_{2-6}$ alkynyl, halogeno $C_{2-6}$ alkynyl, hydroxy $C_{2-6}$ alkynyl, $C_{2-6}$ alkynyl amino, $C_{1-6}$ alkoxy, halogeno $C_{1-6}$ alkoxy, hydroxy $C_{1-6}$ alkoxy, $C_{1-6}$ alkoxy amino, aryl, and heteroaryl.

As used herein, the "halogeno $C_{1-6}$ alkyl" refers to $C_{1-6}$ alkyl that is substituted by one or more halogens. The number of halogens may be, for example, 1, 2, 3, 4, 5, 6, or 13. Also, the number may be within a range between any two numbers indicated above. In addition, when two or more halogens are included, the kind of each halogen may be the same or different from each other. Examples of halogeno $C_{1-6}$ alkyl include, chloromethyl, dichloromethyl, trichloromethyl, fluoromethyl, difluoromethyl, trifluoromethyl, bromomethyl, dibromomethyl, tribromomethyl, chloroethyl, dichloroethyl, trichloroethyl, fluoroethyl, difluoroethyl, and trifluoroethyl.

As used herein, the "hydroxy $C_{1-6}$ alkyl" refers to $C_{1-6}$ alkyl that is substituted by one or more hydroxy groups. The number of the hydroxy groups may be, for example, 1, 2, 3, 4, 5, 6, or 13. Also, the number may be within a range between any two numbers indicated above. Examples of hydroxy $C_{1-6}$ alkyl include hydroxymethyl, 1-hydroxyethyl, 2-hydroxyethyl, 2-hydroxy-n-propyl, and 2,3-dihydroxy-n-propyl.

As used herein, the "$C_{1-6}$ alkyl amino" refers to $C_{1-6}$ alkyl that is substituted by one or more amino groups. The number of the amino groups may be, for example, 1, 2, 3, 4, 5, 6, or 13. Also, the number may be within a range between any two numbers indicated above. Examples of $C_{1-6}$ alkyl amino include methyl amino and ethyl amino.

As used herein, the "halogeno $C_{1-6}$ alkoxy" is equivalent to halogeno $C_{1-6}$ alkyl whose alkyl is replaced by alkoxy. Examples of halogeno $C_{1-6}$ alkoxy include fluoromethoxy, difluoromethoxy, trifluoromethoxy, 1-fluoroethoxy, 2-fluoroethoxy 2-chloroethoxy, 2-bromoethoxy, (1,1-difluoro)ethoxy, (1,2-difluoro)ethoxy, (2,2,2-trifluoro)ethoxy, (1,1,2,2-tetrafluoro)ethoxy, (1,1,2,2,2-pentafluoro)ethoxy, 1-fluoro-n-propoxy, 1,1-difluoro-n-propoxy, 2,2-difluoro-n-propoxy, 3-fluoro-n-propoxy, (3,3,3-trifluoro)-n-propoxy, (2,2,3,3,3-pentafluoro)-n-propoxy, 4-fluoro-n-butoxy, (4,4,4-trifluoro)-n-butoxy, 5-fluoro-n-pentyloxy, (5,5,5-trifluoro)-n-pentyloxy, 6-fluoro-n-hexyloxy, (6,6,6-trifluoro)-n-hexyloxy, 2-fluorocyclopropoxy, and 2-fluorocyclobutoxy.

As used herein, the "hydroxy $C_{1-6}$ alkoxy" is equivalent to hydroxy $C_{1-6}$ alkyl whose alkyl is replaced by alkoxy. Examples of hydroxy $C_{1-6}$ alkoxy include 2-hydroxyethoxy, 2-hydroxy-n-propoxy, 3-hydroxy-n-propoxy, 2,3-dihydroxy-n-propoxy, and 2-hydroxycyclopropyl.

As used herein, the "$C_{1-6}$ alkoxy amino" is equivalent to $C_{1-6}$ alkyl amino whose alkyl is replaced by alkoxy. Examples of $C_{1-6}$ alkoxy amino include methoxy amino and ethoxy amino.

As used herein, the term "aryl" refers to a $C_{6-14}$ monocyclic, dicyclic, or tricyclic aromatic hydrocarbon ring. Examples of aryl include phenyl, naphthyl (e.g., 1-naphthyl, 2-naphthyl), tetrahydronaphthalenyl, indenyl, and phenyl that is substituted with five halogens. Also, aryl includes a ring group that is condensed with $C_{5-8}$ cycloalkene at its double bond position.

As used herein, the "heteroaryl" includes groups having 5 to 14 ring atoms and shared n-electrons within its rings, and having 1 to 4 heteroatoms selected from the group consisting of N, S, and O. Examples of heteroaryl include thienyl, benzothienyl, furyl, benzofuryl, dibenzofuryl, pyrrolyl, imidazolyl, pyrazolyl, pyridyl, pyrazinyl, pyrimidinyl, pyridazinyl, tetrazolyl, oxazolyl, thiazolyl, and isooxazolyl.

As used herein, examples of the "salt" include, but are not particularly limited to, anionic salts that are formed using any acidic group (e.g., carboxyl) and cationic salts that are formed using any basic group (e.g., amino). Examples of the salts include inorganic salts, organic salts, and salts disclosed in an article (Berge, Bighley, and Monkhouse, J. Pharm. Sci., 1977, 66, 1-19). The examples further include metal salts, ammonium salts, salts with an organic base, salts with an inorganic acid, salts with an organic acid, and salts with a basic or acidic amino acid. Examples of the metal salts include alkali metal salts (e.g., sodium salts, potassium salts), alkaline earth metal salts (e.g., calcium salts, magnesium salts, barium salts), and aluminum salts. Examples of the salts with an organic base include salts with trimethylamine, triethylamine, pyridine, picoline, 2,6-lutidine, ethanolamine, diethanolamine, triethanolamine, cyclohexylamine, dicyclohexylamine, or N,N'-dibenzylethylenediamine. Examples of the salts with an inorganic acid include salts with hydrochloric acid, hydrobromic acid, nitric acid, sulfuric acid, or phosphoric acid. Examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, or p-toluenesulfonic acid. Examples of the salts with a basic amino acid include salts whit arginine, lysine, or ornithine. Examples of the salts with an acidic amino acid include salts with aspartic acid or glutamic acid.

As used herein, the term "solvate" refers to a compound formed by a solute and a solvent. A dictionary (J. Honig et al., The Van Nostrand Chemist's Dictionary P650 (1953)) can be consulted regarding the solvate. If the solvent is water, the solvate formed is a hydrate. Preferably, the solvent does not interfere with a biological activity of the solute. Examples of the preferable solvent include, but are not limited to, water, ethanol, and acetic acid. The most preferred solvent is water. A compound or a salt thereof according to an embodiment of the present invention absorbs moisture when contacting air or recrystallized. They sometimes possess hygroscopic moisture or become a hydrate. As used herein, the term "isomer" includes molecules whose molecular formula is identical but whose structure is different. Examples of the isomer include enantiomers, geometric (cis/trans) isomers, and isomers (diastereomers) having one or more chiral centers that are not mirror images of each other. As used herein, the term "prodrug" includes a precursor compound in which when the above compound is administered to a subject, a chemical change occurs due to metabolic processes or various chemical reactions to give a compound, a salt thereof, or a solvate of them according to the present invention. With regard to the prodrug, an article (T. Higuchi and V. Stella, "Pro-Drugs as Novel Delivery Systems", A.C.S. Symposium Series, Volume 14) can be referred to.

A compound according to an embodiment of the present invention is at least one compound, a salt thereof, or a solvate of them, the compound being selected from the group consisting of compounds represented by formulae (3) to (5):

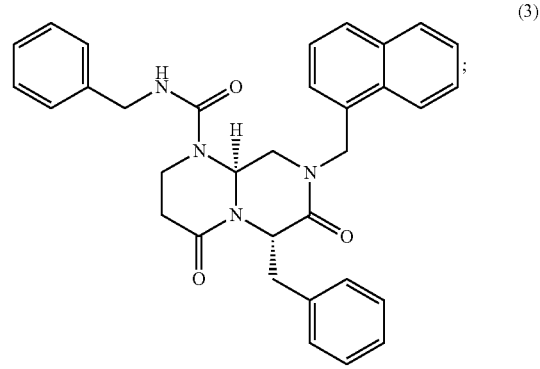

(3)

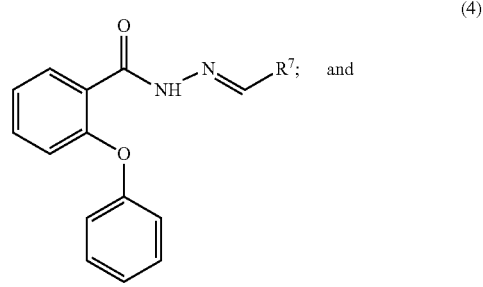

(4)

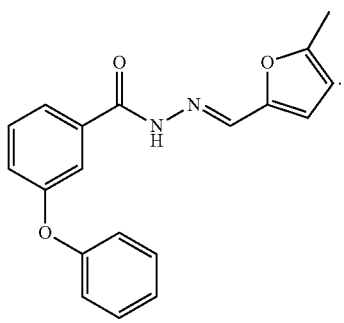

(5)

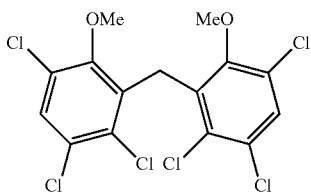

(9)

In the formula (4), $R^7$ is optionally substituted naphthyl or phenyl substituted with five halogens.

In addition, a compound according to an embodiment of the present invention is at least one compound selected from the group consisting of compounds represented by formulae (3), (5), (6), and (7), a salt thereof, or a solvate of them. In view of efficiency of differentiation of mesenchymal stem cells into hepatocytes, it is preferable that the structure of the compound according to an embodiment of the present invention is similar to those of the above compounds.

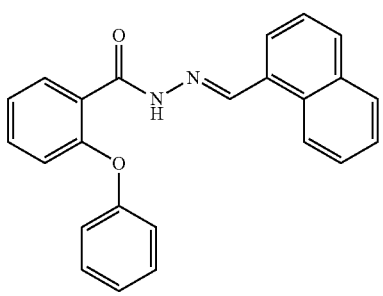

(6)

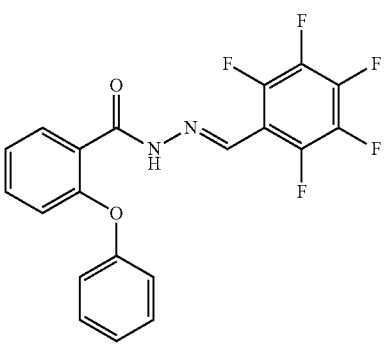

(7)

<Inducer of Differentiation of Mesenchymal Stem Cells into Hepatocytes>

An inducer of differentiation of mesenchymal stem cells into hepatocytes according to an embodiment of the present invention is a differentiation inducer comprising at least one compound selected from the group consisting of compounds represented by formulae (1) to (7), a salt thereof, or a solvate of them. Otherwise, the above differentiation inducer comprises at least one compound selected from the group consisting of compounds represented by formulae (8) and (9), a salt thereof, or a solvate of them. A low-molecular-weight organic compound is used for these differentiation inducers, thereby imparting better stability and safety than a protein preparation and/or a nucleic acid preparation. This allows for a safe differentiation-inducing method with excellent efficiency of differentiation of mesenchymal stem cells into hepatocytes.

In the formula (8), $R^8$ and $R^9$ are the same or different from each other and each represents optionally substituted $C_{1-6}$ alkyl or optionally substituted $C_{2-6}$ alkenyl. In addition, in view of efficiency of the differentiation, it is preferable that the structure of the compound contained in an inducer of differentiation of mesenchymal stem cells into hepatocytes according to this embodiment has a structure similar to those of one or more compounds selected from compounds represented by formulae (3), (5), (6), (7), and (9).

As used herein, the term "mesenchymal stem cells" includes somatic stem cells derived from mesenchyme. These mesenchymal stem cells can differentiate into mesenchymal cells. These mesenchymal stem cells should be applicable to regenerative medicine such as restructuring of bones, blood vessels, and cardiac muscles in a near future.

Examples of the "mesenchymal stem cells" include bone marrow mesenchymal stem cells and umbilical cord blood-derived stem cells. The mesenchymal stem cells seem to be present in all tissues containing a mesenchymal tissue. Among the mesenchymal tissues, the bone marrow mesenchymal stem cells, however, can be easily collected by bone marrow aspiration, and their culture technique has been established. Bone marrow stromal cells contain bone marrow mesenchymal stem cells, and are one type of cells supporting hematopoietic cells mainly contained in bone marrow. Meanwhile, umbilical cord blood includes blood contained in an umbilical cord that constitutes a fetal tissue connecting a fetus and its mother. It is known that this umbilical cord blood contains a large amount of the umbilical cord blood-derived stem cells (hematopoietic stem cells). Recently, mesenchymal stem cells (i.e., umbilical cord blood-derived mesenchymal stem cells), which are somatic stem cells other than the hematopoietic stem cells, have been found in umbilical cord blood. To date, the mesenchymal stem cells have been reported to be present in bone marrow. However, it has been indicated that not only bone marrow but also umbilical cord blood can provide a source for mesenchymal stem cells, and may be applicable for bone- and/or cartilage-repair using tissue engineering or clinical application to regenerative medicine.

Here, the mesenchymal stem cells, in general, have a short life span and are not necessarily easy to culture in vitro for a long period. However, a human bone marrow-derived and a human umbilical cord blood-derived mesenchymal stem cell lines that have the hTERT gene introduced and can stably proliferate have already been established. While these cells stably proliferate, they have no chromosome abnormalities but have functional contact inhibition. Besides, they do not form tumors when transplanted into an immunosuppressed animal. Also, since they do not affect cellular differentiation, these cells are useful for research on differentiation of mesenchymal stem cells.

In addition, as used herein, the term "hepatocytes" includes cells with a size of about 20 μm, the cells constituting 70 to 80% of a liver. Examples of general functions of hepatocytes include: synthesis and storage of proteins; conversion of carbohydrate; synthesis of cholesterol, bile acid, and phospholipids; and detoxification, denaturing, and excretion of endogenous and exogenous substances. Also, the examples further include promotion of generation and secretion of bile.

As used herein, the term "differentiation" includes a structural and functional change of individual cells in a multicellular organism. Generally speaking, differentiation of a stem cell into a functional cell in a multicellular organism is often irreversible in many cases. Previous findings have taught that a mesenchymal stem cell has multipotency, that is, has an ability of differentiating into a wide variety of cell types while cell lineages that can be differentiated are limited. Therefore, the mesenchymal stem cell, in general, cannot be differentiated into cells derived from a different germ layer. Here, an inducer of differentiation of mesenchymal stem cells into hepatocytes according to this embodiment can induce differentiation of mesenchymal stem cells into hepatocytes that are derived from a different germ layer. This point can be said to be a big technical feature.

Generally speaking, it is quite natural to use liver stem cells as a cell source for liver regenerative medicine. However, since the liver stem cells only appear during severe liver damage such as fulminant hepatitis, collection of the stem cells from an actual patient is not practical. Then, tissue stem cells other than liver stem cells or iPS cells could be a cell source for liver regenerative medicine. Recent reports have shown that mesenchymal stem cells can differentiate into cells with a certain degree of liver function under in vitro conditions. That is, addition of various cytokines to mesenchymal stem cells, followed by culturing for about 4 weeks, has reportedly promoted differentiation into hepatocyte-like cells. The mesenchymal stem cells are present in bone marrow and umbilical cord blood, and are relatively easy to collect. Use of bone marrow has an advantage of avoiding immune rejection because of use of autologous cells. Alternatively, umbilical cord blood is usually disposed, so there is an advantage of having less ethical issues. In view of the above, the mesenchymal stem cells are a promising cell source for liver regenerative medicine.

As used herein, the "Wnt/β-catenin signaling pathway" includes one of pathways that regulate a cell fate decision during development of vertebrates and invertebrates. A Wnt ligand is a typical glycoprotein that binds to a secretory Frizzled receptor. Its binding triggers a signaling cascade, which results in dissociation of a multifunctional kinase GSK-3β from an APC/Axin/GSK-3β complex. Without the Wnt signal (i.e., off state), (β-catenin, which is a transcriptional coactivator and an essential adaptor protein for cell-to-cell adhesion, becomes a target for degradation by the APC/Axin/GSK-3β complex. CK1 and GSK-3β act coordinately to properly phosphorylate α-catenin. Then, the β-catenin gets ubiquitinated and is degraded by a β-TrCP/SKP complex in proteasomes.

When Wnt binds to the receptor (i.e., on state), Dishevelled (Dsh) seems to be at least partially phosphorylated to be activated. Next, GSK-3β dissociates from a degradation-inducing complex. This facilitates stabilization of the level of β-catenin expression, nuclear translocation, and recruitment of LEF/TCF to a DNA-binding factor. Then, (β-catenin replaces a Griucho-HDAC corepressor and serves as a transcriptional activator.

In addition, similar to the transcriptional repressor complex, a complex with Prop1, a homeodomain factor, is shown to have β-catenin that exerts its functions by conditional activation. Importantly, several human cancers have been found to contain β-catenin point mutations that lead to uncontrollable stabilization of β-catenin. In addition, it has been reported that APC and Axin also contain mutations. Thus, it has been emphasized that aberrant activation of this pathway relates to human tumors. During a course of development, the Wnt/β-catenin signaling pathway plays a role in integration of signals from various pathways such as retinoic acid, FGF, TGF-β, and BMP in different cell types and/or tissues. Further, GSK-3β, which is a component of the Wnt/β-catenin signaling pathway, is involved in glycogen metabolism and other major pathways. Thus, inhibition of GSK-3β is considered to be a reasonable measure to treat diabetes and/or neurodegenerative disease.

As used herein, the term "low-molecular-weight organic compound" includes an organic compound with a molecular weight of 2000 or less. The molecular weight is preferably 1000 or less, more preferably 900 or less, and still more preferably 800 or less. Since a high-molecular-weight compound including a nucleic acid preparation and a protein preparation is susceptible to degradation in vivo and in vitro, the compound is unstable. When the compound is used in regenerative medicine, a safety concern remains. In contrast, since the low-molecular-weight organic compound is unlikely to be degraded in vivo and in vitro, the compound is stable. Thus, when used in regenerative medicine, the compound has an advantage of safety. In addition, as the molecular weight becomes smaller, its organic synthesis becomes easier. Further, the compound has excellent feasibility such as stability and safety. Note that peptides and nucleotides are excluded in this low-molecular-weight organic compound. This is because the peptides and the nucleotides are susceptible to degradation in vivo and in vitro, thereby being unstable. Besides, when they are used in regenerative medicine, a safety concern still remains.

Under these circumstances, the present inventors have synthesized various low-molecular-weight organic compounds, and have evaluated the compounds according to the following points. As a result, the present inventors have discovered that five low-molecular-weight organic compounds (hereinafter, sometimes referred to as "IC-2, etc.") including IC-2, HC-1, PN-3-4, PN-3-13, and PN-1-2 can induce differentiate of mesenchymal stem cells into hepatocytes as demonstrated in the below-described Examples.
1. Expression of Liver-specific Transcription Factors;
2. Expression of Liver-specific Proteins;
3. Glycogen Synthesis;
4. Urea Synthesis; and
5. Evaluation of Signal Strength of Wnt/β-catenin Signaling Pathway Having TCF Activity by Using Luciferase Activity Measurement.

Examples of the above-mentioned inducer of differentiation of mesenchymal stem cells into hepatocytes according to an embodiment of the present invention include low-molecular-weight organic compounds (e.g., IC-2) that inhibit the Wnt/β-catenin signaling pathway. These low-molecular-weight compounds have better feasibility such as stability and safety than protein preparations and/or nucleic acid preparations, so the compounds should provide a promising method to realize regenerative medicine.

Note that in this embodiment, it is determined whether or not a low-molecular-weight organic compound, which is a candidate substance for the differentiation inducer, has characteristics of inducing differentiation of mesenchymal stem cells into hepatocytes. In order to determine the above, whether or not expression of at least one protein selected from the group consisting of albumin, C/EBPα, CYP1A1, and CYP3A4 is induced is a critical indicator. This is because hepatocytes, in general, have increased levels of expression of at least one protein (hereinafter, sometimes referred to as "albumin, etc.") selected from the group consisting of the above albumin, C/EBPα, CYP1A1, and CYP3A4, but mesenchymal stem cells have low levels of expression of the albumin, etc.

Note that at this time, if the level of expression of albumin, etc., exceeds a predetermined threshold in post-treatment mesenchymal stem cells, it is determined that the candidate substance can induce differentiation of the mesenchymal stem cells into hepatocytes. In contrast, if the expression is lower than the predetermined threshold, it is determined that the candidate substance is not characterized by inducing differentiation of the mesenchymal stem cells into hepatocytes. This threshold, for example, may be set to 1.5 or more, 2 or more, 5 or more, or 10 or more times as large as the average of each expression level of albumin, C/EBPα, CYP1A1, and CYP3A4 in mesenchymal stem cells before treatment. Also, this threshold, for example, may be set to 2 or more, 5 or more, or 10 or more times as large as the average ± standard deviation of each expression level of albumin, C/EBPα, CYP1A1, and CYP3A4 in mesenchymal stem cells before treatment.

Alternatively, it may be determined whether or not the expression level of any of albumin, C/EBPα, CYP1A1, and CYP3A4 in mesenchymal stem cells treated with the candidate substance has, for example, a significantly higher expression level than that in mesenchymal stem cells before treatment. With regard to a test for the significant difference, it is preferable to have a significant difference in, for example, Student's t-test, which is a parametric test, when a population is assumed to have a Gaussian distribution. Specifically, in the Student's t-test, a one-sided test should give preferably p<0.05, more preferably p<0.03, and still more preferably p<0.01. Note that the Student's t-test is not limited to the one-sided test, but may be a two-sided test. Further, if the population is not assumed to have a Gaussian distribution, whether or not there is a significant difference may be determined by using a Mann-Whitney U test as a non-parametric test.

In addition, in order to determine whether or not a low-molecular-weight organic compound, which is a candidate substance for the differentiation inducer, is characterized by inducing differentiation of mesenchymal stem cells into hepatocytes in an embodiment of the present invention, whether or not the compound increases an ability of glycogen production or urea synthesis in the mesenchymal stem cells gives another critical indicator. This is because while hepatocytes, in general, have increased the ability of glycogen production or urea synthesis, mesenchymal stem cells fail to have increased the ability of glycogen production or urea synthesis. Note that at this time, a threshold or significant difference is used for determination in a manner similar to those when the above expression level of albumin, etc., is determined.

<Wnt/β-Catenin Signaling Pathway Inhibitor>

An embodiment of the present invention provides a Wnt/β-catenin signaling pathway inhibitor comprising at least one compound selected from the group consisting of compounds represented by formulae (1) and (2), a salt thereof, or a solvate of them. In addition, another embodiment provides a Wnt/β-catenin signaling pathway inhibitor comprising a compound represented by formula (8), a salt thereof, or a solvate of them. Use of these Wnt/β-catenin signaling pathway inhibitors can inhibit a Wnt/β-catenin signaling pathway. Also, a low-molecular-weight organic compound is used for the inhibitors, thereby imparting better stability and safety than a protein preparation and/or a nucleic acid preparation.

In the formula (8), $R^8$ and $R^9$ are the same or different from each other and each represents optionally substituted $C_{1-6}$ alkyl or optionally substituted $C_{2-6}$ alkenyl. In addition, as a compound contained in a Wnt/β-catenin signaling pathway inhibitor according to this embodiment has a structure more similar to those of one or more compounds selected from compounds represented by formulae (3), (5), (6), (7), and (9), the structure is more preferable in view of efficiency of the Wnt/β-catenin signaling pathway inhibition.

<Method for Producing Hepatocytes from Mesenchymal Stem Cells>

A method for producing hepatocytes according to an embodiment of the present invention is a production method comprising a step of treating mesenchymal stem cells with at least one compound selected from the group consisting of compounds represented by formulae (1) to (2), a salt thereof, or a solvate of them. Also, the production method comprises the step of treating mesenchymal stem cells with the above differentiation inducer. A low-molecular-weight organic compound is used for these production methods, thereby imparting better stability and safety than a protein preparation and/or a nucleic acid preparation. This makes it possible to efficiently induce differentiation of mesenchymal stem cells into hepatocytes.

Note that at this time, it is preferable to include a step of treating the mesenchymal stem cells with the differentiation inducer for 8 days or more as demonstrated in the below-described Examples. Progression of changes in various molecular biological intracellular events takes such long time because differentiation of mesenchymal stem cells into hepatocytes contains biological processes. In this case, since the differentiation inducer according to this embodiment is a low-molecular-weight organic compound, it has superior stability. Thus, treatment for a long period of 8 days or more is unlikely to make the compound degraded. However, it is preferable to appropriately change a medium so as to supply nutrients necessary for survival, proliferation, and changes of the mesenchymal stem cells. At such occasion, it is also preferable to add the low-molecular-weight organic compound in a freshly replaced medium, the amount of the low-molecular weight organic compound being substantially the same as that of the medium before the change.

In addition, since the differentiation inducer according to this embodiment is a low-molecular-weight organic compound, it has superior stability. Thus, whether the treatment temperature is high or low is unlikely to affect its decomposition. It is preferable to set a temperature of a medium to a temperature suitable for survival of mammalian cells so as to maintain an environment necessary for survival, proliferation, and changes of the mesenchymal stem cells. Specifically, the temperature is set to be preferably from 20 to 45° C., more preferably from 30 to 40° C., and still more preferably from about 36 to about 38° C.

In this case, a method for culturing mesenchymal stem cells is not particularly limited, but it is preferable allow them to contact a low-molecular-weight organic compound in a medium suitable for survival of the mesenchymal stem cells on, for example, a temperature-responsive culture dish.

Examples of a preferred medium that can be used include Dulbecco's modified Eagle's Medium (DMEM) and Mesenchymal Stem Cell Basal Medium (MSCBM).

At that time, examples of a preferred temperature-responsive culture dish include culture dishes whose surface has been polymerized with a temperature-responsive polymer (e.g., PIPAAm) and/or methyl cellulose. This is because merely decreasing the temperature would enable cells to be collected without damage while maintaining intercellular adhesion.

<Application in Regenerative Medicine>

The hepatocytes as so differentiated can be suitably used for transplantation therapeutics, such as hepatocyte transplantation, and application for drug development in evaluation of a drug's efficacy and adverse effect. In addition, these hepatocytes are differentiated from mesenchymal stem cells by using a low-molecular-weight organic compound, so that this case has better stability and safety during production than the case of differentiation induction using a protein preparation and/or a nucleic acid preparation.

Further, the hepatocytes as so differentiated may be grown to fit a desired shape by using a temperature-responsive culture dish and/or a substrate such as a synthetic polymer scaffold using a biodegradable synthetic polymer such as polylactic acid (PLA) and polyethylene glycolic acid (PGA). Then, the resulting hepatocytes can be used as a liver tissue, liver, or cell sheet for regenerative medicine. The resulting 3D-structured liver tissue, liver, or cell sheet for regenerative medicine can be suitably used for transplantation therapeutics, such as hepatocyte transplantation, and application for drug development in evaluation of a drug's efficacy and adverse effect. In addition, the liver tissue, liver, or cell sheet is differentiated from mesenchymal stem cells by using a low-molecular-weight organic compound, so that this case has better stability and safety during production than the case of differentiation induction using a protein preparation and/or a nucleic acid preparation.

Further, the above hepatocytes, liver tissue, liver, or cell sheet may have components comprising, for example, at least one compound selected from the group consisting of compounds represented by formulae (1) and (2), a salt thereof, or a solvate of them. Furthermore, they may comprise a compound represented by formula (8), a salt thereof, or a solvate of them.

In addition, the levels of expression of genes in the above hepatocytes are not particularly limited, but the levels of expression of at least one gene selected from any of transthyretin, apolipoprotein B, haptoglobin, fibrinogen α, and fibrinogen β, for example, may be lower than those of the above genes in commercially available hepatocytes. Also, the levels of expression of any of the above genes may be lower than those of hepatocytes in the liver of a patient transplanted with the above hepatocytes. Note that the term "commercially available" includes those commercially available for regenerative medicine or research purposes. In addition, the phrase "is lower" includes a state in which the level of the gene expression is significantly or substantially decreased. Also, the level may be decreased by 40, 50, 60, 70, 80, 90, or 100%. This rate may be any one of the above values or higher, or may be between any two of the above values.

In addition, the levels of expression of genes in the above liver tissue, liver, or cell sheet are not particularly limited, but the levels of expression of at least one gene selected from any of transthyretin, apolipoprotein B, C4, RBP4, RBP1, haptoglobin, fibrinogen α, and fibrinogen β, for example, may be lower than those of the above genes in commercially available hepatocytes, liver tissues, or livers. Also, the levels of expression of any of the above genes may be lower than those of hepatocytes in the liver, a liver tissue, or the liver of a patient transplanted with the above hepatocytes.

Moreover, an embodiment of the present invention provides a therapeutic agent or a material for treating liver dysfunction or a disease accompanied by the liver dysfunction, comprising hepatocytes, a liver tissue, a liver, or a cell sheet according to an embodiment of the present invention. Also, an embodiment of the present invention provides a method for treating liver dysfunction or a disease accompanied by the liver dysfunction by using the above material.

<Cell Sheet>

An embodiment of the present invention provides a cell sheet comprising hepatocytes as differentiated in such a manner as described above. Use of this cell sheet can suppress liver dysfunction as demonstrated in the following Examples. Therefore, the cell sheet can be suitably used for treatment of liver dysfunction.

In addition, this cell sheet may be used for transplantation on a liver surface. When this cell sheet is transplanted on a liver surface, the following Examples demonstrate a remarkable effect of suppressing liver dysfunction.

Also, for transplantation, one or more layers of this cell sheet may be transplanted. In addition, with regard to the transplantation site, one or more sites may be selected. The number of sites may be, for example, 2, 3, 4, 5, or 6. The number may be the above number or more, or may be between any two of the above numbers.

Another embodiment of the present invention provides a transplantation material comprising the above cell sheet and a support for collecting the cell sheet. Use of this transplantation material can suppress liver dysfunction as demonstrated in the following Examples. For example, when used, this transplantation material is placed on a site of interest. Next, the cell sheet is made to contact the site. Then, the support for collecting the cell sheet may be removed. This procedure allows the cell sheet to be stably attached to the site of interest.

Another embodiment of the present invention provides a method for producing a transplantation material, comprising a step of treating stem cells with at least one compound selected from the group consisting of compounds represented by formulae (1) and (2), a salt thereof, or a solvate of them. In addition, another embodiment of the present invention provides a production method comprising a step of performing treatment with a compound represented by formula (8), a salt thereof, or a solvate of them. A low-molecular-weight organic compound is used for this production method, thereby imparting better stability and safety than a protein preparation and/or a nucleic acid preparation. This makes it possible to efficiently produce the transplantation material.

This method for producing a transplantation material may include the step of: culturing mesenchymal stem cells in a medium comprising at least one compound selected from the group consisting of compounds represented by formulae (1) and (2), a salt thereof, or a solvate of them to differentiate the mesenchymal stem cells into hepatocytes. The method may also include the step of culturing mesenchymal stem cells in a medium comprising a compound represented by formula (8), a salt thereof, or a solvate of them to differentiate the mesenchymal stem cells into hepatocytes. Note that as used herein, the term "transplantation material" is not particularly limited but may include, for example, a cell sheet. In addition, the transplantation material may come with any support.

In addition, another embodiment of the present invention provides a method for producing a cell sheet for transplantation on a liver surface, comprising an induction step of treating mesenchymal stem cells with hexachlorophene, a derivative thereof, a salt of them, or a solvate of them to induce the mesenchymal stem cells into hepatocytes. The cell sheet as prepared using this production method can exert a remarkable effect of suppressing liver dysfunction when transplanted on a liver surface as demonstrated in the following Examples. Therefore, this production method is an excellent production method for producing a cell sheet for transplantation on a liver surface. Note that when a certain organic compound is taken as a starting material, a derivative means a compound modified in such a degree without large structural and characteristic modifications in the starting material by introduction of a functional group, oxidation, reduction, or replacement or addition of an atom, etc. For example, "Burger's Medicinal Chemistry And Drug Discovery, 5$^{th}$ Edition, Vol 1: Principles and Practice" can be referred to.

In addition, another embodiment of the present invention provides a method for producing a cell sheet for transplantation on a liver surface, comprising an induction step of treating mesenchymal stem cells with a Wnt/β-catenin signaling pathway inhibitor to induce the mesenchymal stem cells into hepatocytes. The cell sheet as prepared using this production method can exert a remarkable effect of suppressing liver dysfunction when transplanted on a liver surface as demonstrated in the following Examples. Therefore, this production method is an excellent production method for producing a cell sheet for transplantation on a liver surface.

As described above, the embodiments of the present invention have been illustrated. These embodiments are examples of the present invention. Accordingly, various configurations other than the above embodiments can be adopted. In addition, combinations among the above-described embodiments can also be employed.

EXAMPLES

Hereinafter, the present invention is further illustrated by referring to Examples. The present invention, however, is not limited to them.

Example 1

Synthesis of IC-2

(1) Synthesis of ICG-001

ICG-001 is an oligopeptide having a bicyclic f-turn mimetic structure in its backbone, and reportedly functions as a potent antagonist for transcriptional activation by a β-catenin/Tcf complex (Drug Discov. Today 2005, 10, 1467-1474). ICG-001 was synthesized and examined according to a research article (Tetrahedron 2007, 63, 12912-12916).

(Scheme 1) Synthesis of ICG-001

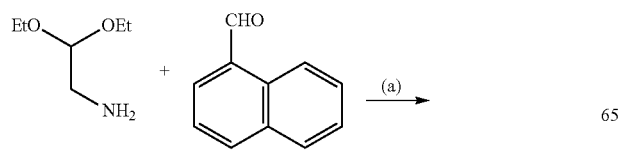

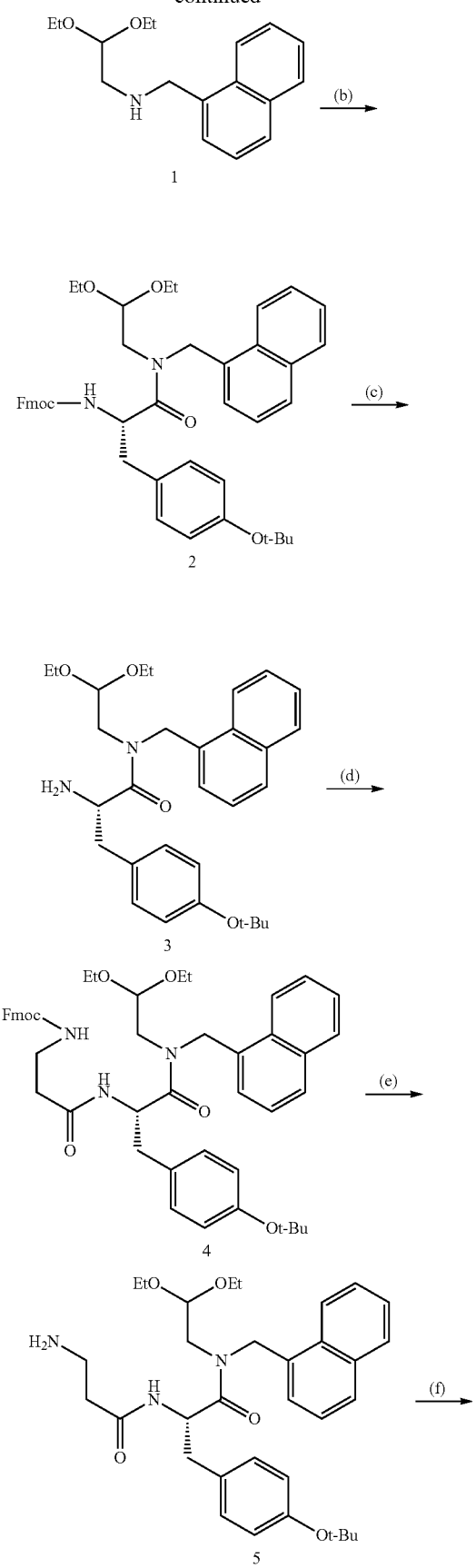

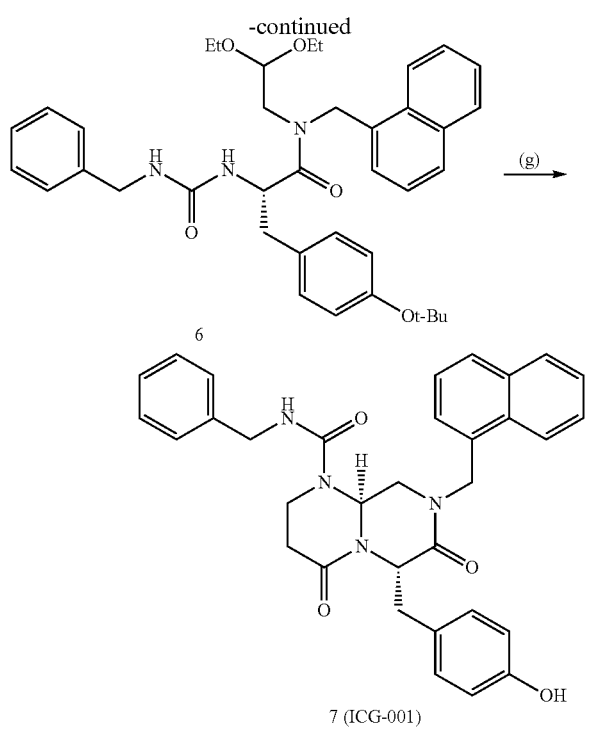

7 (ICG-001)

(a) NaBH₄, EtOH (b) Fmoc-L-Tyr(t-Bu)-OH, HATU, DIEA, DMF (c) DEA, CH₂Cl₂ (d) Fmoc-β-Ala-OH, HATU, DIEA, DMF (e) DEA, CH₂Cl₂ (f) BnNCO, CH₂Cl₂ (g) HCO₂H (1-1) Synthesis of Compound 1

1-naphthaldehyde (Wako Pure Chemical Industries, Ltd.) (1.56 g, 10 mmol) and 2,2-diethoxyethanamine (TOKYO CHEMICAL INDUSTRY CO., LTD.) (1.33 g, 10 mmol) were mixed and stirred at 100° C. for 20 min. After the mixture was cooled to room temperature, EtOH (20 mL) was used for dilution. NaBH₄ (0.38 g, 10 mmol) was added dropwise and the mixture was stirred at room temperature for 16 h. After completion of the reaction, EtOH was distilled away under reduced pressure. Then, a product was extracted with AcOEt. The resulting product was purified by silica gel column chromatography (hexane/AcOEt=5/1) to yield compound 1 (2.29 g, 8.5 mmol, 85%).

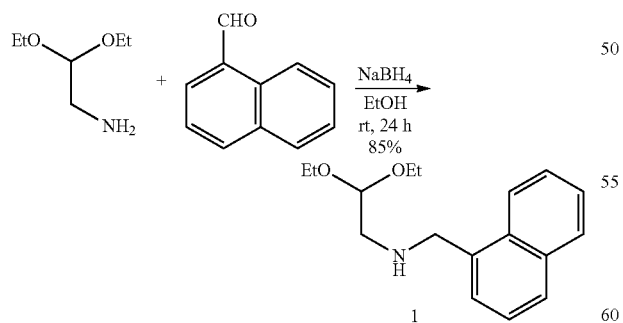

(1-2) Synthesis of Compound 3

A condensing agent HATU (0.76 g, 2.0 mmol) and diisopropylethylamine (DIEA)(0.35 mL, 2.0 mmol) were added to a DMF (7 mL) solution containing Fmoc-L-Tyr(t-Bu)-OH (0.87 g, 1.9 mmol). Next, the mixture was stirred for 20 min. Then, compound 1 (0.54 g, 2.0 mmol) was added, and the mixture was stirred at room temperature for 16 h. After the reaction, DMF was distilled away under reduced pressure. The resulting product was purified by column chromatography (hexane/AcOEt=10/1) to yield compound 2 (1.33 g, 1.9 mmol, 93%). The resulting compound 2 (1.33 g, 1.9 mmol) was dissolved in CH₂Cl₂ (20 mL). Subsequently, diethylamine (DEA) (10 ml, excess) was added, and the mixture was stirred at room temperature for 2 h. After the termination of the reaction was verified by TLC, CH₂Cl₂ was distilled away under reduced pressure. The resulting product was purified by silica gel column chromatography (AcOEt) to yield compound 3 (0.92 g, 1.8 mmol, 92%).

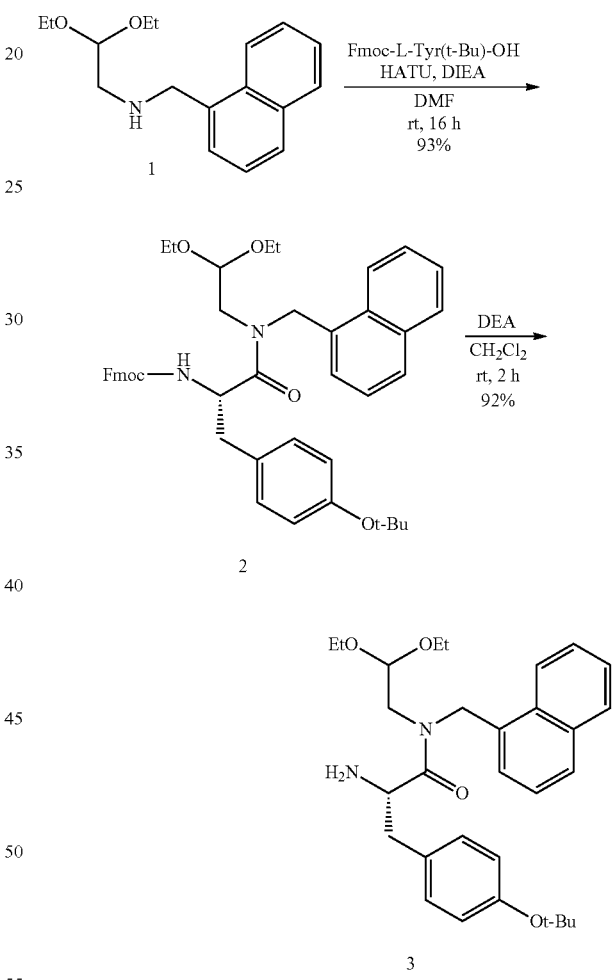

(1-3) Synthesis of Compound 5

A condensing agent HATU (0.70 g, 1.8 mmol) and diisopropylethylamine (DIEA)(0.32 mL, 1.8 mmol) were added to a DMF (8 mL) solution containing Fmoc-β-Ala-OH (0.53 g, 1.7 mmol). Next, the mixture was stirred for 20 min. Then, compound 3 (0.92 g, 1.8 mmol) was added, and the mixture was stirred at room temperature for 14 h. After the reaction, DMF was distilled away under reduced pressure. The resulting product was purified by column chromatography (hexane/AcOEt=1/1) to yield compound 4 (1.2 g, 1.5 mmol, 82%). The resulting compound 4 (1.2 g, 1.5 mmol) was dissolved in CH$_2$Cl$_2$ (20 mL). Subsequently, diethylamine (DEA) (9 mL, excess) was added, and the mixture was stirred at room temperature for 1 h. After the termination of the reaction was verified by TLC, CH$_2$Cl$_2$ was distilled away under reduced pressure. The resulting product was purified by silica gel column chromatography (AcOEt/EtOH=1/1) to yield compound 5 (0.66 g, 1.2 mmol, 80%).

resulting compound 6 (0.59 g, 0.85 mmol) was dissolved in formic acid (9 ml), and the mixture was stirred at room temperature for 20 h. Then, formic acid was distilled away under reduced pressure. The resulting product was purified by column chromatography (AcOEt) to yield compound 7a (ICG-001) as a white solid (0.26 g, 0.48 mmol, 57%). The resulting product was identified using MS spectrum and $^1$H NMR spectrum (having identical values in a literature)(FIG. 1).

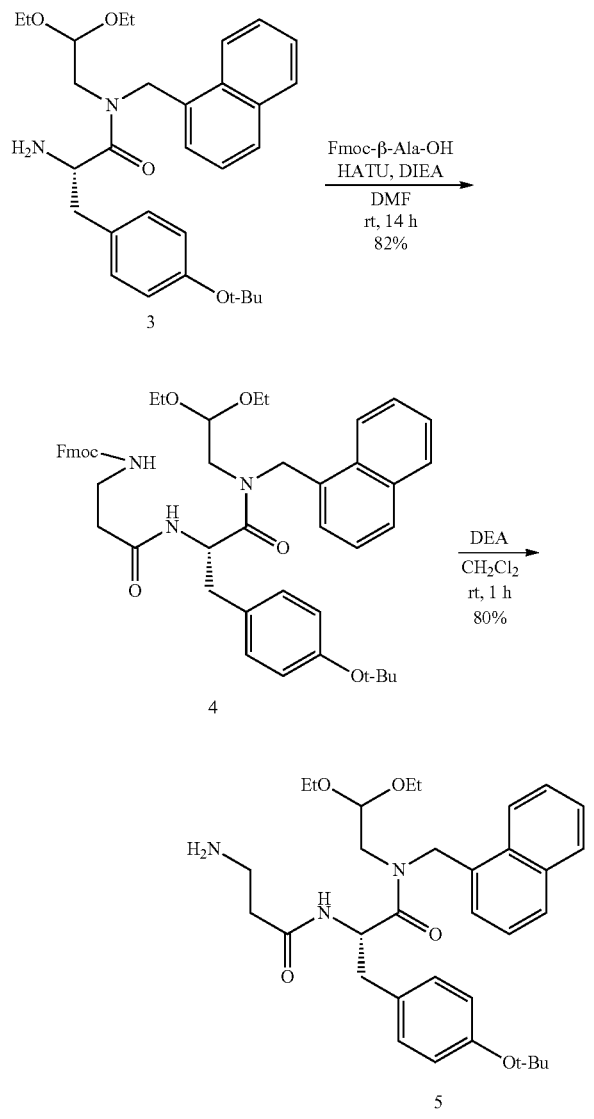

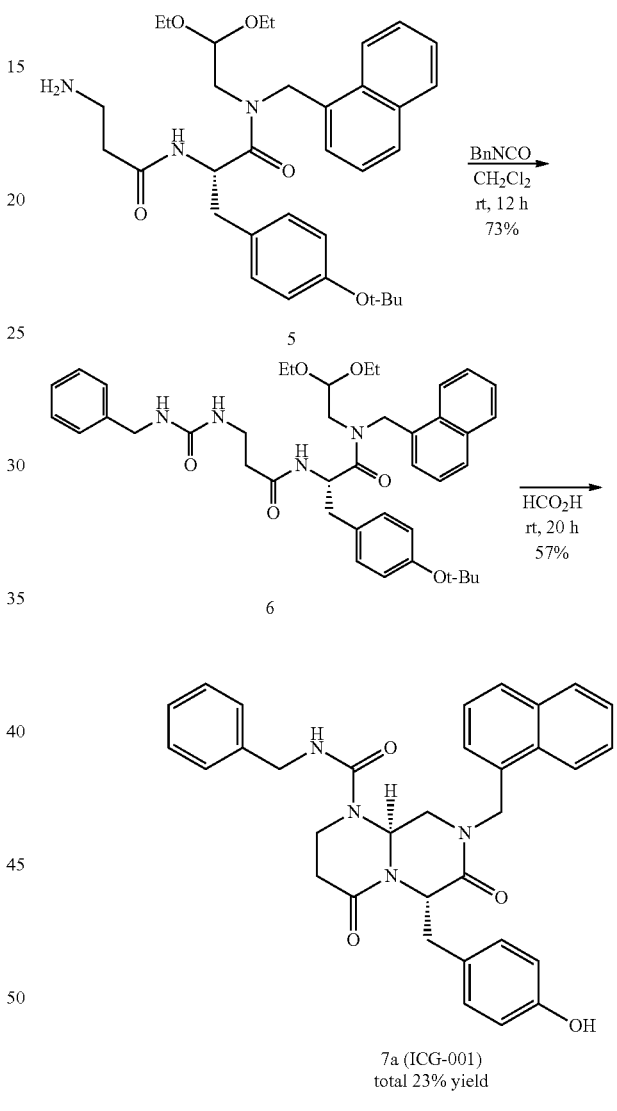

(1-4) Synthesis of Compound 7

A CH$_2$Cl$_2$ solution (8 mL) containing benzylisocyanate (0.16 g, 1.2 mmol) was added to a CH$_2$Cl$_2$ solution (8 mL) containing compound 5 (0.66 g, 1.2 mmol), and the mixture was stirred at room temperature for 12 h. After the termination of the reaction was verified by TLC, CH$_2$Cl$_2$ was distilled away under reduced pressure. The resulting product was purified by column chromatography (AcOEt/EtOH=1/1) to yield compound 6 (0.59 g, 0.85 mmol, 73%). The (2) Synthesis of IC-2

Figure 2:
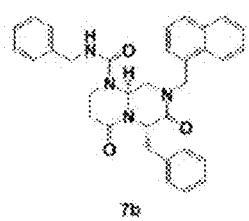
FIG. 2 shows spectrum data of IC-2 described in Examples.

When compound 3 described in the above section (1-2) was synthesized, synthesis was carried out using "Fmoc-L-Phe(t-Bu)-OH" in place of "Fmoc-L-Tyr(t-Bu)-OH" during the synthesis process in the above section (1). By doing so, synthesized was a derivative, IC-2 ((6S,9aS)-6-phenyl-8-naphthalen-1-ylmethyl-4,7-dioxo-hexahydro-pyrazino[1,2-a]pyrimidine-1-carbocylic acid benzylamide)(total yield 29%) in which side chains of ICG-001 were modified. FIG. 2 shows spectral data.

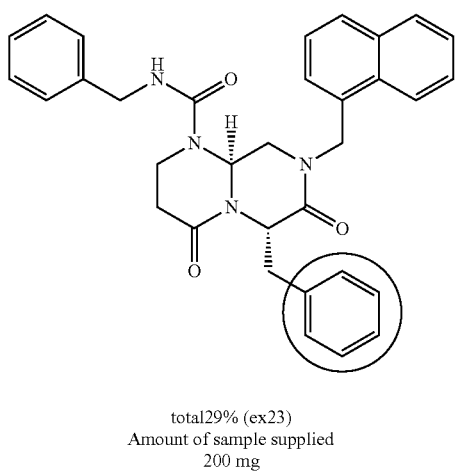

total29% (ex23)
Amount of sample supplied
200 mg

Example 2

Synthesis of HC-1

Hexachlorophene is a highly chlorinated phenolic compound used for an insect repellent, microbicide, disinfectant, etc. Here, synthesized was a derivative, in which a phenolic hydroxyl group of hexachlorophene was capped with a methyl group. MeI (1.0 mL, 16 mmol) and $K_2CO_3$ (5.3 g, 36 mmol) were added to an acetone solution (10 mL) containing hexachlorophene (TOKYO CHEMICAL INDUSTRY CO., LTD.)(417 mg, 1.0 mmol), and the mixture was stirred for 14 h. Next, excessive $K_2CO_3$ was removed, and the mixture was dried over $Na_2SO_4$. Then, the solvent was distilled away to yield a crude product. The resulting crude product was purified by column chromatography (hexane/AcOEt=7/1) to yield a hexachlorophene derivative of interest (a methyl ether compound) (bis(2,3,5-trichloro-6-methoxyphenyl)methane) (355 mg, 0.85 mmol, 85%). This methyl ether compound was analyzed by $^1$H NMR.

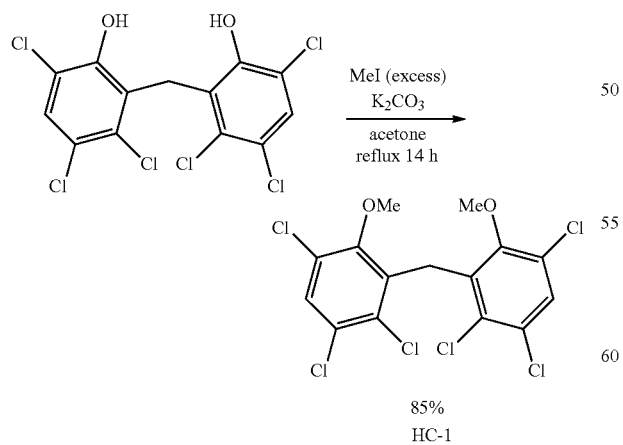

85%
HC-1
$^1$H NMR (400 MHz, acetone-$d_6$) δ = 3.71 (s, 2H), 4.54 (s, 2H), 7.65 (s, 1H).

Example 3

Synthesis of PN-3-4

Phenoxy benzhydrazide (Wako Pure Chemical Industries, Ltd.) (0.46 g, 2.0 mmol, 1.0 eq) was dissolved in EtOH. Next, 1-naphtaldehyde (0.32 g, 2.0 mmol, 1.0 eq) was added, and the mixture was stirred at room temperature for 22 h. After 22 h passed, the reaction solution was filtered and was then subjected to recrystallization with EtOH to yield a compound of interest (403 mg, 58%).

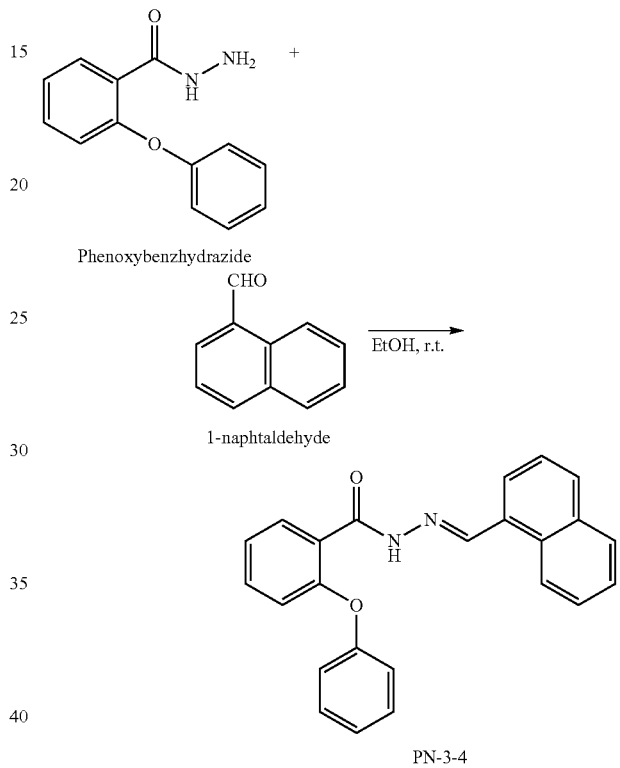

PN-3-4 (N'-[(E)-1-naphtylmethylidene]-2-phenoxybenzohydrazide) thus obtained was analyzed as follows:
$^1$H-NMR (400 MHz, $CDCl_3$)
6.83-8.78 (m, 16H, Ar—H) 8.82 (s, 1H, —CONHN=CHC), 10.79 (s, 1H, CONHN=CH) IR(KBr) 758, 1249, 1358, 1371, 1449, 1481, 1662, 2969, 3082 $cm^{-1}$;
MS (EI) Found: m/z 366. Calcd for $C_{24}H_{85}N_2O_2$: M+, Mol. Wt.: 366.41 Anal. Found: C, 78.37; H, 5.02; N, 7.68; O, 8.98%. Calcd for $C_{24}H_{15}N_2O_2$: C, 78.67; H, 4.95; N, 7.65; O, 8.73.

Example 4

PN-3-13 Synthesis

Synthesis was carried out using pentafluorobenzaldehyde (TOKYO CHEMICAL INDUSTRY CO., LTD.) in place of 1-naphtaldehyde in the above Example 3. Phenoxy benzhydrazide (0.24 g, 1.0 mmol, 1.0 eq) was dissolved in EtOH. Next, pentafluorobenzaldehyde (196 g, 1.0 mmol, 1.0 eq) was added, and the mixture was stirred at room temperature for 14 h. After 14 h passed, the reaction solution was filtered and was then subjected to recrystallization with EtOH to yield a compound of interest (287 mg, 71%).

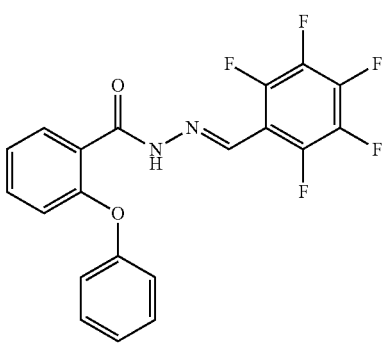 [SMILES: O=C(N/N=C/c1c(F)c(F)c(F)c(F)c1F)c1ccccc1Oc1ccccc1]

PN-3-13 (N'-[(E)-pentafluorophenylmethylidene]-2-phenoxybenzohydrazide) thus obtained was analyzed as follows:

1H-NMR (400 MHz, CDCl$_3$)
6.79-8.37 (m, 9H, Ar—H) 8.53 (s, 1H, —CONHN=CH—C), 10.92 (s, 1H, CONHN=CH) IR(KBr) 750, 980, 1231, 1493, 1518, 1659, 3285 cm$^{-1}$;
MS (EI) Found: m/z 406. Calcd for: $C_{20}H_{11}F_5N_2O_2$ M Mol. Wt.: 406.31

Example 5

PN-1-2 Synthesis

Synthesis was carried out using 3-phenoxy benzhydrazide (Wako Pure Chemical Industries, Ltd.) in place of 1-naphtaldehyde in the above Example 3. 3-Phenoxy benzhydrazide (0.78 g, 3.4 mmol, 1.0 eq) was dissolved in EtOH. Next, 5-methyl-furfural (0.43 g, 3.4 mmol, 1.0 eq) was added, and the mixture was stirred at room temperature for 14 h. After 14 h passed, the reaction solution was filtered and was then subjected to recrystallization with EtOH to yield a compound of interest (318 mg, 29%).

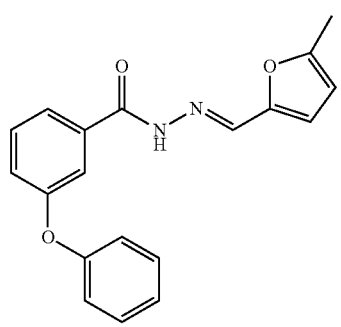 [SMILES: Cc1ccc(/C=N/NC(=O)c2cccc(Oc3ccccc3)c2)o1]

PN-1-2 (N'-[(E)-(5-methyl-2-fulyl)methylidene]-3-phenoxybenzohydrazide) thus obtained was analyzed as follows:

$^1$H-NMR (400 MHz, CDCl$_3$)
2.35 {s, 3H, —CH=C(CH$_3$)} 6.11{s, 1H, —CHC(CH$_3$)} 6.69 {s, 1H, —CHCHC(CH$_3$)} 7.03-7.52 (m, 9H, Ar—H) 8.48 (s, 1H, —CONHN=CH—), 8.92 (s, 1H, CONHN=CH) IR(KBr) 746, 1018, 1233, 1287, 1300, 1489, 1580, 1651, 3048, 3194 cm$^{-1}$;
MS (EI) Found: m/z 320. Calcd for $C_{19}H_{16}N_2O_3$: M, Mol. Wt.: 320.34.
Anal. Found: C, 71.25; H, 5.04; N, 8.79; O, 14.92%.
Calcd for: $C_{19}H_{16}N_2O_3$ C, 71.24; H, 5.03; N, 8.74; O, 14.98.

Example 6

Figure 3:
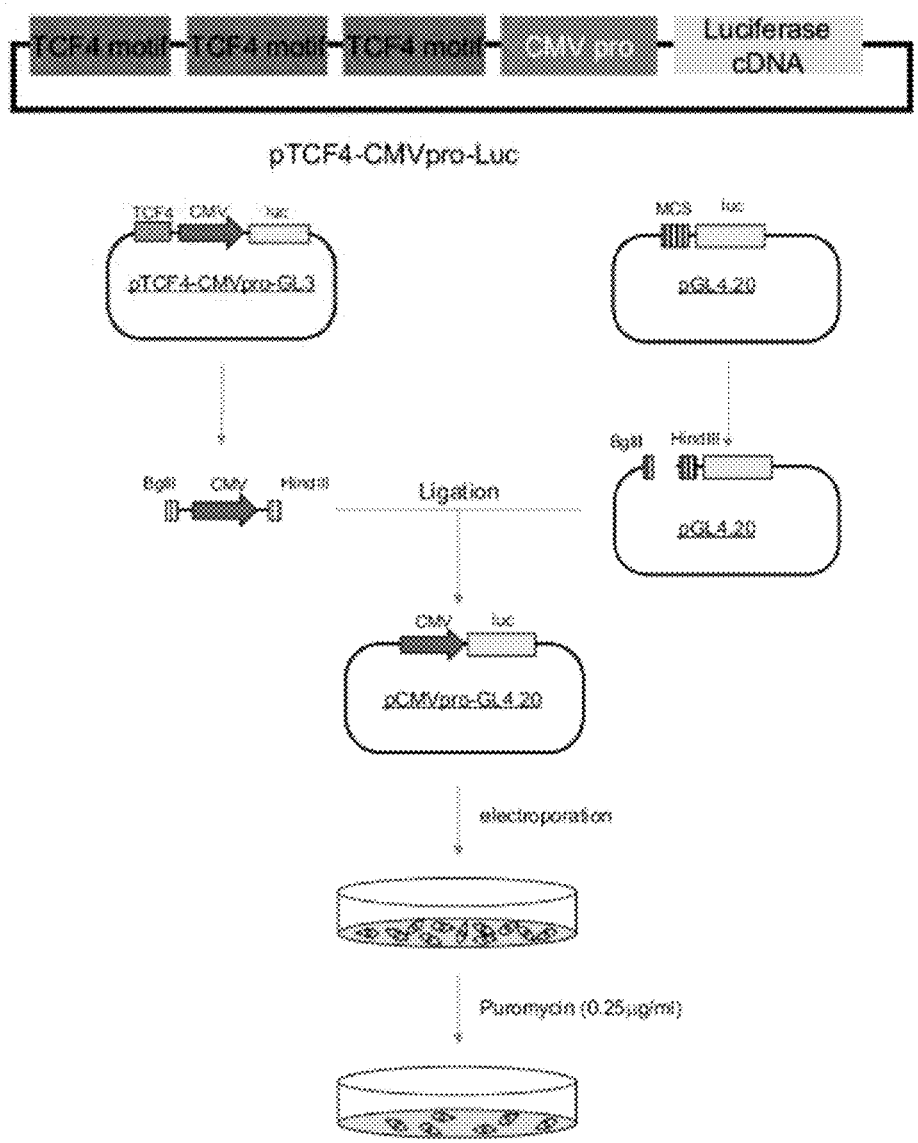
FIG. 3 is a schematic diagram illustrating how to establish a human mesenchymal stem cell stably expressing a β-catenin/TCF4/luciferase reporter gene.
Figure 4:
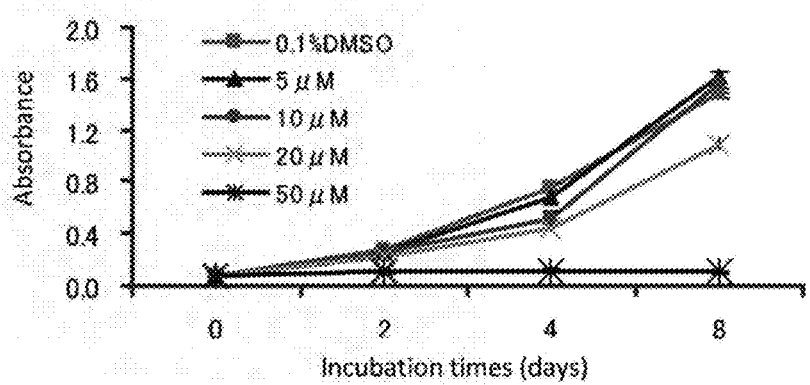
FIG. 4 is a graph illustrating the results of examining the proliferation potential of bone-marrow-derived cells (UE7T-13 cells) when treated with IC-2.
Figure 5:
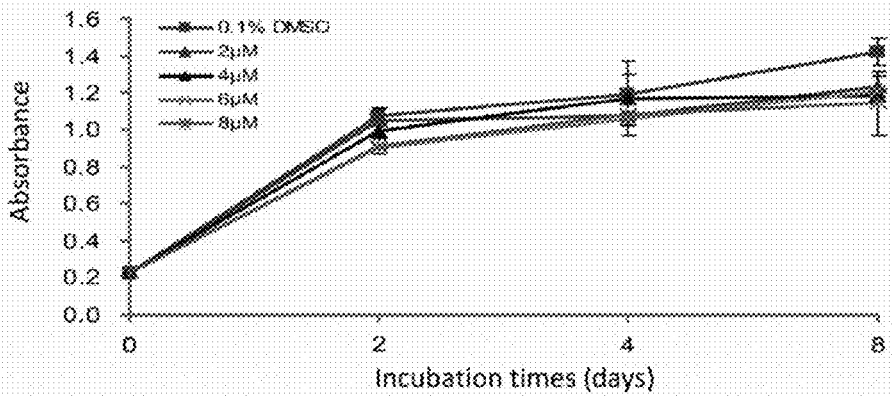
FIG. 5 is a graph illustrating the results of examining the proliferation potential of bone-marrow-derived cells (UE7T-13 cells) when treated with HC-1.
Figure 6:
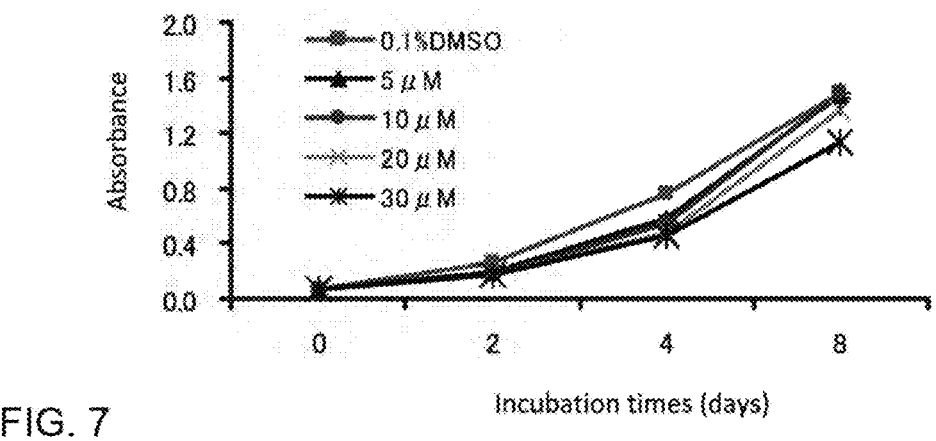
FIG. 6 is a graph illustrating the results of examining the proliferation potential of bone-marrow-derived cells (UE7T-13 cells) when treated with PN-3-4.
Figure 7:
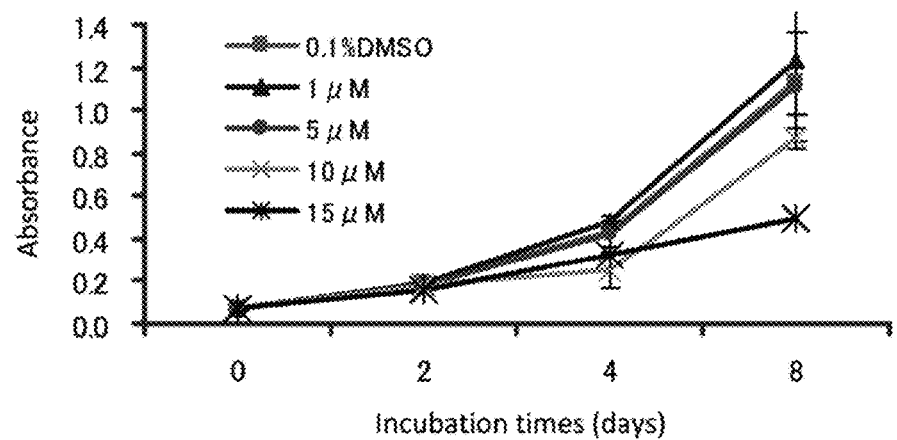
FIG. 7 is a graph illustrating the results of examining the proliferation potential of bone-marrow-derived cells (UE7T-13 cells) when treated with PN-3-13.
Figure 8:
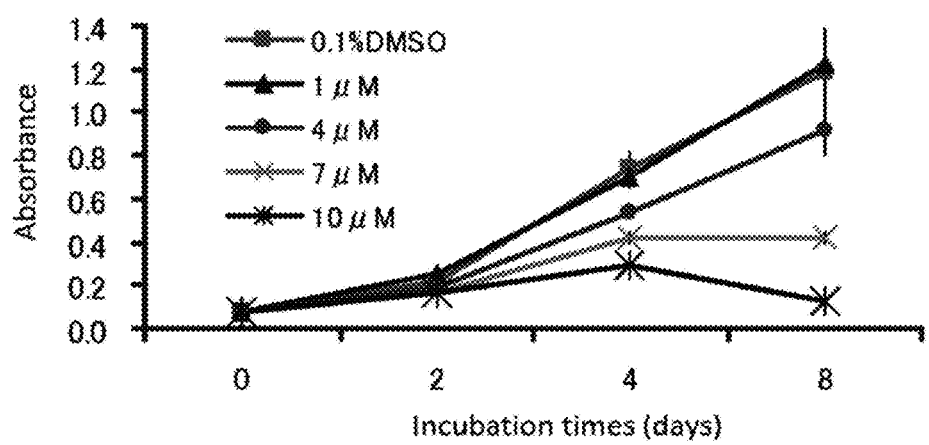
FIG. 8 is a graph illustrating the results of examining the proliferation potential of bone-marrow-derived cells (UE7T-13 cells) when treated with PN-1-2.

Establishment of Cell Line (UE7T-13) Having Vector Stably Expressing Luciferase FIG. 3 is a schematic diagram illustrating how to establish a human mesenchymal stem cell stably expressing a β-catenin/TCF4/luciferase reporter gene. FIG. 3 illustrates how to construct pTCF4-CMVpro-GL4.20 plasmid by using a luciferase expression vector. The pTCF4-CMVpro-GL4.20 plasmid contains three TCF4 sequences CCTTGATC upstream of a CMV promoter to express luciferase. In addition, pCMVpro-GL4.20 plasmid was constructed as a control. The resulting plasmids were each linearized, introduced into UE7T-13 by electroporation, and selected using puromycin (0.25 µg/ml) supplemented in a medium. Puromycin-resistant cells were cloned and used for a luciferase assay.

Example 7

Examples of Test for IC-2, etc.

Bone marrow-derived cells (UE7T-13 cells) were treated with IC-2, etc. Then, the following points were examined: (1) Proliferation Potential (Toxicity); (2) Ability of Inhibiting Wnt/β-Catenin Pathway; and (3) Ability of Differentiating into Hepatocytes.

(1) Examination of Proliferation Potential (Toxicity) (MTT Assay (UE7T-13))

A human mesenchymal stem cell line, UE7T-13, was seeded on a 96-well plate (with a bottom area of 0.3 cm$^2$) at a cell density of 9.0×10$^3$ cells/cm$^2$, and was cultured in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 µg/ml streptomycin (Nacalai Tesque). This time point was set to day 0. At the next day (day 1), the medium was changed to DMEM containing IC-2, etc. After that, at days 2, 4, 8, Tetra Color One (SEIKAGAKU CORPORATION) was used for measurement, and whether or not the compound affected the proliferation of UE7T-13 cells was investigated. DMSO contained in the culture medium had a final concentration of 0.1%.

FIGS. 4 to 8 show the results of treating bone marrow-derived cells (UE7T-13 cells) with IC-2, etc. Treatment with IC-2, etc., somewhat inhibited the proliferation of the bone marrow-derived cells (UE7T-13 cells) in some cases. However, the proliferation potential by itself remained (except at days 2, 4, and 8 with 50 µM IC-2 and day 8 with 10 µM PN-1-2). That is, IC-2, etc., had sufficiently low cell toxicity toward the bone marrow-derived cells (UE7T-13 cells), so that the compounds can be definitely used as a differentiation inducer. The results, in particular, demonstrated very low cell toxicity toward the bone marrow-derived cells (UE7T-13 cells) when IC-2 of 20 µM or less, HC-1 of 8 µM or less, PN-3-4 of 30 µM or less, PN-3-13 of 10 µM or less, or PN-1-2 of 40 µM or less was used.

(2) Examination of Ability of Inhibiting Wnt/O-Catenin Pathway (Luciferase Assay (UE7T-13))

The cell line having a vector stably expressing luciferase was seeded on a 24-well plate, and was cultured at 37° C. At the next day, the medium was changed to a medium containing IC-2, etc., and the cell line was further cultured at 37° C. After that, at days 1, 4, and 8, a luciferase assay system (Promega) was used and the luciferase activity was read with a fluorescence plate reader (ARVO) at a wavelength of 556 nm.

Figure 9:
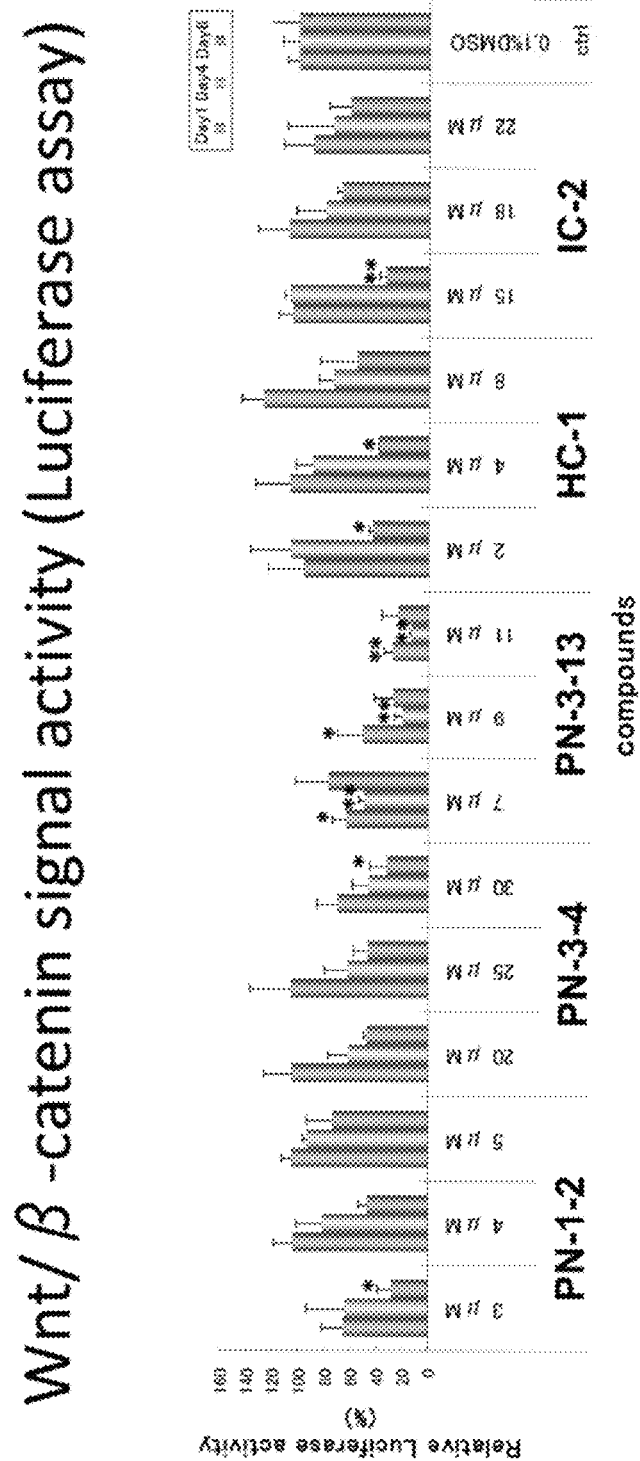
FIG. 9 is a graph illustrating how IC-2, etc., affects Wnt/β-catenin activity.

According to a reporter assay using the pTCF4-CMV-luciferase plasmid, the results demonstrated that treatment of the bone marrow-derived cells (UE7T-13 cells) with IC-2 of 15 μM or higher significantly inhibited the Wnt/β-catenin signaling pathway at 8 days after the treatment (FIG. 9). In addition, the results demonstrated that treatment of the bone marrow-derived cells (UE7T-13 cells) with HC-1 of 2 μM or higher significantly inhibited the Wnt/β-catenin signaling pathway at 8 days after the treatment. Further, the results demonstrated that treatment of the bone marrow-derived cells (UE7T-13 cells) with PN-3-4 of 20 μM or higher significantly inhibited the Wnt/β-catenin signaling pathway at 8 days after the treatment. Furthermore, the results demonstrated that treatment of the bone marrow-derived cells (UE7T-13 cells) with PN-3-13 of 9 μM or higher significantly inhibited the Wnt/β-catenin signaling pathway at 8 days after the treatment. Moreover, the results demonstrated that treatment of the bone marrow-derived cells (UE7T-13 cells) with PN-1-2 of 3 μM or higher significantly inhibited the Wnt/β-catenin signaling pathway at 8 days after the treatment.

(3) Examination of Ability of Differentiating into Hepatocytes (3-1) Differentiation Induction (UE7T-13)

The cells were plated on a 6-well plate at a cell density of $9.0 \times 10^3$ cells/cm$^2$, and were cultured at 37° C. for 24 h. After 24 h, the medium was changed to a medium containing IC-2, etc. After that, the medium was changed twice a week, and the cells were subcultured once a week to adjust a cell number at $9.0 \times 10^3$ cells/cm$^2$. Total RNA was collected at days 8, 16, and 24 after the initiation of the induction.

(3-2) Reverse Transcription-Polymerase Chain Reaction (UE7T-13)

Total RNA was extracted with a TRIzol reagent. After the extraction, in order to completely remove DNA, deoxyribonuclease was added and the mixture was incubated at 37° C. for 1 h. A SuperScript First-Stand Synthesis System for RT-PCR (Invitrogen) was used for reverse transcription, and an oligo dT primer was used to convert 1 μg of RNA into cDNA. To perform a PCR, the cDNA was diluted by 5 times and 1 μl of the cDNA was used. A recombinant Taq DNA polymerase (Invitrogen) was used for the PCR. With regard to primers for human albumin, 5'-TTGGAAAAATC-CCACTGCAT-3' (SEQ ID NO: 1) and 5'-CTCCAAGCT-GCTCAAAAAGC-3' (SEQ ID NO: 2) were used. The PCR involved 1 cycle of 95° C. for 2 min and 35 cycles of 95° C. for 30 sec, 58° C. for 30 sec, and 72° C. for 30 sec. Human glyceraldehyde 3-phosphate dehydrogenase (GAPDH) was used as an internal control. With regard to GAPDH primers, 5'-GTCTTCTCCACCATGGAGAAGGCT-3' (SEQ ID NO: 3) and 5'-CATGCCAGTGAGCTFCCCGTTCA-3' (SEQ ID NO: 4) were used. The PCR involved 1 cycle of 95° C. for 2 min and 20 cycles of 95° C. for 30 sec, 60° C. for 30 sec, and 72° C. for 30 sec. The PCR products were subjected to electrophoresis for 30 min in a 2% agarose gel containing ethidium bromide, and their gel images were taken with a transilluminator.

FIGS. 10 and 11 are electrophoresis gel images illustrating differentiation induction into hepatocytes by using IC-2, etc. Treatment with any of IC-2, etc., apparently increased levels of expression of albumin, which is a representative marker for differentiation into hepatocytes, compared to those of a control. The levels of the albumin expression were particularly high when the cells were treated with 15 μM IC-2. Note that GAPDH was an internal control and the amount of RNA used was the same as that used for the test substance. Huh-7 is a human hepatoma cell line. PNU-74654 (N-[(5-methyl-2-furyl)methylideneamino]-2-phe-noxy-benzamide) is a low-molecular-weight compound that reportedly inhibits a Wnt/β-catenin pathway by blocking the interaction between β-catenin and TCF.

(3-3) Urea Assay (UE7T-13)

The cells were plated on a 24-well plate, and were cultured in a medium containing IC-2, etc. Ammonium chloride (at a final concentration of 5 mM) was added to the medium, and the cells were cultured for 48, 72, and 96 h. Then, an amount of urea in the medium was determined using a QuantiChrom Urea Assay Kit (BioAssay Systems) and a fluorescence plate reader (TECAN) at a wavelength of 520 nm.

Figure 12:
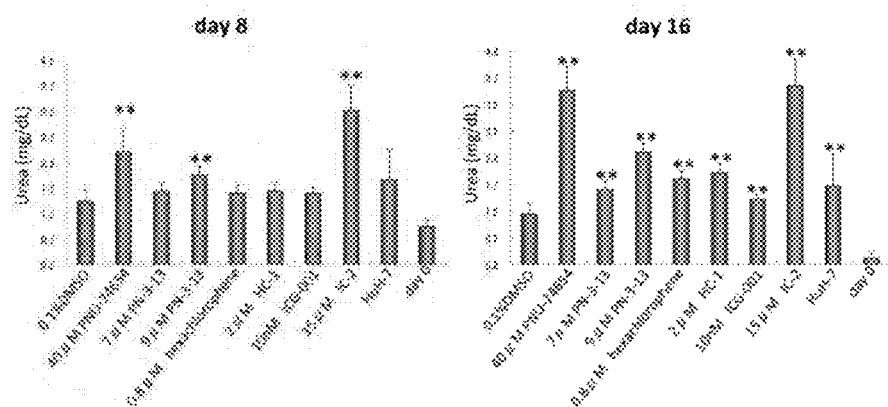
FIG. 12 is graphs illustrating an ability of urea synthesis (at days 8 and 16) of samples differentiated using IC-2, etc.

FIG. 12 is graphs illustrating the ability of urea synthesis (at days 8 and 16) of samples differentiated using IC-2, etc. The ability of inducing differentiation into hepatocytes (measurement of the ability of urea synthesis) by IC-2, etc., was determined at day 8. As a result, any of the compounds apparently increased cellular urea synthesis compared with that of a negative control (0.1% DMSO). The levels increased by the same amount or more compared to those of a positive control (Huh-7).

In addition, the ability of inducing differentiation into hepatocytes (measurement of the ability of urea synthesis) by IC-2, etc., was determined at day 16. As a result, any of the compounds apparently increased cellular urea synthesis compared with that of a negative control (0.1% DMSO). Further, the levels increased by the same amount or more compared to those of a positive control (Huh-7). Treatment with IC-2, in particular, remarkably increased the urea synthesis. The above results indicate that the cells treated with IC-2, etc., not only just express hepatocyte markers but also exert potentials as functional hepatocytes.

(3-4) Periodic Acid-Schiff (PAS) Staining (UE7T-13) A cover glass (22×22 mm, MATSUNAMI) was sterilized with 70% EtOH and placed in a 6-well plate. Next, cells were seeded on the cover glass and cultured in a medium containing IC-2, etc. At 8, 16, and 24 days after the initiation of the culture, the cells were washed twice with PBS. Then, the cells were treated with 4% paraformaldehyde/PBS for 20 min and fixed onto the cover glass. As a negative control, 10 mg/ml of α-amylase (10 mg/ml; in 0.1 M phosphate buffer solution at pH 6.8) was added, and the cells were incubated therewith at 37° C. for 1 h to digest their glycogen. Subsequently, 1% aqueous periodic acid was used for oxidation treatment for 10 min. After that, the cells were treated with a Schiff reagent for 15 min to stain glycogen. Then, the cells were washed three times with aqueous sulfurous acid and were washed three times with distilled water. After their nuclei were stained with Mayer's hematoxylin, 50% glycerol diluted with PBS was used to mount the cover glass. Finally, the cells were observed under a light microscope. The cells which had been cultured with 0.1% DMSO were used as a control.

Figure 13:
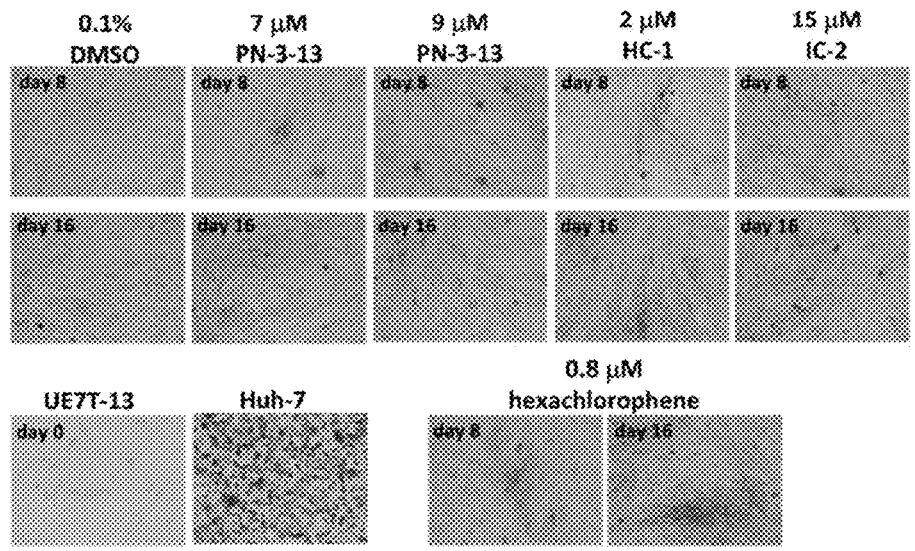
FIG. 13 is photomicrographs (PAS staining) illustrating an ability of inducing differentiation into hepatocytes by using IC-2, etc.

FIG. 13 is photomicrographs (PAS staining) illustrating an ability of inducing differentiation into hepatocytes by using IC-2, etc. An ability of inducing differentiation into hepatocytes by using IC-2, etc., was examined (PAS staining). As a result, intracellular glycogen accumulation apparently increased compared with a negative control (0.1% DMSO), and was substantially the same level as that of a positive control (Huh-7, a hepatoma cell).

In addition to IC-2, etc., another compound for inhibiting the Wnt/β-catenin signaling pathway was also synthesized.

With regard to this compound, ICG-001, and PNU-74654, the ability of inducing differentiation into hepatocytes was evaluated using PAS staining in a manner similar to the above. As a result, in all the cases of using any of the compounds, the intracellular glycogen accumulation did not increase compared to the negative control. In view of the above, the reason why the differentiation of mesenchymal stem cells into hepatocytes in this Example was successful was because IC-2, etc., has a particular structure.

(3-5) Immunocytochemistry (UE7T-13)

A cover glass (22×22 mm, MATSUNAMI) was sterilized with 70% EtOH and placed in a 6-well plate. Next, cells were seeded on the cover glass and cultured in a medium containing IC-2, etc. At 8, 16, and 14 days after the initiation of the culture, the cells were washed twice with PBS. Then, the cells were treated with 4% paraformaldehyde/PBS for 20 min and fixed onto the cover glass. After that, the cells were permeated with 0.2% Triton X-100 for 10 min. Subsequently, the cells were blocked with 3% BSA/PBS for 30 min. An anti-albumin antibody, anti-C/EBP antibody, anti-AFP antibody, or anti-CYP1A1 antibody was used as a primary antibody, and the cells were incubated therewith at 4° C. overnight. Next, an Alexa Fluoro 488 goat anti-mouse antibody or Alexa Fluoro 594 goat anti-rabbit antibody was used as a secondary antibody, and the cells were incubated therewith at room temperature for 1 h. DAPI was used for nuclear staining. Thereafter, 50% glycerol diluted with PBS was used to mount the cover glass. Finally, the cells were observed under a confocal laser microscope. The cells which had been cultured with 0.1% DMSO were used as a control.

Figure 14:
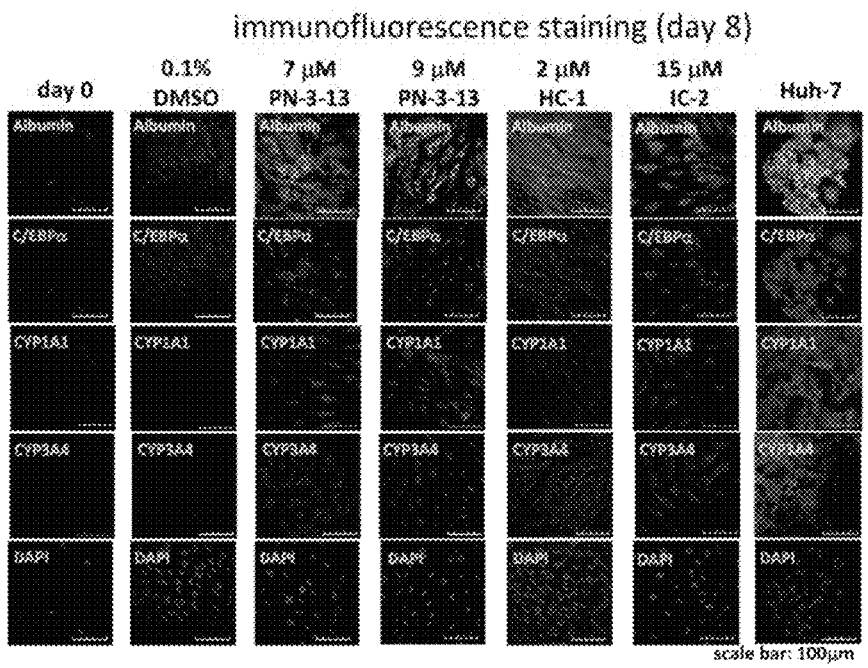
FIG. 14 is fluorescent photomicrographs illustrating hepatocyte differentiation induction (at day 8) using IC-2, etc.
Figure 15:
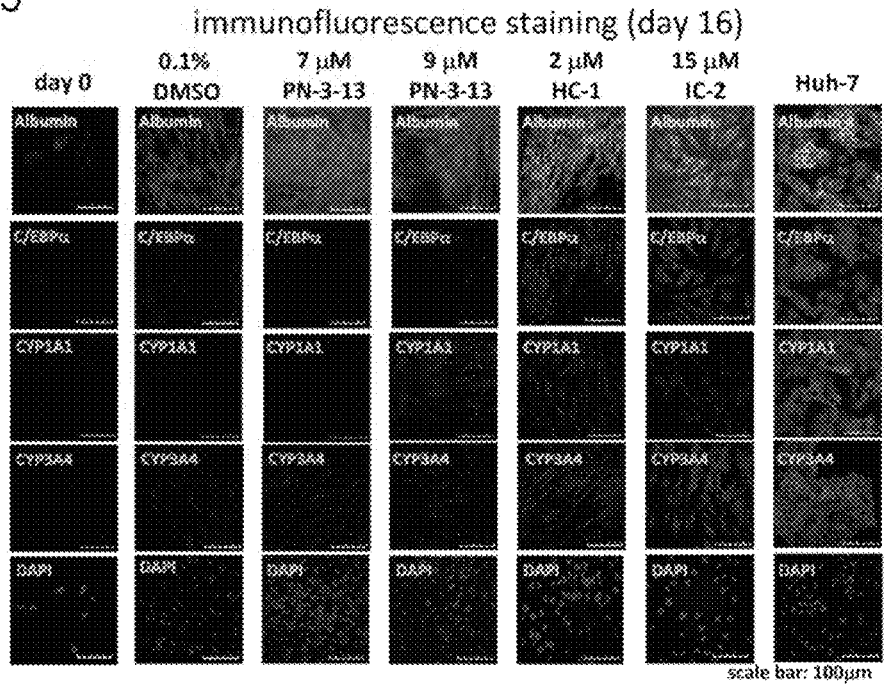
FIG. 15 is fluorescent photomicrographs illustrating hepatocyte differentiation induction (at day 16) using IC-2, etc.

FIG. 14 is fluorescent photomicrographs illustrating differentiation induction into hepatocytes (at day 8) by using IC-2, etc. Hepatocyte differentiation was induced by IC-2, etc. As a result, at day 8 after the treatment with IC-2, etc., levels of expression of markers such as albumin, C/EBPα, CYP1A1, and CYP3A4, which are representative markers for differentiation into hepatocytes, apparently increased compared with those of a negative control (0.1% DMSO). The levels are equivalent to those of a positive control (Huh-7). FIG. 15 is fluorescent photomicrographs illustrating differentiation induction into hepatocytes (at day 16) by using IC-2, etc. Similar results were obtained at day 16 after the treatment with IC-2, etc. Treatment with IC-2, in particular, remarkably increased the levels of expression of the markers. Note that DAPI was used as a control for each staining, and their fluorescent photomicrographs are shown.

<Discussion of Results>

In view of the above experimental results, the present inventors have revealed that IC-2, etc., can be used to differentiate mesenchymal stem cells into functional hepatocytes. At the same time, they have elucidated that the mesenchymal stem cells are useful as a cell source for liver regenerative medicine so as to realize liver regenerative medicine. Also, in order to induce the differentiation, the inhibition of the Wnt/β-catenin signaling pathway by IC-2, etc., was effective. These findings are important so as to develop genuinely clinically applicable liver regenerative medicine.

Example 8

Evaluation of Levels of Expression of Genes Encoding Liver-specific Secretory Proteins and Cytokines Bone marrow-derived mesenchymal stem cells (UE7T-13 cells) were treated with a compound, hexachlorophene (H4625-25G; Sigma-Aldrich, Inc.) or IC-2. At that time, gene expression of each of liver-specific secretory proteins and cytokines was evaluated. First, bone marrow-derived mesenchymal stem cells (UE7T-13 cells) were seeded on a 6-well plate (with a bottom area of 9.6 cm$^2$) at a cell density of $9.0 \times 10^3$ cells/cm$^2$, and were cultured under conditions at 37° C. and 5% $CO_2$ in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 μg/ml streptomycin (Nacalai Tesque). This time point was set to day 0.

At the next day corresponding to day 1, the medium was changed to DMEM containing hexachlorophene at a final concentration of 0.8 μM or IC-2 at a final concentration of 15 μM. At day 4, the medium was changed, and at day 8, the cells were reseeded and subcultured at a cell density of $9.0 \times 10^3$ cells/cm$^2$. After that, the medium was replaced twice during 8 days, and the cells were subcultured every 8 days. Then, the similar operation was carried out until day 24. At days 8, 16, and 24 after the initiation of the induction, TRIzol (Invitrogen) was used to extract total RNA according to the attached instruction. After the extraction, deoxyribonuclease (Nippon Gene) was added, and the mixture was incubated at 37° C. for 30 min to remove DNA. In a reverse transcription reaction, SuperScriptII Reverse Transcriptase (Invitrogen) and Oligo(dT)$_{15}$ primer were added to 1 μg of RNA to convert it into cDNA. In a RT-PCR method, the cDNA was diluted by 5 times. Next, 1 μl of the cDNA was used as a template. Then, rTaq DNA polymerase (TOYOBO) was used to amplify the cDNA. MQ water was used as a negative control. cDNA from Huh-7 or UE7T-13 cells was used as a positive control.

Sequences of primers used in a PCR for detecting expression of genes encoding human liver-specific secretory proteins are each described as follows: primers for albumin were 5'-TTGGAAAAATCCCACTGCAT-3' (SEQ ID NO: 1) and 5'-CTCCAAGCTGCTCAAAAAGC-3' (SEQ ID NO: 2); primers for a1-antitrypsin were 5'-CAAGGAGCTTGACAGAGACACAGTTTTT-3' (SEQ ID NO: 5) and 5'-GTGTCCTTGACTTCAAAGGGTCTCT-3' (SEQ ID NO: 6); primers for ceruloplasmin were 5'-CGACTTGGGATTATGCCTCTGACC-3' (SEQ ID NO: 7) and 5'-CCCAATTCTATCTGGGCCATTTTTGA-3' (SEQ ID NO: 8); primers for transthyretin were 5'-AAGGCACTTG-GCATCTCCCCA-3' (SEQ ID NO: 9) and 5'-CAGGGCG-GCAATGGTGTAGC-3' (SEQ ID NO: 10); primers for apolipoprotein E were 5'-GTCCTTCCCCAGGAGCCGAC-3' (SEQ ID NO: 11) and 5'-GTCTCCACCGCTTGCTC-CAC-3' (SEQ ID NO: 12); primers for apolipoprotein B were 5'-GCTTCAAGCCCATCCGCACA-3' (SEQ ID NO: 13) and 5'-TGACAGGACTGGCTGCTGCT-3' (SEQ ID NO: 14); primers for complement C3 were 5'-CAGCAC-CATGGGACCCACCTCAG-3' (SEQ ID NO: 15) and 5'-CTCTCCAGCCGCAAGATGTTGGG-3' (SEQ ID NO: 16); primers for complement C4 were 5'-ACTTTGAGAC-CGAGGGGCCC-3' (SEQ ID NO: 17) and 5'-GGCACTTC-CTGCACAGCCTC-3' (SEQ ID NO: 18); primers for retinol-binding protein 4 were 5'-CCCAGAAGCGCAGAAGATT-3' (SEQ ID NO: 19) and 5'-AAGGTTTCTTTCTGATCTGCCAT-3' (SEQ ID NO: 20); primers for retinol-binding protein 5 were 5'-CTTT-GTGGCCAACTGGCTC-3' (SEQ ID NO: 21) and 5'-GCT-TCAGCAAGTTGGCGA-3' (SEQ ID NO: 22); primers for haptoglobin were 5'-TTCCAGAGGCAAGACCAACC-3' (SEQ ID NO: 23) and 5'-TGCCTGAGTCCACTGCAAA-3' (SEQ ID NO: 24); primers for α-fibrinogen were 5'-AG-GATTCTCATTCGTTGACCAC-3' (SEQ ID NO: 25) and 5'-TCTGACACTCGGTTGTAGGT-3' (SEQ ID NO: 26); primers for β-fibrinogen were 5'-AAAGTTAGAATCTGAT-GTCTCAGCTCAA-3' (SEQ ID NO: 27) and 5'-CTTTCCT-GATAATTTCCTCACATTCTTT-3' (SEQ ID NO: 28); and primers for GAPDH, an internal control, were 5'-AGCCA-CATCGCTCAGACAC-3' (SEQ ID NO: 29) and 5'-GC-CCAATACGACCAAATCC-3' (SEQ ID NO: 30).

The PCR involved 1 cycle of 94° C. for 2 min, followed by 35 cycles of 94° C. for 30 sec, a temperature corresponding to each primer for 30 sec, and 72° C. for 30 sec, and 1 cycle of 72° C. for 5 min. The temperature corresponding to each primer was 58° C. for albumin, 68° C. for complement C3, 60° C. for retinol-binding protein 4, 56° C. for retino-binding protein 1 and haptoglobin, or 64° C. for the rest.

Sequences of primers used in a PCR for detecting expression of genes encoding human cytokines are each described as follows: primers for interleukin 6 (IL6) were 5'-CCA-GAGCTGTGCAGATGAG-3' (SEQ ID NO: 31) and 5'-GTCAGCAGGCTGGCATTT-3' (SEQ ID NO: 32); primers for IL-1 receptor antagonist (IL1ra) were 5'-CAGCTG-GAGGCAGTTAACAT-3' (SEQ ID NO: 33) and 5'-CGC-CTTCGTCAGGCATATTG-3' (SEQ ID NO: 34); primers for hepatocyte growth factor (HGF) were 5'-CCCT-TCAATAGCATGTCAAGTGG-3' (SEQ ID NO: 35) and 5'-GTTCCCTTGTAGCTGCGT-3' (SEQ ID NO: 36); primers for vascular endothelial growth factor (VEGF) were 5'-TTGCCTTGCTGCTCTACCT-3' (SEQ ID NO: 37) and 5'-TCCATGAACTTCACCACTTCGT-3' (SEQ ID NO: 38); primers for transforming growth factor α (TGFα) were 5'-CTGAAGGGAAGAACCGCTTTG-3' (SEQ ID NO: 39) and 5'-AGCCTTCTTTATTGATCTGCCACA-3' (SEQ ID NO: 40); primers for transforming growth factor β (TGFβ) were 5'-CTGCGTCTGCTGAGGC-3' (SEQ ID NO: 41) and 5'-TCCACGGCTCAACCACTG-3' (SEQ ID NO: 42); primers for epidermal growth factor (EGF) were 5'-TGGGT-CAAGGCAAGAGAGAGTA-3' (SEQ ID NO: 43) and 5'-GATTCCTTCCTGTTGAITGACCA-3' (SEQ ID NO: 44); primers for basic fibroblast growth factor (bFGF) were 5'-GGGTCCGGGAGAAGAGC-3' (SEQ ID NO: 45) and 5'-GCCAGGTAACGGTTAGCAC-3' (SEQ ID NO: 46); primers for heparin-binding EGF-like growth factor (HB-EGF) were 5'-GGACCGGAAAGTCCGT-3' (SEQ ID NO: 47) and 5'-GCTCCTCCTTGTITTGGTGT-3' (SEQ ID NO: 48); primers for amphiregulin (AREG) were 5'-AAC-GAAAGAAACTTCGACAAGAGA-3' (SEQ ID NO: 49) and 5'-ATGATCCACTGGAAAGAGGACC-3' (SEQ ID NO: 50); primers for stem cell factor (SCF) were 5'-AGGGACAGTGGAGAGGG-3' (SEQ ID NO: 51) and 5'-GCAAGTGAGAATCCAAGTTGTGT-3' (SEQ ID NO: 52); primers for angiogenin were 5'-TTCCATTGTCCTGC-CCG-3' (SEQ ID NO: 53) and 5'-AAGTGTGTGTACCTG-GAGTTATC-3' (SEQ ID NO: 54); primers for angiopoietin were 5'-ATGTGCAAATGTGCCCTCA-3' (SEQ ID NO: 55) and 5'-TCGCTTCTGACATITGCGCT-3' (SEQ ID NO: 56); primers for tumor necrosis factor (TNFα) were 5'-CCCA-GGGACCTCTCTCTAATC-3' (SEQ ID NO: 57) and 5'-GGCCAGGAGGGCATTG-3' (SEQ ID NO: 58); primers for fas antigen (Fas) were 5'-GTTGGTGGACCCGCTCA-GTA-3' (SEQ ID NO: 59) and 5'-AACAGACGTAAGAAC-CAGAGGTAG-3' (SEQ ID NO: 60); primers for tissue inhibitor of metalloproteinase 3 (TIMP3) were 5'-GGCA-GCAGCGGCAATG-3' (SEQ ID NO: 61) and 5'-CCACCT-TGGCCCGGATCA-3' (SEQ ID NO: 62); and primers for GAPDH, an internal control, were 5'-AGCCA-CATCGCTCAGACAC-3' (SEQ ID NO: 63) and 5'-GC-CCAATACGACCAAATCC-3' (SEQ ID NO: 64).

The PCR involved 1 cycle of 94° C. for 2 min, followed by 35 cycles of 94° C. for 30 sec, a temperature corresponding to each primer for 30 sec, and 72° C. for 30 sec, and 1 cycle of 72° C. for 5 min. The temperature corresponding to each primer was 60° C. for heparin-binding EGF-like growth factor (HB-EGF), amphiregulin (AREG), stem cell factor (SCF), tumor necrosis factor (TNFα), and fas antigen (Fas), or 56° C. for the rest. The PCR products were subjected to electrophoresis for 30 min in a 2% agarose gel containing ethidium bromide, and their electrophoresis gel images were taken with a transilluminator.

Figure 16:
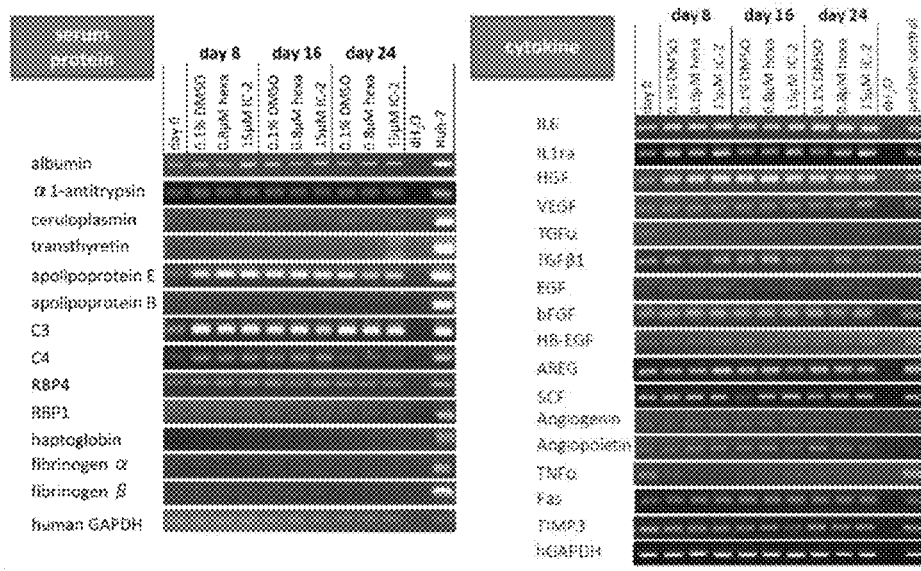
FIG. 16 is images illustrating the results of examining gene expression of cytokines.

FIG. 16 illustrates the results of examining gene expression of liver-specific secretory proteins and cytokines. As a result, hepatocytes as obtained using treatment with hexachlorophene or IC-2 had increased levels of expression of a plurality of the liver-specific secretory proteins and cytokines. In addition, even if the differentiation was induced, the levels of expression of the liver-specific secretory proteins or cytokines that are effective in liver regeneration were found to be maintained.

Example 9

Preparation of bFGF-Sustained-Release Device

A bFGF-sustained-release device was prepared in accordance with American Journal of Transplantation 2006, 6, 50-59 and Nature Medicine 2007, 13(7), 880-885. The bFGF-sustained-release device was implanted under the skin in the dorsal region of an immunodeficient mouse, a NOD-SCID mouse, to induce neovascularization. First, 1 μl of somnopentyl (Kyoritsuseiyaku Corporation), a systemic anesthetic, per 1 g of body weight of the NOD-SCID mouse was intraperitoneally administered to put the mouse under anesthesia. After the introduction of anesthesia, the left dorsal skin of the mouse was shaved. Next, operating scissors or a similar surgical instrument was used to cut, in a direction perpendicular to a body axis direction, about 1.5 to 2.0 cm of the skin with only subcutaneous tissue which was positioned approximately 1 cm caudal to the position where the bFGF device would be implanted. The operating scissors or the similar surgical instrument was inserted under the skin from this incision and moved toward the rostral direction to go beyond the position where the device would be implanted. Then, the operating scissors were made open, which created a space where the device could be implanted under the skin of the mouse. The bFGF device was inserted into this space, and the incision was closed with a surgical clip or a suture.

Figure 17:
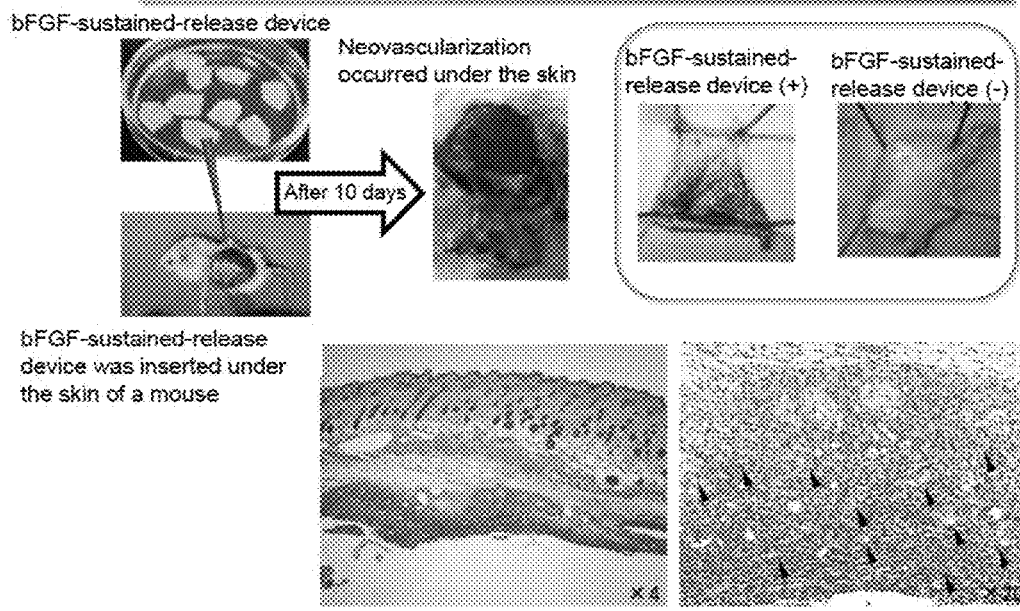
FIG. 17 is a diagram illustrating the results of examining a neovascularization effect induced by a bFGF-sustained-release device.

The mice were fed under normal conditions for 10 to 12 days. After 10 to 12 days, 1 μl of somnopentyl (Kyoritsu-seiyaku Corporation), a systemic anesthetic, per 1 g of body weight of the NOD-SCID mouse was intraperitoneally administered to put the mouse under anesthesia in a manner similar to when the bFGF device had been implanted. The portion surrounding the site where the bFGF device had been implanted was cut with operating scissors or a similar surgical instrument, and the skin with subcutaneous tissue was excised. As a control, the right dorsal skin with subcutaneous tissue having no implanted bFGF device was likewise cut in the same NOD-SCID mouse, and was excised. The excised skin with subcutaneous tissue was fixed with 4% paraformaldehyde (Nacalai Tesque). The post-fixed tissue was embedded in paraffin, used to prepare tissue sections by using a microtome, and stained with hematoxylin and eosin. By doing so, whether or not the implantation of the bFGF device under the skin exerted an neovascularization effect was examined (FIG. 17).

Example 10

Preparation of Cell Sheet and Subcutaneous Transplantation 7-week-old male NOD-SCID mice were divided into four groups (FIG. 18). Group 1 was a sham operation group in which no cell sheet was transplanted. Group 2 was a group in which one cell sheet was transplanted under the skin after the neovascularization. Group 3 was a group in which two cell sheets were transplanted under the skin after the neovascularization. Group 4 was a group in which three cell sheets were transplanted under the skin after the neovascularization. At 12 days before the cell sheet transplantation, the bFGF device was implanted under the dorsal skin of all the four groups to induce neovascularization.

First, 1 µl of somnopentyl (Kyoritsuseiyaku Corporation), a systemic anesthetic, per 1 g of body weight of a NOD-SCID mouse was intraperitoneally administered to put the mouse under anesthesia. After the introduction of anesthesia, the left dorsal skin of the mouse was shaved. Next, operating scissors or a similar surgical instrument was used to cut, in a direction perpendicular to a body axis direction, about 1.5 to 2.0 cm of the skin with only subcutaneous tissue which was positioned approximately 1 cm caudal to the position where the bFGF device would be implanted. The operating scissors or the similar surgical instrument was inserted under the skin from this incision and moved toward the rostral direction to go beyond the position where the device would be implanted. Then, the operating scissors were made open, which created a space where the device could be implanted under the skin of the mouse. The bFGF device was inserted into this space, and the incision was closed with a surgical clip or a suture.

After the mice were fed under normal conditions for 12 days, the cell sheet was transplanted. The cell sheets were prepared according to the following procedure. At 8 days before transplantation, a human bone marrow-derived mesenchymal stem cell line (UE7T-13 cells) was seeded on a 6-cm dish (CellSeed Inc.), which is an UpCell temperature-responsive cell cultureware for collecting a cell sheet, at a cell density of $9.0 \times 10^3$ cells/cm$^2$, and was cultured under conditions at 37° C. and 5% $CO_2$ in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 µg/ml streptomycin (Nacalai Tesque). This time point was set to day 0.

At the next day corresponding to day 1, the medium was changed to DMEM containing hexachlorophene at a final concentration of 0.8 µM. Similar to day 1, the medium was changed at day 4. At day 8 corresponding to one day before the cell sheet transplantation, the attached cells of periphery of the bottom of the dish was scraped with the tip of a disposable tip, etc., and the medium was changed with a medium at room temperature. Then, the cells were incubated under conditions at 20° C. and 5% $CO_2$ for 20 min or longer to produce a cell sheet. Until its transplantation, the cell sheet was kept under conditions at 20° C. and 5% $CO_2$.

At 12 days after the implantation of the bFGF device, the cell sheet was transplanted into Group 2 to 4 mice. First, 1 µl of somnopentyl (Kyoritsuseiyaku Corporation), a systemic anesthetic, per 1 g of body weight of the NOD-SCID mouse was intraperitoneally administered to put the mouse under anesthesia. Next, the incision opened during the implantation of the bFGF device was cut again. Then, operating scissors or a similar surgical instrument was used to cut only the subcutaneous tissue in a direction from the dorsal edge of the incision straight toward the rostral direction to open the subcutaneous tissue and to remove the bFGF device. After that, a Cell Shifter (CellSeed Inc.), which is a support for collecting a cell sheet, was placed on a cell sheet whose medium had been changed with serum-free DMEM and was then completely removed. The cell sheet, together with the support, was collected using forceps, etc. The support having thereon the cell sheet was placed on the site where the bFGF device had induced neovascularization. The operator waited about 3 to 5 min for adhesion of the cell sheet, and confirmed that the cell sheet was attached under the skin of the mouse. Thereafter, forceps, etc., were used to remove only the support.

Regarding Group 2, one cell sheet was transplanted, and the incision was then closed with a surgical clip or a suture. Regarding Groups 3 and 4, after forceps, etc., were used to remove the support, the second cell sheet was likewise transplanted onto the first cell sheet that had already been transplanted. Regarding Group 3, after two cell sheets were transplanted, the incision was then closed with a surgical clip or a suture. Regarding Group 4, the third cell sheet was transplanted again on the two cell sheets that had already been transplanted, and the incision was then closed with a surgical clip or a suture. Regarding Group 1 as a control, the bFGF device was removed using the same process as of Groups 2 to 4, and the incision was then closed with a surgical clip or a suture.

Then, the mice were fed under normal conditions again. At the next day after the operation, 0.2 µl of carbon tetrachloride per 1 g of body weight of the mouse was diluted by 10 times with olive oil, and was given to all the mice including Groups 1 to 4 through a disposable oral probe, namely a stomach tube. Whether or not the mice survived was daily checked from the day of the transplantation till 8 days after that. The body weight was measured once every other day. At days 2 and 4 after the cell sheet transplantation, the mice were put under inhalation anesthesia using isoflurane (Abbott Japan), and 100 to 200 µl of vein blood was drawn using a blood collecting capillary (HIRSCHMANN LABORGERATE) from the orbital plexus of the mice to collect the blood into a 1.5-ml tube. The collected vein blood stood still overnight on ice, and was then centrifuged in a cold centrifuge at 2,000 g and 4° C. for 20 min to separate serum. After that, only the serum was collected into a new 1.5-ml tube. Each necessary amount of the collected serum was dispensed into a 1.5-ml tube, and the tubes were stored in a deep freezer at −80° C. until their use.

At day 8 after the cell sheet transplantation, all the mice were put under inhalation anesthesia using isoflurane (Abbott Japan). Then, operating scissors or a similar surgical instrument, and forceps were used to perform laparotomy. After that, a 27-G needle and a 1-ml syringe were used to draw all the blood from inferior vena cava. After the blood sampling, a subcutaneous tissue containing a piece of the transplanted cell sheet and the whole liver were excised. The wet weight of the excised whole liver was measured, and its image was photographed with a digital camera. Of the excised tissues, those for RNA extraction were cut into small pieces at a wet weight of 0.1 g by means of operating scissors or a similar surgical instrument. Next, 1 ml of TRIzol (Invitrogen) was added thereto. Then, a POLYTRON (KINEMATICA AG) was used for homogenization, and the samples were stored at a freezer at −30° C. until they were used in experiments. Tissue pieces for protein extraction were likewise cut into small pieces at a wet weight of 0.1 g by means of operating scissors or a similar surgical instrument. The samples were put into a 15-ml tube, subsequently immersed in liquid nitrogen, instantaneously frozen, and stored in a deep freezer at −80° C. until they were used in experiments. Tissue pieces for histochemical staining were fixed with 4% paraformaldehyde (Nacalai Tesque). The post-fixed tissues were embedded in paraffin, and their tissue sections were then prepared with a microtome and stained with hematoxylin and eosin. Tissue sections other than those were stored at room temperature until immunohistochemical staining was carried out. Serum of the vein blood collected from inferior vena cava was separated using the same procedure as described above, and was stored in a deep freezer at −80° C.

The levels of serum transaminases of the mice at days 2, 4, and 8 after the cell sheet transplantation were determined using a Transaminase CII-Test Wako kit (Wako Pure Chemical Industries, Ltd.). The procedure was performed according to the attached protocol except that a reaction scale was reduced to one-quarter of the scale described in the package insert. The absorbance was read at 555 nm by using a microplate reader (Sunrise Absorbance Reader; Tecan Group Ltd.). According to a standard curve, the resulting absorbance was used to calculate an activity value (Karmen unit) and an international unit of each of aspartate aminotransferase (AST) and alanine aminotransferase (ALT).

The levels of serum bilirubin of the mice at days 2, 4, and 8 after the cell sheet transplantation were determined using a QuantiChrom Bilirubin Assay kit (BioAssaySystems). According to the attached protocol, the absorbance was read at 530 nm by using a microplate reader (Sunrise Absorbance Reader; Tecan Group Ltd.). According to a standard curve, the levels of total bilirubin were calculated.

FIG. 19 shows the above results. Subcutaneous transplantation of two or three layers of the cell sheet resulted in decreased levels of the serum transaminases. In addition, transplantation of one or more layers of the cell sheet resulted in decreased level of the bilirubin value.

Example 11

Preparation of Cell Sheet and Transplantation on Liver Surface 7-week-old male NOD-SCID mice were divided into four groups. Group 1 was a sham operation group in which no cell sheet was transplanted. Group 2 was a group in which one cell sheet was transplanted on the surface of the left lateral lobe of the liver. Group 3 was a group in which two cell sheets were transplanted on the surface of the left lateral lobe of the liver. Group 4 was a group in which three cell sheets were transplanted on the surface of the left lateral lobe of the liver.

The cell sheets were prepared according to the following procedure. At 8 days before the cell sheet transplantation, a human bone marrow-derived mesenchymal stem cell line (UE7T-13 cells) was seeded on a 6-cm dish (CellSeed Inc.), which is an UpCell temperature-responsive cell cultureware for collecting a cell sheet, at a cell density of $9.0 \times 10^3$ cells/cm$^2$, and was cultured under conditions at 37° C. and 5% $CO_2$ in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 µg/ml streptomycin (Nacalai Tesque). This time point was set to day 0.

At the next day corresponding to day 1, the medium was changed to DMEM containing hexachlorophene at a final concentration of 0.8 µM. Similar to day 1, the medium was changed at day 4. At day 8 corresponding to one day before the cell sheet transplantation, the attached cells of periphery of the bottom of the dish was scraped with the tip of a disposable tip, etc., and the medium was changed with a medium at room temperature. Then, the cells were incubated under conditions at 20° C. and 5% $CO_2$ for 20 min or longer to produce a cell sheet. Until its transplantation, the cell sheet was kept under conditions at 20° C. and 5% $CO_2$.

First, on the day of transplantation, 1 µl of somnopentyl (Kyoritsuseiyaku Corporation), a systemic anesthetic, per 1 g of body weight of the NOD-SCID mouse was intraperitoneally administered to put the mouse under anesthesia. After the introduction of anesthesia, the abdomen of the mouse was shaved, and operating scissors or a similar surgical instrument was used to cut the abdominal skin along the midline. Next, the peritoneum was dissected along the midline by using operating scissors or a similar surgical instrument. Then, forceps, etc., were used to hold the skin and the peritoneum to keep the surgical field open in the peritoneum. A suture was made to pass through the xiphoid process twice, and was pinched and fixed. This further allowed the surgical field surrounding the liver to be kept open. With regard to the cell sheet, after the medium was changed to serum-free DMEM in the cultureware, the medium was completely removed. Then, a Cell Shifter (CellSeed Inc.), which is a support for collecting a cell sheet, was placed on the cell sheet. This cell sheet, together with the support, was collected using forceps, etc. Then, the cell sheet having attached thereon the support was placed on the surface of the left lateral lobe of the liver. The operator waited about 3 to 5 min for adhesion of the cell sheet, and confirmed that the cell sheet was attached on the surface of the liver of the mouse. Thereafter, forceps, etc., were used to remove only the support.

With regard to Group 2, after the first cell sheet was transplanted, the suture that passed through the xiphoid process was removed; the forceps, etc., that fixed the peritoneum and the skin were taken out; and the peritoneum was closed with a suture. After that, the skin was closed with a surgical clip or a suture. Regarding Groups 3 and 4, after forceps, etc., were used to remove the support, the second cell sheet was likewise transplanted and overlaid onto the first cell sheet that had already been transplanted. With regard to Group 3, after the two cell sheets were transplanted, the suture that passed through the xiphoid process was removed; the forceps, etc., that fixed the peritoneum and the skin were taken out; and the peritoneum was closed with a suture. Thereafter, the skin was closed with a surgical clip or a suture. Regarding Group 4, the third cell sheet was transplanted on the two cell sheets that had already been transplanted, and the peritoneum and the skin were closed in a similar fashion. Regarding Group 1 as a control, after the same operation as of the transplantation groups was applied to keep the surgical field open, the peritoneum and the skin were closed.

Then, the mice were fed under normal conditions until the day of sacrifice. At day 7 after the cell sheet transplantation, the mice were put under inhalation anesthesia using isoflurane (Abbott Japan) and subjected to laparotomy in a manner similar to when the transplantation was performed. Thereafter, the whole liver was excised. The excised liver was photographed with a digital camera. Of the tissue pieces containing the transplanted cell sheet, those for RNA extraction were cut into small pieces at a wet weight of 0.1 g by means of operating scissors or a similar surgical instrument. Next, 1 ml of TRIzol (Invitrogen) was added thereto. Then, a POLYTRON (KINEMATICA AG) was used for homogenization, and the samples were stored at a freezer at −30° C. until they were used in experiments. Tissue pieces for histochemical staining were fixed with 4% paraformaldehyde (Nacalai Tesque). The post-fixed tissues were embedded in paraffin, and their tissue sections were then prepared with a microtome and stained with hematoxylin and eosin. Tissue sections other than those were stored at room temperature until immunohistochemical staining was carried out.

FIG. 20 shows the above results. Transplantation of the cell sheet on the liver surface resulted in suppression of liver dysfunction.

Example 12

Preparation of Cell Sheet and Transplantation on Two Sites of Liver Surface 9-week-old male NOD-SCID mice were divided into four groups (FIG. 21). Group 1 was a sham operation group in which no cell sheet was transplanted. Group 2 was a group in which one cell sheet was transplanted on each of two sites of the surface of the left lateral lobe of the liver. Group 3 was a group in which two cell sheets were transplanted on each of two sites of the surface of the left lateral lobe of the liver. Group 4 was a group in which three cell sheets were transplanted on each of two sites of the surface of the left lateral lobe of the liver.

The cell sheets were prepared according to the following procedure. At 8 days before the cell sheet transplantation, a human bone marrow-derived mesenchymal stem cell line (UE7T-13 cells) was seeded on a 6-cm dish (CellSeed Inc.), which is an UpCell temperature-responsive cell cultureware for collecting a cell sheet, at a cell density of $9.0 \times 10^3$ cells/cm$^2$, and was cultured under conditions at 37° C. and 5% $CO_2$ in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 μg/ml streptomycin (Nacalai Tesque). This time point was set to day 0.

At the next day corresponding to day 1, the medium was changed to DMEM containing hexachlorophene at a final concentration of 0.8 μM. Similar to day 1, the medium was changed at day 4. At day 8 corresponding to one day before the cell sheet transplantation, the attached cells of periphery of the bottom of the dish was scraped with the tip of a disposable tip, etc., and the medium was changed with a medium at room temperature. Then, the cells were incubated under conditions at 20° C. and 5% $CO_2$ for 20 min or longer to produce a cell sheet. Until its transplantation, the cell sheet was kept under conditions at 20° C. and 5% $CO_2$.

First, on the day of transplantation, 1 μl of somnopentyl (Kyoritsuseiyaku Corporation), a systemic anesthetic, per 1 g of body weight of the NOD-SCID mouse was intraperitoneally administered to put the mouse under anesthesia. After the introduction of anesthesia, the abdomen of the mouse was shaved, and operating scissors or a similar surgical instrument was used to cut the abdominal skin along the midline. Next, the peritoneum was dissected along the midline by using the operating scissors or the similar surgical instrument. Then, forceps, etc., were used to hold the skin and the peritoneum to keep the surgical field open in the peritoneum. A suture was made to pass through the xiphoid process twice, and was pinched and fixed. This further allowed the surgical field surrounding the liver to be kept open. With regard to the cell sheet, after the medium was changed to serum-free DMEM in the cultureware, the medium was completely removed. Then, a Cell Shifter (CellSeed Inc.), which is a support for collecting a cell sheet, was placed on the cell sheet. This cell sheet, together with the support, was collected using forceps, etc. Then, the cell sheet having attached thereon the support was placed on each of two sites of the surface of the left lateral lobe of the liver. The operator waited about 3 to 5 min for adhesion of the cell sheet, and confirmed that the cell sheet was attached on the surface of the liver of the mouse. Thereafter, forceps, etc., were used to remove only the support.

With regard to Group 2, after the first cell sheet was transplanted on each of two sites, the suture that passed through the xiphoid process was removed; the forceps, etc., that fixed the peritoneum and the skin were taken out; and the peritoneum was closed with a suture. After that, the skin was closed with a surgical clip or a suture. Regarding Groups 3 and 4, after forceps, etc., were used to remove the support, the second cell sheet was likewise transplanted and overlaid onto each of the first cell sheet that had already been transplanted. With regard to Group 3, after the two cell sheets were transplanted on each of two sites, the suture that passed through the xiphoid process was removed; the forceps, etc., that fixed the peritoneum and the skin were taken out; and the peritoneum was closed with a suture. Then, the skin was closed with a surgical clip or a suture. Regarding Group 4, the third cell sheet was transplanted on each of two sites having the cell sheets that had already been transplanted, and the peritoneum and the skin were closed in a similar fashion. Regarding Group 1 as a control, after the same operation as of the transplantation groups was applied to keep the surgical field open, the peritoneum and the skin were closed.

At the next day after the operation, 0.2 μl of carbon tetrachloride per 1 g of body weight of the mouse was diluted by 10 times with olive oil, and was given to all the mice including Groups 1 to 4 through a disposable oral probe, namely a stomach tube. Whether or not the mice survived was daily checked from the day of the transplantation till 8 days after that. The body weight was measured once every other day. At days 2 and 4 after the cell sheet transplantation, the mice were put under inhalation anesthesia using isoflurane (Abbott Japan), and 100 to 200 μl of vein blood was drawn using a blood collecting capillary (HIRSCHMANN LABORGERATE) from the orbital plexus vein of the mice to collect the blood into a 1.5-ml tube. The collected vein blood stood still overnight on ice, and was then centrifuged in a cold centrifuge at 2,000 g and 4° C. for 20 min to separate serum. After that, only the serum was collected into a new 1.5-ml tube. Each necessary amount of the collected serum was dispensed into a 1.5-ml tube, and the tubes were stored in a deep freezer at −80° C. until their use.

At day 8 after the cell sheet transplantation, all the mice were put under inhalation anesthesia using isoflurane (Abbott Japan). Then, operating scissors or a similar surgical instrument, and forceps were used to perform laparotomy. After that, a 27-G needle and a 1-ml syringe were used to draw all the blood from inferior vena cava. After the blood sampling, the whole liver was excised. The wet weight of the excised whole liver was measured, and its image was photographed with a digital camera. Of the tissue pieces containing the transplanted cell sheet, those for RNA extraction were cut into small pieces at a wet weight of 0.1 g by means of operating scissors or a similar surgical instrument. Next, 1 ml of TRIzol (Invitrogen) was added thereto. Then, a POLYTRON (KINEMATICA AG) was used for homogenization, and the samples were stored at a freezer at −30° C. until they were used in experiments. Tissue pieces for protein extraction were likewise cut into small pieces at a wet weight of 0.1 g by means of operating scissors or a similar surgical instrument. The samples were put into a 15-ml tube, subsequently immersed in liquid nitrogen, instantaneously frozen, and stored in a deep freezer at −80° C. until they were used in experiments. Tissue pieces for histochemical staining were fixed with 4% paraformaldehyde (Nacalai Tesque). The post-fixed tissues were embedded in paraffin, and their tissue sections were then prepared with a microtome and stained with hematoxylin and eosin. Tissue sections other than those were stored at room temperature until immunohistochemical staining was carried out. Serum of the vein blood collected from inferior vena cava was separated using the same procedure as described above, and was stored in a deep freezer at −80° C.

Figure 22:
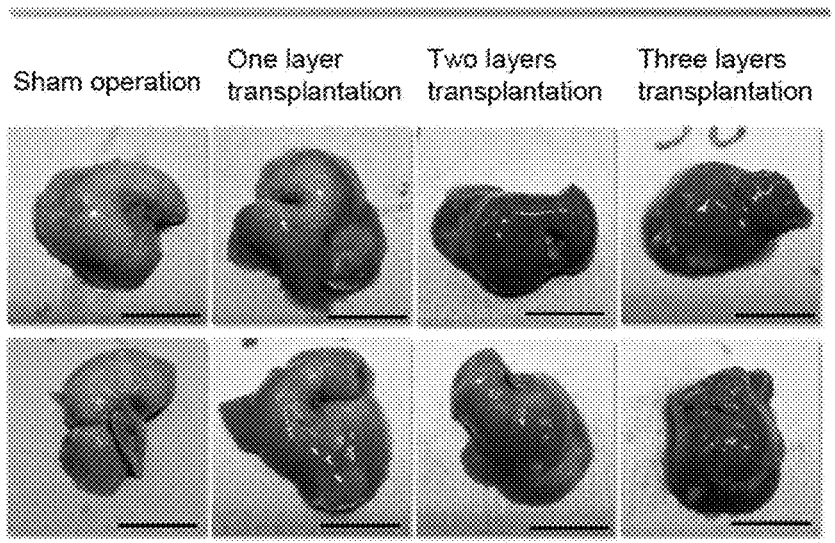
FIG. 22 is photos of a liver when cell sheets were transplanted on two sites of a liver surface.

FIG. 22 shows the above results. Transplantation of the cell sheet on two sites of the liver surface resulted in suppression of liver dysfunction. This suppression was remarkable when two or three layers of the cell sheet were transplanted.

The levels of serum transaminases of the mice at days 2, 4, and 8 after the cell sheet transplantation were determined using a Transaminase CII-Test Wako kit (Wako Pure Chemical Industries, Ltd.). The procedure was performed according to the attached protocol except that a reaction scale was reduced to one-quarter of the scale described in the package insert. The absorbance was read at 555 nm by using a microplate reader (Sunrise Absorbance Reader; Tecan Group Ltd.). According to a standard curve, the resulting absorbance was used to calculate an activity value (Karmen unit) and an international unit of each of aspartate aminotransferase and alanine aminotransferase.

Figure 23:
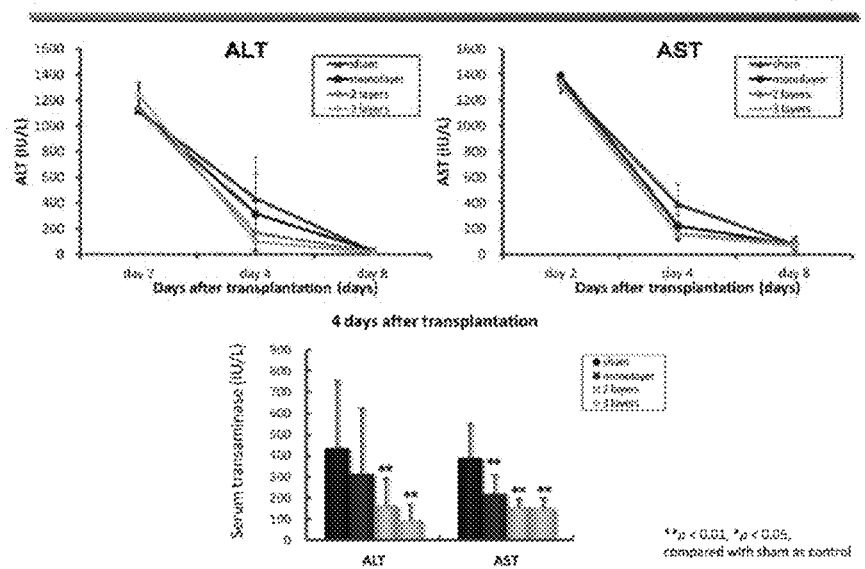
FIG. 23 is graphs illustrating the results of how liver functions changed when cell sheets were transplanted on two sites of a liver surface.

FIG. 23 shows the results. Transplantation of the cell sheet on two sites of the liver surface resulted in a large decrease in levels of the serum transaminases. This decrease was remarkable when two or three layers of the cell sheet were transplanted.

The levels of serum bilirubin of the mice at days 2, 4, and 8 after the cell sheet transplantation were determined using a QuantiChrom Bilirubin Assay kit (BioAssaySystems). According to the attached protocol, the absorbance was read at 530 nm by using a microplate reader (Sunrise Absorbance Reader; Tecan Group Ltd.). According to a standard curve, the levels of total bilirubin were calculated.

Figure 24:
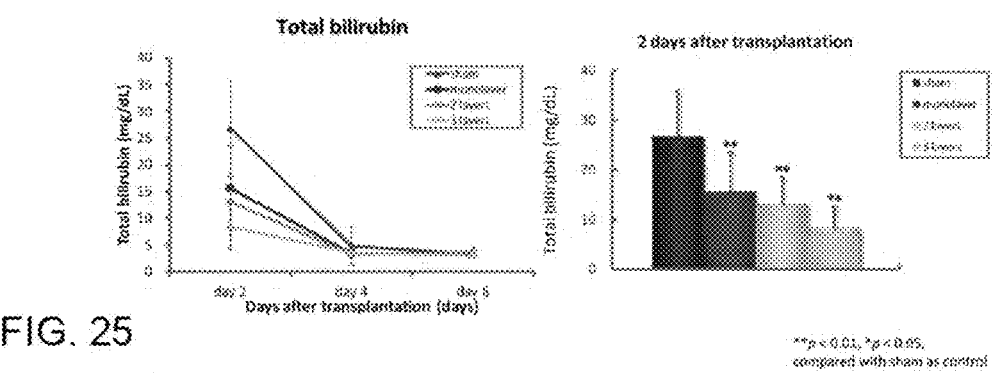
FIG. 24 is graphs illustrating the results of how liver functions changed when cell sheets were transplanted on two sites of a liver surface.

FIG. 24 shows the results. Transplantation of the cell sheet on two sites of the liver surface resulted in a large decrease in levels of bilirubin.

The number of surviving mice was counted each day after the transplantation according to the procedure in FIG. 21. Based on the number, a survival curve was drawn using PASW statistical software according to a Kaplan-Meier method. The survival rate was tested by a logrank test.

Figure 25:
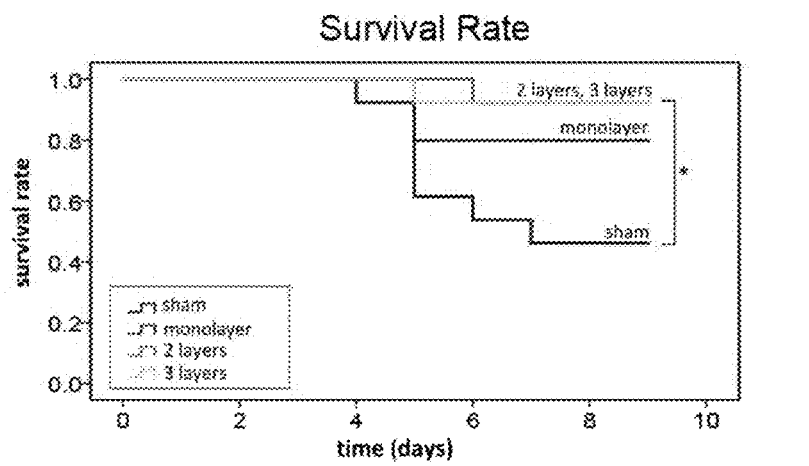
FIG. 25 is a graph illustrating the results of examining survival rates of mice when cell sheets were transplanted on two sites of a liver surface.

FIG. 25 shows the results. Transplantation of the cell sheet on two sites of the liver surface resulted in a large increase in the survival rate.

Samples were stored for RNA extraction according to the procedure in FIG. 21. Then, their total RNA was extracted according to the attached instruction regarding TRIzol (Invitrogen). After the extraction, deoxyribonuclease (Nippon Gene) was added, and the mixture was incubated at 37° C. for 30 min to remove DNA. In a reverse transcription reaction, SuperScriptII Reverse Transcriptase (Invitrogen) and Oligo(dT)$_{15}$ primer were added to 1 µg of RNA to convert it into cDNA. In a RT-PCR method, the cDNA was diluted by 5 times. Next, 1 µl of the cDNA was used as a template. Then, rTaq DNA polymerase (TOYOBO) was used to amplify the cDNA. After that, a PCR was conducted according to the procedure described in the above Example 8. The PCR products were subjected to electrophoresis for 30 min in a 2% agarose gel containing ethidium bromide, and their electrophoresis gel images were taken with a transilluminator.

Figure 26:
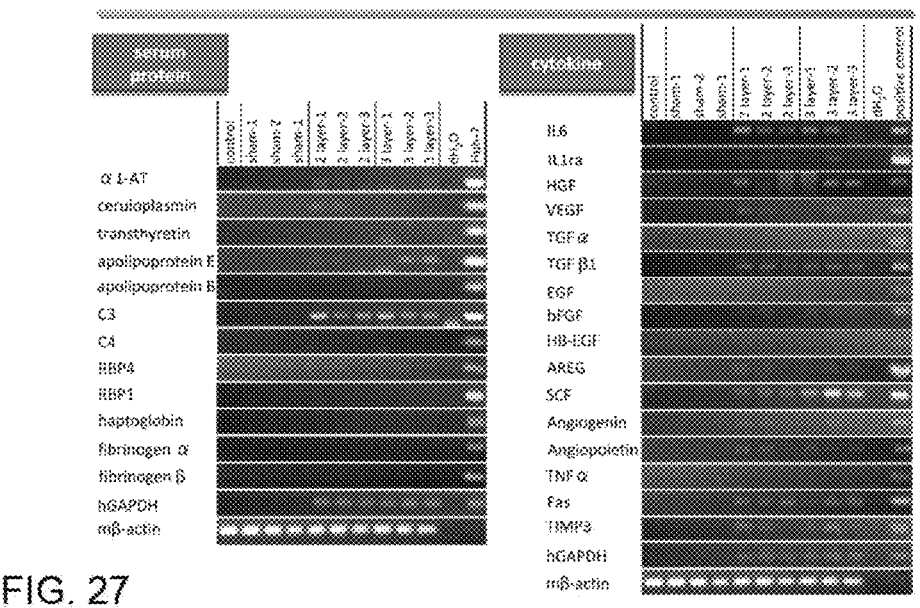
FIG. 26 is images illustrating the results of examining gene expression of liver-specific secretory proteins and cytokines.

FIG. 26 illustrates the results of examining gene expression of liver-specific secretory proteins and cytokines. Among those shown in FIG. 26, serum protein markers or cytokines having increased expression (e.g., $\alpha$1-AT) seem to be effective in liver regeneration. Note that markers having no recognizable expression (e.g., Apolipoprotein B) may not be directly involved in the present liver regeneration mechanism. In addition, when the cell sheet was transplanted on two or more sites of the liver surface, in particular, serum protein markers and cytokines had increased gene expression compared with those when no cell sheet was transplanted.

Tissue sections as prepared according to the procedure in FIG. 21 were used to perform immunofluorescence staining. Human $\alpha$1-antitrypsin was stained according to the following procedure. Tissue sections were subjected to deparaffinization using xylene and hydration treatment using 100% ethanol, were washed with tap water followed by washing with 1×PBS(−), and were then blocked in a blocking solution containing goat serum at room temperature for 20 min. One or two drops of a rabbit polyclonal anti-$\alpha$1-antitrypsin antibody (Abcam) were added to the tissue sections. The sections were kept in a moist chamber at 4° C. overnight to carry out a primary antibody reaction. After washing with 1×PBS(−), 100 µl of Alexa Fluor 488 goat anti-rabbit IgG (H+L) antibody (Invitrogen) that had been diluted by 200 times was added onto the tissue sections. Then, the sections were kept in a dark place at room temperature for 1 h to carry out a secondary antibody reaction. After washing with 1×PBS(−), each section was covered. Staining images were observed under a fluorescence microscope (IX71, Olympus Corporation), and the images were obtained.

Figure 27:
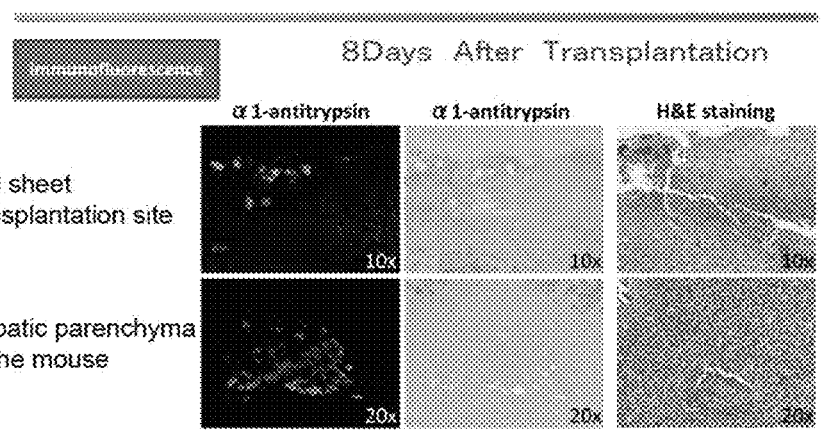
FIG. 27 is pictures illustrating the results of examining levels of expression of human a 1-antitrypsin when cell sheets were transplanted on two sites of a liver surface.

FIG. 27 shows the above results. The transplanted hepatocyte sheet and hepatic parenchyma of the mouse were found to have expression of human $\alpha$1-antitrypsin.

Example 13

Figure 28:
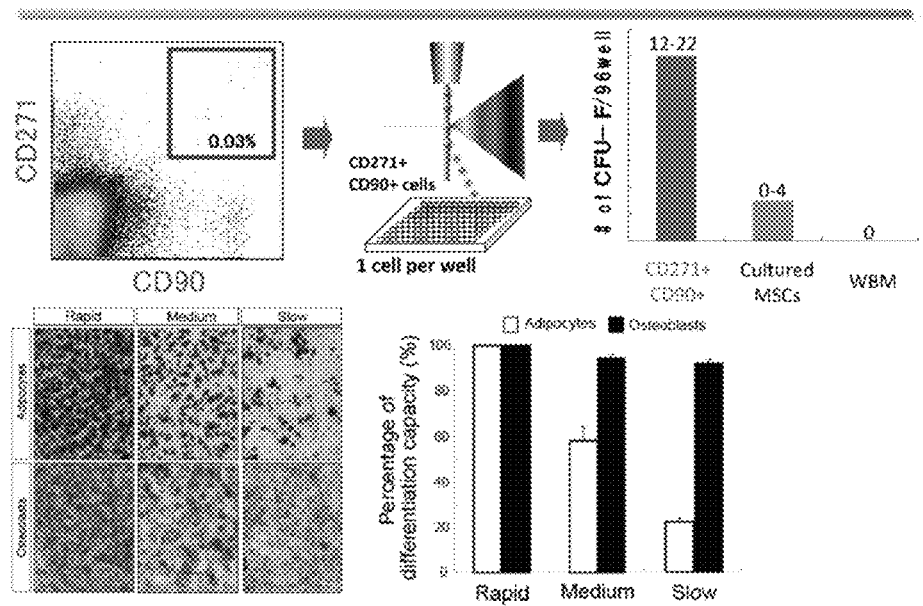
FIG. 28 provides an overview of a method for sorting a mesenchymal stem cell (JP2009-060840A).

Sorting of Mesenchymal Stem Cell and Differentiation Induction into Hepatocytes (1) Method for Sorting Mesenchymal Stem Cell Professor Okano and Associate Professor Matsuzaki of Keio University have developed a method for sorting a CD90$^+$CD271$^+$ mesenchymal stem cell (JP2009-060840A). FIG. 28 shows an overview of the method. Based on the method, mesenchymal stem cells were sorted.

(2) Method for Separation, Preparation, and Culture of Bone Marrow-derived Mesenchymal Stem Cells Human bone marrow mononuclear cells that had been purchased from Lonza Inc. were suspended in 1 ml of Hanks' balanced salt solution (HBSS, Gibco, Life Technologies Corp.) supplemented with a 100-fold diluted APC-labeled anti-CD90 antibody, a 407-fold diluted PE-labeled anti-CD271 antibody, and 2% fetal bovine serum (FBS, Defined, Thermo Fisher Scientific Inc.), and were stained on ice for 30 min. A flow cytometer (MoFlo XDP, Beckman Coulter Inc.) was used to selectively separate mesenchymal stem cells. The resulting cells were cultured in Dulbecco's Modified Eagle's Medium (Low Glucose, Gibco, Life Technologies Corp.) containing 20% FBS, 100 U/ml penicillin, 100 ng/ml streptomycin (Nacalai Tesque), and 20 ng/ml basic fibroblast growth factor (TRANS GENIC INC., Ltd.) on a 35-mm dish under conditions at 37° C. and 5% $CO_2$. The medium was changed every 4 days. After colonies were formed, the cells were detached using a 0.025% trypsin/1 mM EDTA solution (Nacalai Tesque), split on a 100-mm dish, and cultured under conditions at 37° C. and 5% $CO_2$. Then, the cells which were kept 70 to 80% confluent were detached using trypsin treatment. These cells in one dish were divided into four dishes for passage.

(3) Differentiation Induction into Hepatocytes and Luciferase Assay

Cells were seeded on a 96-well plate at a cell density of $5.0 \times 10^3$ cells/cm². After 24 h, the medium was changed to a medium containing 0.1% DMSO or IC-2 (at a final concentration of 40 or 45 µM). Then, the cells were cultured under conditions at 37° C. and 5% $CO_2$. At 4 days after the cells were seeded, the medium was changed to a medium containing the above compound. At 3 days before measurement, the cells were infected at MOI=10 with a lentivirus (SABiosciences, QIAGEN N.V.) that expressed firefly luciferase under control of mCMV promoter. As an internal control, the cells were simultaneously infected with a lentivirus (SABiosciences, QIAGEN N.V.) that expressed Renilla luciferase. At 8 days after the chemical treatment with the above compound, a Dual-Luciferase Reporter Assay System (Promega Corp.) was used to measure luciferase activity by using a luminometer.

Figure 29:
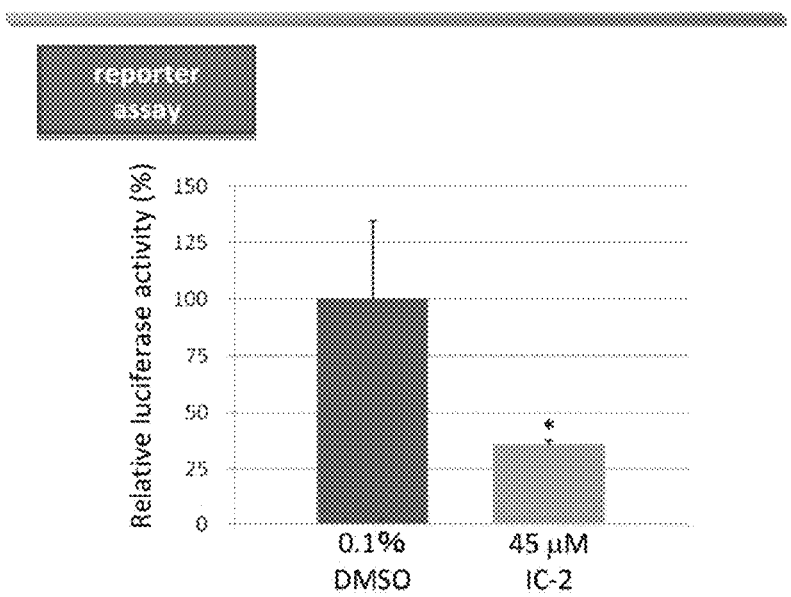
FIG. 29 is a graph illustrating the results of measuring luciferase activity.

FIG. 29 shows the results of the luciferase assay. The results demonstrated that treatment of the bone marrow-derived mesenchymal stem cells with IC-2 significantly inhibited the Wnt/β-catenin signaling pathway at 8 days after the treatment.

(4) Differentiation Induction into Hepatocytes and Evaluation of Gene Expression of Hepatocyte Differentiation Markers Cells were seeded on a 6-well plate at a cell density of $1.8 \times 10^4$ cells/cm². This day was designated as day 0. At day 1 corresponding to the next day, the medium was changed to a medium containing IC-2 (at a final concentration of 25, 35, or 45 µM) or 0.1% DMSO. At day 4, the medium was changed in a manner similar to that at day 1, and at day 8, the cells were reseeded and subcultured at a cell density of $1.8 \times 10^4$ cells/cm². After that, the medium was replaced twice during 8 days, and the cells were subcultured every 8 days. Then, the similar operation was carried out until day 24. At days 8, 16, and 24 after the initiation of the induction, TRIzol (Invitrogen) was used to extract total RNA according to the attached instruction. After the extraction, deoxyribonuclease (Nippon Gene) was added, and the mixture was incubated at 37° C. for 30 min to remove DNA. In a reverse transcription reaction, SuperScriptII Reverse Transcriptase (Invitrogen) and Oligo(dT)15 primer were added to 1 µg of RNA to convert it into cDNA. In a RT-PCR method, the cDNA was diluted by 5 times. Next, 1 µl of the cDNA was used as a template. Then, rTaq DNA polymerase (TOYOBO) was used to amplify the cDNA. MQ water was used as a negative control. cDNA from Huh-7 or UE7T-13 cells was used as a positive control.

In order to determine hepatocyte differentiation markers, levels of expression of albumin were measured. The primers used had the following sequences: 5'-TTGGAAAAATC-CCACTGCAT-3' (SEQ ID NO: 1) and 5'-CTCCAAGCT-GCTCAAAAAGC-3' (SEQ ID NO: 2).

The PCR involved 1 cycle of 94° C. for 2 min, followed by 35 cycles of 94° C. for 30 sec, 58° C. for 30 sec, and 72° C. for 30 sec, and 1 cycle of 72° C. for 5 min. The PCR products were subjected to electrophoresis for 30 min in a 2% agarose gel containing ethidium bromide, and their electrophoresis gel images were taken with a transilluminator.

Figure 30:
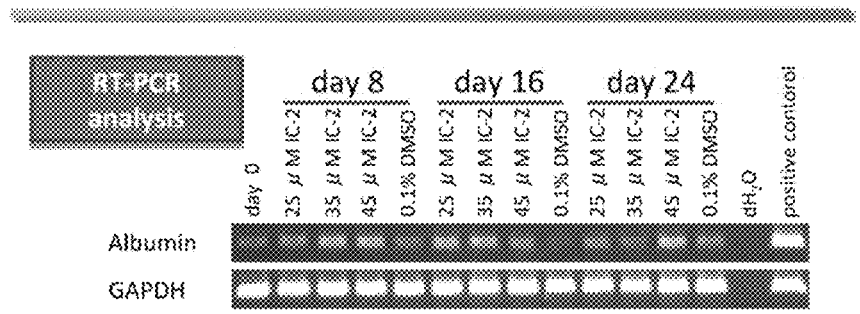
FIG. 30 is images illustrating the results of examining gene expression of a hepatocyte differentiation marker.

FIG. 30 shows the results of examining gene expression of albumin. These results demonstrated that treatment with 45 µM of IC-2, which had exhibited an effect of inhibiting the Wnt/β catenin signaling pathway in the above FIG. 29, induced a remarkable increase in albumin expression when compared with 0.1% DMSO.

Example 14

Sorting of Clinical Specimen-derived Mesenchymal Stem Cells and Differentiation Induction into Hepatocytes (1) Method for Separation, Preparation, and Culture of Clinical Specimen-derived Mesenchymal Stem Cells A fresh bone marrow aspirate was collected under informed consent from a patient (a 60 years old woman) with osteoarthritis who underwent replacement arthroplasty at the Department of Orthopedic Surgery, Tottori University Hospital. This aspirate was subjected to density gradient centrifugation using ficoll (Amersham Biosciences) to separate bone marrow mononuclear cells (FIG. 31). These bone marrow mononuclear cells were suspended in 1 ml of Hanks' balanced salt solution (HBSS, Gibco, Life Technologies Corp.) supplemented with a 100-fold diluted APC-labeled anti-CD90 antibody, a 407-fold diluted PE-labeled anti-CD271 antibody, and 2% fetal bovine serum (FBS, Defined, Thermo Fisher Scientific Inc.), and were stained on ice for 30 min. A flow cytometer (MoFlo XDP, Beckman Coulter Inc.) was used to selectively separate mesenchymal stem cells. The resulting cells were cultured in Dulbecco's Modified Eagle's Medium (Low Glucose, Gibco, Life Technologies Corp.) containing 20% FBS, 100 U/ml penicillin, 100 ng/ml streptomycin (Nacalai Tesque), and 20 ng/ml basic fibroblast growth factor (TRANS GENIC INC., Ltd.) on a 35-mm dish under conditions at 37° C. and 5% $CO_2$. The medium was changed every 4 days. After colonies were formed, the cells were detached using a 0.025% trypsin/1 mM EDTA solution (Nacalai Tesque), split on a 100-mm dish, and cultured under conditions at 37° C. and 5% $CO_2$. Then, the cells which were kept 70 to 80% confluent were detached using trypsin treatment. These cells in one dish were divided into four dishes for passage.

(2) Differentiation Induction into Hepatocytes and Evaluation of Gene Expression of Hepatocyte Differentiation Markers Cells were seeded on a 6-well plate at a cell density of $1.8 \times 10^4$ cells/cm². This day was designated as day 0. At day 1 corresponding to the next day, the medium was changed to a medium containing any one of hexachlorophene (at a final concentration of 4 µM), HC-2 (at a final concentration of 20 µM), PN-3-13 (at a final concentration of 20 µM), IC-2 (at a final concentration of 40 µM), and 0.1% DMSO. At day 4, the medium was changed in a manner similar to that at day 1, and at day 8, the cells were reseeded and subcultured at a cell density of $1.8 \times 10^4$ cells/cm². After that, the medium was replaced twice during 8 days, and the cells were subcultured every 8 days. Then, the similar operation was carried out until day 24. At days 8, 16, and 24 after the initiation of the induction, TRIzol (Invitrogen) was used to extract total RNA according to the attached instruction. The following procedure was likewise carried out according to the procedure described in the above Example 13(4).

FIG. 32 shows the results of examining gene expression of hepatocyte differentiation markers. When any of hexachlorophene, HC-2, PN-3-13, and IC-2 was used, expression of albumin was induced.

(3) Differentiation Induction into Hepatocytes and Immunofluorescence Staining

A cover glass that had been sterilized with 100% ethanol was placed on a 12-well plate. Cells were seeded on the cover glass at a cell density of $1.8 \times 10^4$ cells/cm$^2$. This day was designated as day 0. At day 1 corresponding to the next day, the medium was changed to a medium containing HC-2 (at a final concentration of 20 µM), PN-3-13 (at a final concentration of 20 µM), IC-2 (at a final concentration of 40 µM), or 0.1% DMSO. At day 4, the medium was changed in a manner similar to that at day 1. At day 8, the culture medium was removed and the cells were washed twice with PBS. Then, in order to perform immunostaining of albumin, the cells were fixed for 20 min with 4% paraformaldehyde (Nacalai Tesque) containing 8% sucrose (Wako Pure Chemical Industries, Ltd.). For immunostaining of C/EBPα or CYP1A1, the cells were fixed for 20 min with 4% paraformaldehyde. After that, the cells were permeated with 0.2% Triton X-100 (Wako Pure Chemical Industries, Ltd.) for 10 min and were then blocked in 3% BSA (Nacalai Tesque) at room temperature for 30 min without shaking.

The cells were covered with each of a 1,000-fold diluted monoclonal anti-human serum albumin antibody (Sigma-Aldrich Corp.), a 125-fold diluted polyclonal anti-human CCAAT enhancer-binding protein A antibody (Santa Cruz Biotechnology, Inc.), and a 250-fold diluted polyclonal anti-CYP1A1 antibody (Santa Cruz Biotechnology, Inc.) as a primary antibody, and were kept at 4° C. overnight to carry out a primary antibody reaction. After the primary antibody reaction, the cells were washed with 0.1% BSA/PBS. For albumin staining, a 1,000-fold diluted Alexa Fluor 488 goat anti-mouse immunoglobulin G antibody (Molecular Probes) was used. For other staining, an Alexa Fluor 594 goat anti-rabbit immunoglobulin G antibody (Molecular Probes) was used. The cells were incubated with each antibody, and were kept in a dark condition at room temperature for 1 h to carry out a secondary antibody reaction. Their nuclei were stained with DAPI (Cell Signaling Technology Inc.). After the reaction, the cells were washed with 0.2% Tween-20 (Nacalai Tesque). Further, the cells were washed with MQ water. Then, the cover glass was picked up, placed on a slide glass, sealed, and observed under a FV1000D IX81 microscope (Olympus Corporation). A hepatoma cell line Huh-7 was used as a positive control for immunofluorescence staining. As a negative control, used were CD90$^+$CD271$^+$ bone marrow-derived mesenchymal stem cells that were seeded one day before the day of the immunostaining and were not subjected to the differentiation induction.

Figure 33:
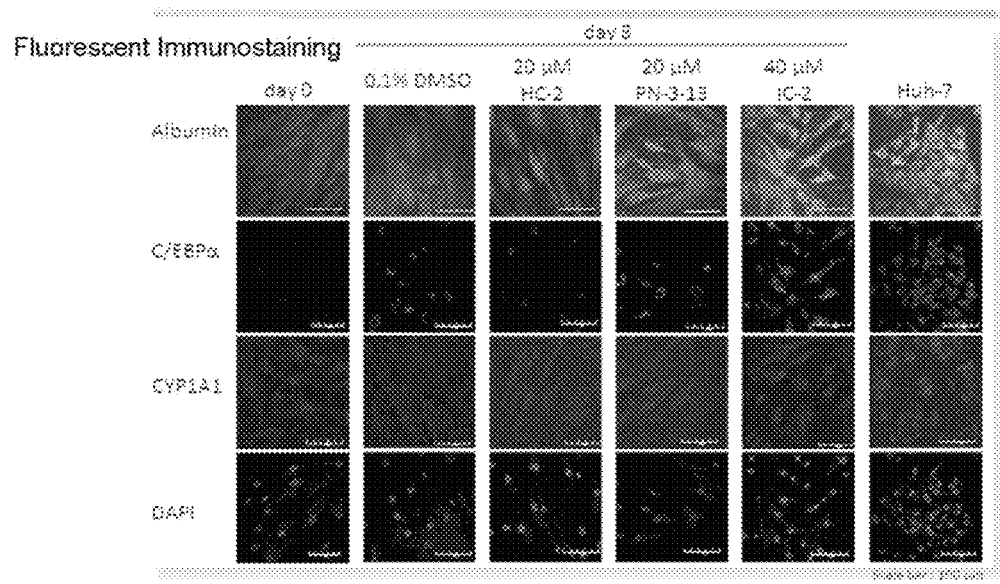
FIG. 33 is photomicrographs (immunofluorescence staining) illustrating an ability of inducing differentiation into hepatocytes by using PN-3-13 or IC-2.

FIG. 33 shows the results of immunofluorescence staining. At day 8, treatment with PN-3-13 or IC-2 apparently increased levels of expression of any of albumin, C/EBPα, and CYP1A1, which are representative markers for differentiation into hepatocytes, compared with those of a negative control (0.1% DMSO). In addition, the levels were close to those of a positive control (Huh-7).

(4) Differentiation Induction into Hepatocytes and Urea Assay

A urea assay was performed according to the following protocol. CD90$^+$CD271$^+$ bone marrow-derived mesenchymal stem cells were seeded on a 24-well plate at a cell density of $1.8 \times 10^4$ cells/cm$^2$. This day was designated as day 0. At day 1 corresponding to the next day, each medium was changed to a medium containing hexachlorophene (at a final concentration of 4 µM), HC-2 (at a final concentration of 20 µM), PN-3-13 (at a final concentration of 20 µM), IC-2 (at a final concentration of 40 µM), or 0.1% DMSO. At day 4, the medium was changed in a manner similar to that at day 1, and the cells were cultured until day 8. At day 8, the medium was removed, and replaced with a medium containing ammonium chloride (Nacalai Tesque) at a final concentration of 5 mM. The cells were further cultured for 96 h. At 96 h after the addition of ammonium chloride, levels of urea in the medium were determined using a QuantiChrom Urea Assay Kit (BioAssay Systems) according to the attached protocol by reading the absorbance at a wavelength of 520 nm with a microplate reader. The levels of urea were calculated based on a standard sample according to the attached calculation method. As a negative control for the urea assay, used were CD90$^+$CD271$^+$ bone marrow-derived mesenchymal stem cells that were seeded one day before the day of the immunostaining and were not subjected to the differentiation induction.

Figure 34:
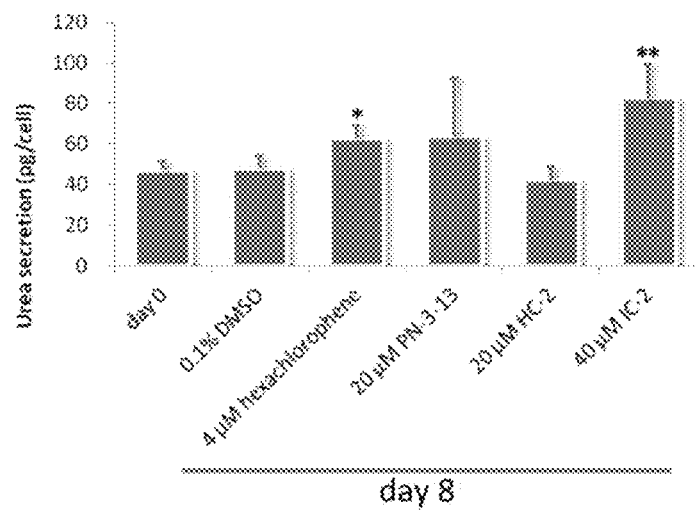
FIG. 34 is a graph illustrating an ability (urea synthesis) of inducing differentiation into hepatocytes by using hexachlorophene, PN-3-13, or IC-2.

FIG. 34 shows the results of the urea assay. Use of any of hexachlorophene, PN-3-13, and IC-2 resulted in an apparent increase in cellular urea synthesis when compared with a negative control (0.1% DMSO). The above results indicate that the cells treated with hexachlorophene, PN-3-13, or IC-2 not only just express hepatocyte markers but also exert potentials as functional hepatocytes.

(5) Differentiation Induction into Hepatocytes and PAS Staining

PAS staining was performed according to the following procedure. A cover glass that had been sterilized with 100% ethanol was placed on a 12-well plate. Cells were seeded on the cover glass at a cell density of $1.8 \times 10^4$ cells/cm$^2$. This day was designated as day 0. At day 1 corresponding to the next day, each medium was changed to a medium containing HC-2 (at a final concentration of 20 µM), PN-3-13 (at a final concentration of 20 µM), IC-2 (at a final concentration of 40 µM), or 0.1% DMSO. At day 4, the medium was changed in a manner similar to that at day 1, and the cells were cultured until day 8. At day 8, the cells were washed twice with PBS and were fixed with 4% paraformaldehyde for 30 min. As a negative control, α-amylase (Nacalai Tesque) at a final concentration of 10 mg/ml was added, and the cells were incubated therewith at 37° C. for 1 h to digest their glycogen. Subsequently, the cells were treated with 1% aqueous periodic acid for 5 min. Then, the cells were treated with a Schiff reagent (Nacalai Tesque) for 15 min to stain glycogen. After that, the cells were washed three times with aqueous sulfurous acid and were then washed three times with distilled water. The nuclei were stained with Mayer's Hematoxylin (MUTO PURE CHEMICALS CO., LTD.) for 1 min. Thereafter, the cover glass was picked up, placed on a slide glass, sealed, and observed under a light microscope (IX71, Olympus Corporation). A hepatoma cell line Huh-7 was used as a positive control for PAS staining. As a negative control, used were $CD90^+CD271^+$ bone marrow-derived mesenchymal stem cells that were seeded one day before the day of the immunostaining and were not subjected to the differentiation induction.

Figure 35:
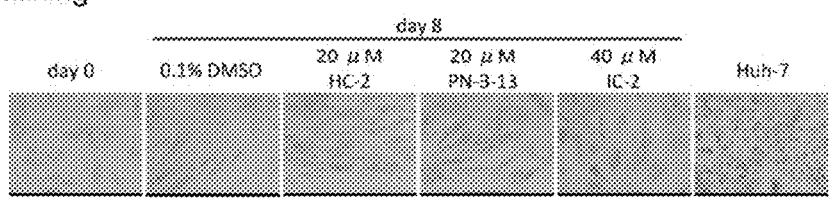
FIG. 35 is photomicrographs (PAS staining) illustrating an ability of inducing differentiation into hepatocytes by using PN-3-13 or IC-2.

FIG. 35 shows the results of the PAS staining. Use of any of PN-3-13 and IC-2 resulted in an apparent increase in cellular glycogen accumulation when compared with a negative control (0.1% DMSO).

Example 15

Preparation of Cell Sheet and Transplantation on Liver Surface 7-week-old male NOD-SCID mice were divided into three groups. Group 1 was a sham operation group in which no cell sheet was transplanted. Group 2 was a group transplanted with a cell sheet prepared by inducing differentiation of $CD90^+CD271^+$ bone marrow-derived mesenchymal stem cells (hereinafter, referred to as "healthy cells") separated and prepared from bone marrow mononuclear cells that had been purchased from Lonza Inc. Group 3 was a group transplanted with a cell sheet prepared by inducing differentiation of $CD90^+CD271^+$ bone marrow-derived mesenchymal stem cells (hereinafter, referred to as "patient cells") separated and prepared from bone marrow of a patient who underwent replacement arthroplasty at the Department of Orthopedic Surgery, Tottori University Hospital.

The cell sheets were prepared according to the following procedure. At 8 days before cell sheet transplantation, each of healthy and patient $CD90^+CD271^+$ bone marrow-derived mesenchymal stem cells was seeded on a 6-cm dish (CellSeed Inc.), an UpCell temperature-responsive cell cultureware for collecting a cell sheet, at a cell density of $1.8 \times 10^4$ cells/cm². The respective cells were cultured in DMEM (Low Glucose, Gibco, Life Technologies Corp.) containing 20% FBS, 100 U/ml penicillin, 100 ng/ml streptomycin (Nacalai Tesque), and 20 ng/ml basic fibroblast growth factor (TRANS GENIC INC., Ltd.) under conditions at 37° C. and 5% $CO_2$. This time point was set to day 0.

At the next day corresponding to day 1, the medium of the healthy cells was changed to a medium containing IC-2 at a final concentration of 45 µl, and the medium of the patient cells was changed to a medium containing IC-2 at a final concentration of 45 µl. Similar to day 1, the medium was changed at day 4. At day 8 corresponding to one day before the cell sheet transplantation, the attached cells of periphery of the bottom of the dish was scraped with the tip of a disposable tip, etc., and the medium was changed with a medium at room temperature. Then, the cells were incubated under conditions at 20° C. and 5% $CO_2$ for 30 min or longer to produce a cell sheet. Until its transplantation, the cell sheet was kept under conditions at 20° C. and 5% $CO_2$.

First, on the day of transplantation, 1 µl of somnopentyl (Kyoritsuseiyaku Corporation), a systemic anesthetic, per 1 g of body weight of the NOD-SCID mouse was intraperitoneally administered to put the mouse under anesthesia. After the introduction of anesthesia, the abdomen of the mouse was shaved, and operating scissors or a similar surgical instrument was used to cut the abdominal skin along the midline. Next, the peritoneum was dissected along the midline by using the operating scissors or the similar surgical instrument. Then, forceps, etc., were used to hold the skin and the peritoneum to keep the surgical field open in the peritoneum. A suture was made to pass through the xiphoid process twice, and was pinched and fixed. This further allowed the surgical field surrounding the liver to be kept open.

The cell sheet was transplanted in Groups 2 and 3. With regard to the cell sheet, after the medium was changed to serum-free DMEM in the cultureware, the medium was completely removed. Then, a Cell Shifter (CellSeed Inc.), which is a support for collecting a cell sheet, was placed on the cell sheet. This cell sheet, together with the support, was collected using forceps, etc. Then, the cell sheet having attached thereon the support was placed on the surface of the left lateral lobe of the liver. The operator waited about 3 to 5 min for adhesion of the cell sheet, and confirmed that the cell sheet was attached on the surface of the liver of the mouse. Thereafter, forceps were used to remove only the support.

Subsequently, the second cell sheet was transplanted on the first cell sheet, which had already been transplanted, in a manner similar to that of the first cell sheet. Next, the third cell sheet was transplanted on the second cell sheet, which had already been transplanted, in a manner similar to that of the first cell sheet. Meanwhile, the fourth cell sheet was transplanted on the surface of the right median lobe of the liver in a manner similar to that of the first cell sheet. Then, the fifth cell sheet was likewise transplanted on the fourth cell sheet, which had already been transplanted on the surface of the right median lobe. Furthermore, the sixth cell sheet was likewise transplanted on the fifth cell sheet, which had already been transplanted.

The suture that passed through the xiphoid process was removed; the forceps that fixed the peritoneum and the skin were taken out; and the peritoneum was closed with a suture. After that, the skin was closed with a surgical clip or a suture. Regarding Group 1 as a control, after the same operation as of the transplantation groups was applied to keep the surgical field open, the peritoneum and the skin were closed.

At the next day after the operation, 0.2 µl of carbon tetrachloride per 1 g of body weight of the mouse was diluted by 10 times with olive oil, and was given to all the mice including Groups 1 to 3 through a disposable oral probe, namely a stomach tube. Subsequently, whether or not the mice survived was daily checked from the day of the transplantation till 8 days after that. The body weight was measured once every other day. At days 2 and 4 after the cell sheet transplantation, the mice were put under inhalation anesthesia using isoflurane (Abbott Japan), and 100 to 200 µl of vein blood was drawn using a blood collecting capillary (HIRSCHMANN LABORGERATE) from the orbital plexus vein of the mice to collect the blood into a 1.5-ml tube. The collected vein blood stood still overnight on ice, and was then centrifuged in a cold centrifuge at 2,000 g and 4° C. for 20 min to separate serum. After that, only the serum was collected into a new 1.5-ml tube. Each necessary amount of the collected serum was dispensed into a 1.5-ml tube, and the tubes were stored in a deep freezer at −80° C. until their use.

At day 8 after the cell sheet transplantation, all the mice were put under inhalation anesthesia using isoflurane (Abbott Japan). Then, operating scissors or a similar surgical instrument, and forceps were used to perform laparotomy. After that, a 27-G needle and a 1-ml syringe were used to draw all the blood from inferior vena cava. After the blood sampling, the whole liver was excised. The wet weight of the excised whole liver was measured, and its image was photographed with a digital camera.

Of the tissue pieces containing the transplanted cell sheet, those for RNA extraction were cut into small pieces at a wet weight of 0.1 g by means of operating scissors or a similar surgical instrument. Next, 1 ml of TRIzol (Invitrogen) was added thereto. Then, a POLYTRON (KINEMATICA AG) was used for homogenization, and the samples were stored at a freezer at −30° C. until they were used in experiments. Tissue pieces for protein extraction were likewise cut into small pieces at a wet weight of 0.1 g by means of operating scissors or a similar surgical instrument. The samples were put into a 15-ml tube, subsequently immersed in liquid nitrogen, instantaneously frozen, and stored in a deep freezer at −80° C. until they were used in experiments.

Tissue pieces for histochemical staining were fixed with 4% paraformaldehyde (Nacalai Tesque). The post-fixed tissues were embedded in paraffin, and their tissue sections were then prepared with a microtome and stained with hematoxylin and eosin. Tissue sections other than those were stored at room temperature until immunohistochemical staining was carried out. Serum of the vein blood collected from inferior vena cava was separated using the same procedure as described above, and was stored in a deep freezer at −80° C.

The levels of serum transaminases of the mice at days 2, 4, and 8 after the cell sheet transplantation were determined using a Transaminase CII-Test Wako kit (Wako Pure Chemical Industries, Ltd.). The procedure was performed according to the attached protocol except that a reaction scale was reduced to one-quarter of the scale described in the package insert. The absorbance was read at 555 nm by using a microplate reader (Sunrise Absorbance Reader; Tecan Group Ltd.). According to a standard curve, the resulting absorbance was used to calculate an activity value (Karmen unit) and an international unit of each of aspartate aminotransferase (AST) and alanine aminotransferase (ALT).

Figure 36:
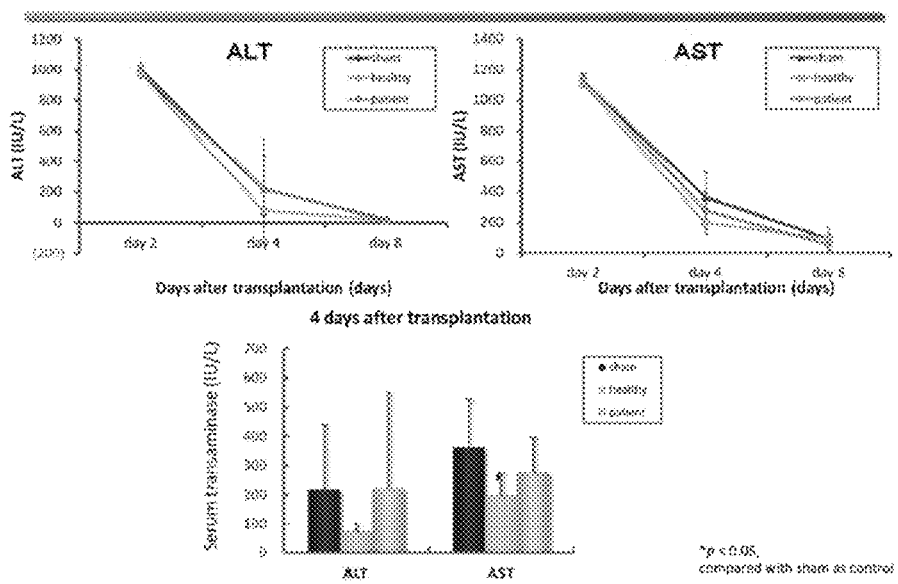
FIG. 36 is graphs illustrating how liver functions changed when a "healthy" or "patient"-derived cell sheet was transplanted on a liver surface.

FIG. 36 shows the above results. Transplantation of the cell sheet prepared from the differentiated healthy cells resulted in decreased levels of the ALT and AST values. In addition, transplantation of the cell sheet prepared from the differentiated patient cells resulted in decreased levels of the AST value.

Example 16

Figure 37:
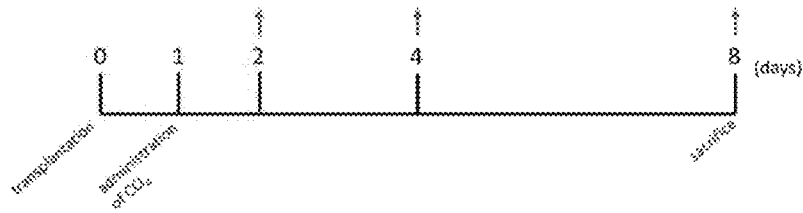
FIG. 37 illustrates how to conduct an experiment for suppression of liver dysfunction when six cell sheets were transplanted on a liver surface or when cells were transplanted via a portal vein by injection into a spleen.

Preparation of Cell Sheet and Transplantation on Liver Surface 9-week-old male NOD-SCID mice were divided into five groups (FIG. 37). Group 1 was a sham operation group in which no cell sheet was transplanted. Group 2 was a group in which six cell sheets were transplanted on the surface of the left lateral lobe of the liver. Group 3 was a group in which a phosphate-buffered saline (PBS) was administered via a portal vein by injection into the spleen. Group 4 was a group in which $1\times10^6$ cells were transplanted via a portal vein by injection into the spleen. Group 5 was a group in which $4\times10^7$ cells were transplanted via a portal vein by injection into the spleen.

The cell sheets were prepared according to the following procedure. At 8 days before the cell sheet transplantation, a human bone marrow-derived mesenchymal stem cell line (UE7T-13 cells) was seeded on a 6-cm dish (CellSeed Inc.), which is an UpCell temperature-responsive cell cultureware for collecting a cell sheet, at a cell density of $9.0\times10^3$ cells/cm$^2$, and was cultured under conditions at 37° C. and 5% $CO_2$ in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 μg/ml streptomycin (Nacalai Tesque). This time point was set to day 0.

At the next day corresponding to day 1, the medium was changed to DMEM containing hexachlorophene at a final concentration of 0.8 μM. Similar to day 1, the medium was changed at day 4. At the day of the cell sheet transplantation, the attached cells of periphery of the bottom of the dish was scraped with the tip of a disposable tip, etc., and the medium was changed with a medium at room temperature. Then, the cells were incubated under conditions at 20° C. and 5% $CO_2$ for 20 min or longer to produce a cell sheet. Until its transplantation, the cell sheet was kept under conditions at 20° C. and 5% $CO_2$.

Cells for cell transplantation via a portal vein by injection into the spleen were prepared according to the following procedure. A human bone marrow-derived mesenchymal stem cell line (UE7T-13 cells) was seeded on a 10-cm cell culture dish (TPP Techno Plastic Products AG) at a cell density of $9.0\times10^3$ cells/cm$^2$, and was cultured under conditions at 37° C. and 5% $CO_2$ in Dulbecco's Modified Eagle's Medium (DMEM; NISSUI PHARMACEUTICAL CO., LTD.) containing 10% fetal bovine serum (FBS; JRH Biosciences, INC.), 100 U/ml penicillin, and 100 μg/ml streptomycin (Nacalai Tesque). This time point was set to day 0.

At the next day corresponding to day 1, the medium was changed to DMEM containing hexachlorophene at a final concentration of 0.8 μM. Similar to day 1, the medium was changed at day 4. The cells were detached using trypsin treatment immediately before the cell transplantation. The number of Group 4 cells was adjusted with 100 μl of PBS at $1\times10^6$ cells, and the number of Group 5 cells was $4\times10^7$ cells.

First, on the day of transplantation, 1 μl of somnopentyl (Kyoritsuseiyaku Corporation), a systemic anesthetic, per 1 g of body weight of the NOD-SCID mouse was intraperitoneally administered to put the mouse under anesthesia. After the introduction of anesthesia, the abdomen of the Group 2 mouse was shaved, and operating scissors or a similar surgical instrument was used to cut the abdominal skin along the midline. Next, the peritoneum was dissected along the midline by using the operating scissors or the similar surgical instrument. Then, forceps, etc., were used to hold the skin and the peritoneum to keep the surgical field open in the peritoneum. A suture was made to pass through the xiphoid process twice, and was pinched and fixed. This further allowed the surgical field surrounding the liver to be kept open.

With regard to the cell sheet, after the medium was changed to serum-free DMEM in the cultureware, the medium was completely removed. Then, a Cell Shifter (CellSeed Inc.), which is a support for collecting a cell sheet, was placed on the cell sheet. This cell sheet, together with the support, was collected using forceps, etc. Then, the cell sheet having attached thereon the support was placed on the surface of the left lateral lobe of the liver. The operator waited about 3 to 5 min for adhesion of the cell sheet, and confirmed that the cell sheet was attached on the surface of the liver of the mouse. Thereafter, forceps, etc., were used to remove only the support. Subsequently, the second cell sheet was likewise transplanted and overlaid on the first cell sheet that had already been transplanted. After their adhesion, the third cell sheet was transplanted on the two cell sheets that had already been transplanted. The suture that passed through the xiphoid process was removed; the forceps, etc., that fixed the peritoneum and the skin were taken out; and the peritoneum was closed with a suture. Finally, the skin was closed with a surgical clip or a suture.

Regarding Group 1 as a control for a cell sheet transplantation operation, after the same operation as of the transplantation groups was applied to keep the surgical field open, the peritoneum and the skin were closed. After anesthesia, the left abdomen of Groups 4 and 5 was shaved. Next, operating scissors or a similar surgical instrument was used to cut about 1 cm of the skin of the left abdomen at a middle position between the sternum and the femur in a direction perpendicular to the midline. Then, the peritoneum was likewise cut. After that, forceps were used to take fat directly under the spleen out. Finally, about two-third of the spleen was exposed outside the body. With regard to Group 4, a 1-ml syringe with a 24-G needle was filled with $1 \times 10^6$ cells suspended in 100 µl of PBS, and the cells were injected into the spleen. After the needle was withdrawn from the spleen, the spleen was quickly ligated with a suture. Then, the bleeding was stopped and the spleen was returned to the original position. After that, the peritoneum and the skin were closed with sutures. With regard to Group 5, $4 \times 10^7$ cells were likewise injected into the spleen. Regarding Group 3, which was a control for transplantation operations of Groups 4 and 5, the spleen was exposed in substantially the same manner as in Groups 4 and 5. Then, a 1-ml syringe with a 24-G needle was filled with 100 µl of PBS and the PBS was injected into the spleen. After that, the peritoneum and the skin were closed in the same manner as in Groups 4 and 5. Thereafter, the mice were fed under normal conditions until the day of sacrifice.

At the next day after the operation, 0.2 µl of carbon tetrachloride per 1 g of body weight of the mouse was diluted by 10 times with olive oil, and was given to all the mice including Groups 1 to 5 through a disposable oral probe, namely a stomach tube. Subsequently, whether or not the mice survived was daily checked from the day of the transplantation till 8 days after that. At days 2 and 4 after the cell sheet transplantation, the mice were put under inhalation anesthesia using isoflurane (Abbott Japan), and 100 to 200 µl of vein blood was drawn using a blood collecting capillary (HIRSCHMANN LABORGERATE) from the orbital plexus vein of the mice to collect the blood into a 1.5-ml tube. The collected vein blood stood still overnight on ice, and was then centrifuged in a cold centrifuge at 2,000 g and 4° C. for 20 min to separate serum. After that, only the serum was collected into a new 1.5-ml tube. Each necessary amount of the collected serum was dispensed into a 1.5-ml tube, and the tubes were stored in a deep freezer at −80° C. until their use. At day 8 after the cell sheet transplantation, all the mice were put under inhalation anesthesia using isoflurane (Abbott Japan). Then, operating scissors or a similar surgical instrument, and forceps were used to perform laparotomy. After that, a 27-G needle and a 1-ml syringe were used to draw all the blood from inferior vena cava. Serum of the vein blood collected from inferior vena cava was separated using the same procedure as described above, and was stored in a deep freezer at −80° C.

Figure 38:
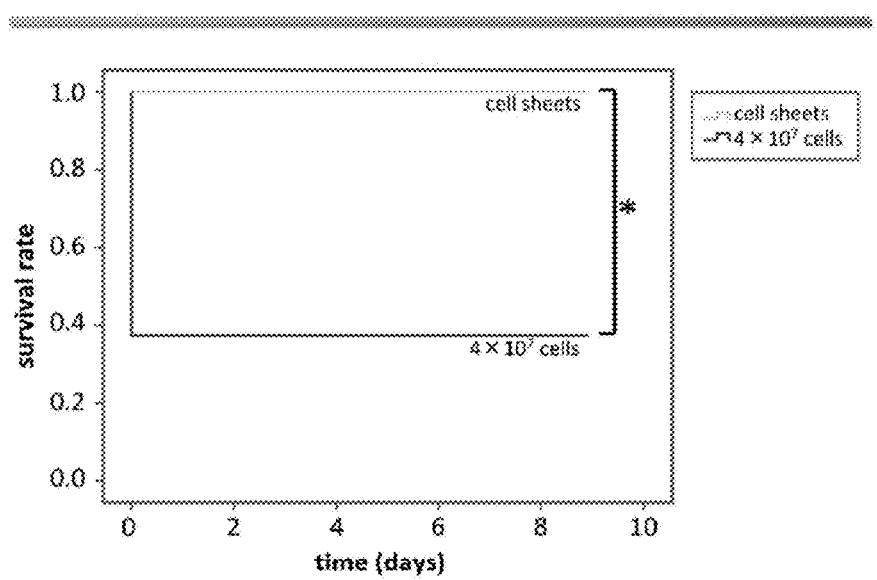
FIG. 38 is a graph illustrating the results of examining survival rates of mice.

The number of surviving mice was counted each day after the transplantation according to the above procedure. Based on the number, a survival curve was drawn using PASW statistical software according to a Kaplan-Meier method. The survival rate was tested by a logrank test. FIG. 38 shows the results. Group 2 that was transplanted with a total of 6 cell sheets on the liver surface was found to have a significantly improved survival rate when compared with Group 5 that was transplanted via a portal vein with $4 \times 10^7$ cells, which was an equivalent number, by injection into the spleen. With regard to Group 5, 5 out of 8 mice died within one day after the transplantation. Cell clogging seemed to be the cause. This demonstrated that when a large number of cells were transplanted, the transplantation of the cell sheet on the liver surface was much safer.

The levels of serum transaminases of the mice at days 2, 4, and 8 after the cell sheet transplantation were determined using a Transaminase CII-Test Wako kit (Wako Pure Chemical Industries, Ltd.). The procedure was performed according to the attached protocol except that a reaction scale was reduced to one-quarter of the scale described in the package insert. The absorbance was read at 555 nm by using a microplate reader (Sunrise Absorbance Reader; Tecan Group Ltd.). According to a standard curve, the resulting absorbance was used to calculate an activity value (Karmen unit) and an international unit of each of aspartate aminotransferase (AST) and alanine aminotransferase (ALT). The levels of serum bilirubin of the mice at days 2, 4, and 8 after the cell sheet transplantation were determined using a QuantiChrom Bilirubin Assay kit (BioAssaySystems). According to the protocol attached to the kit, the absorbance was read at 530 nm by using a microplate reader (Sunrise Absorbance Reader; Tecan Group Ltd.). According to a standard curve, the levels of total bilirubin were calculated. With regard to the transferase values and bilirubin value, a ratio of the transferase or bilirubin level of interest to that of the corresponding operation control group at each data point was calculated. Specifically, a ratio of the level of Group 2 to that of Group 1 and a ratio of the level of Group 4 or 5 to that of Group 3 was calculated.

Figure 39:
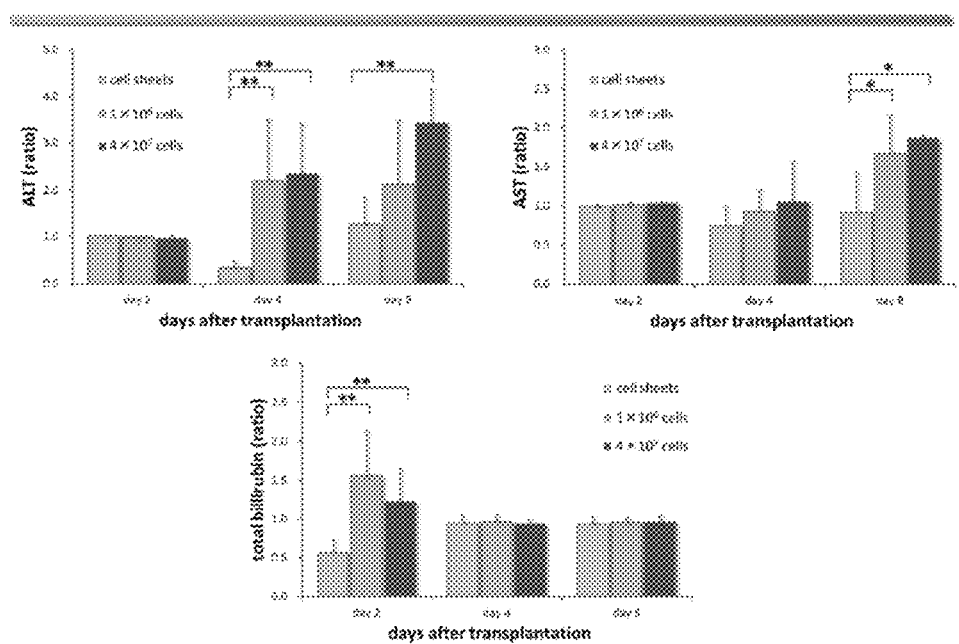
FIG. 39 is graphs illustrating the results of how liver functions changed.

FIG. 39 shows the results. A ratio of the transferase level of each transplantation group to that of the corresponding operation control group was calculated. Group 2, a sheet transplantation group, was found to have significantly decreased levels of the transferases ALT and AST after day 4, compared with Groups 4 and 5 in which the cells had been transplanted via a portal vein by injection into the spleen. Next, a ratio of the bilirubin level of each transplantation group to that of the corresponding operation control group was calculated. Group 2, a sheet transplantation group, was found to have significantly decreased levels of bilirubin at day 2, compared with Groups 4 and 5 in which the cells had been transplanted via a portal vein by injection into the spleen. This demonstrated that transplantation of the cell sheet as prepared in this Example on a liver surface exerted a higher therapeutic effect than transplantation of cells via a portal vein, one of methods selected from conventional cell transplantation methods.

<Discussion of Results>

In view of the above experimental results, the present inventors have elucidated that IC-2, etc., can inhibit the Wnt/β-catenin signaling pathway. In addition, they have revealed that IC-2, etc., can be used to induce differentiation of mesenchymal stem cells into functional hepatocytes.

Also, they have shown that a cell sheet as prepared using IC-2, etc., can be used to suppress liver dysfunction. Further, this cell sheet has a remarkable effect of suppressing the liver dysfunction when transplanted on a liver surface. Furthermore, they have demonstrated that functional hepatocytes can be differentiated from cells prepared and separated from bone marrow of an actual patient; a cell sheet can be prepared using these functional hepatocytes; and this cell sheet can be used to suppress liver dysfunction. Moreover, they have discovered that this cell sheet has a higher therapeutic effect of suppressing liver dysfunction than a method for cell transplantation via a portal vein. These findings are important so as to develop genuinely clinically applicable liver regenerative medicine.

Hereinabove, the present invention has been described based on the Examples. These Examples are absolutely examples. It should be understood by those skilled in the art that various modifications are allowed, and those modifications are also within the scope of the present invention.

The invention claimed is:

1. A compound, a salt thereof, or a solvate of the compound or of the salt thereof, the compound being selected from the group consisting of compounds represented by formulae (1) and (2):

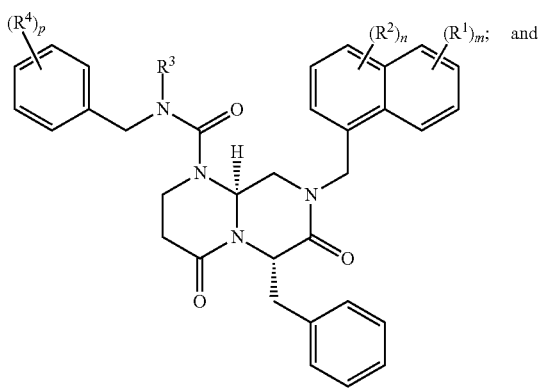

(1)

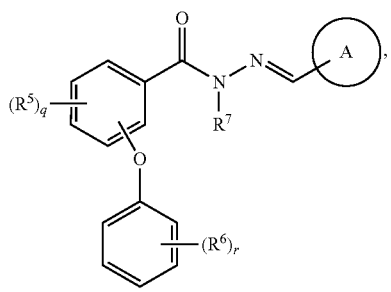

(2)

wherein $R^1$, $R^2$, and $R^4$ are the same or different from each other and each represents H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl;

$R^3$ represents H, optionally substituted $C_{1-6}$ alkyl, or optionally substituted $C_{2-6}$ alkenyl;

$R^5$ and $R^6$ are the same or different from each other and each represents H, halogen, nitro, cyano, OH, $C_{1-6}$ alkyl, halogeno $C_{1-6}$ alkyl, hydroxy $C_{1-6}$ alkyl, $C_{1-6}$ alkyl amino, $C_{1-6}$ alkoxy, halogeno $C_{1-6}$ alkoxy, hydroxy $C_{1-6}$ alkoxy, or $C_{1-6}$ alkoxy amino;

$R^7$ represents H;

ring A is naphthyl, phenyl substituted with five halogens, or furyl substituted with one methyl;

m and q are integers of any of 1 to 4;

n is an integer of any of 1 to 3; and p and r are integers of any of 1 to 5, with the proviso that N-[(5-methyl-2-furyl)methylideneamino]-2-phenoxy-benzamide is excluded.

2. The compound, the salt thereof, or the solvate of the compound or of the salt thereof according to claim 1, wherein $R^1$, $R^2$, and $R^4$ are the same or different from each other and each represents H, halogen, nitro, cyano, OH, $C_{1-6}$ alkyl, halogeno $C_{1-6}$ alkyl, hydroxy $C_{1-6}$ alkyl, $C_{1-6}$ alkyl amino, $C_{1-6}$ alkoxy, halogeno $C_{1-6}$ alkoxy, hydroxy $C_{1-6}$ alkoxy, or $C_{1-6}$ alkoxy amino; and $R^3$ represents H.

3. The compound, the salt thereof, or the solvate of the compound or of the salt thereof according to claim 2, wherein the at least one compound, the salt thereof, or the solvate of the compound or of the salt thereof is selected from the group consisting of compounds represented by formulae (3) to (5):

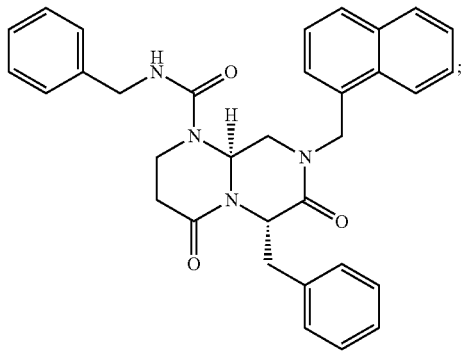

(3)

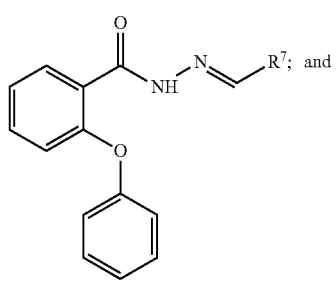

(4)

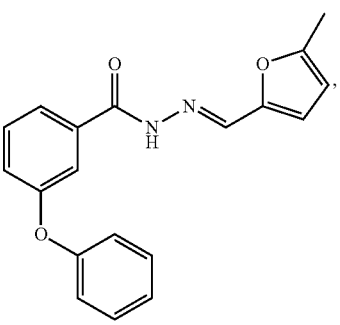

(5)

wherein $R^7$ is naphthyl or phenyl substituted with five halogens.

4. The compound, the salt thereof, or the solvate of the compound or of the salt thereof according to claim 3, wherein the at least one compound, the salt thereof, or the solvate of the compound or of the salt thereof is selected from the group consisting of compounds represented by formulae (3), (5), (6), and (7):

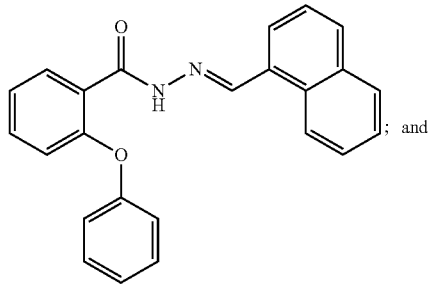
(6)
; and

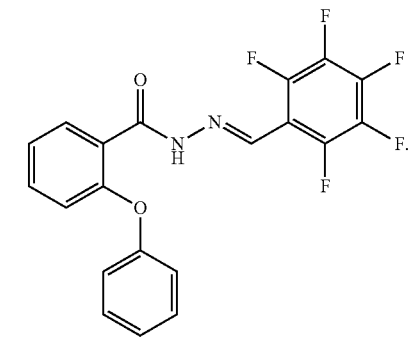
(7)

5. A method for producing a hepatocyte from a mesenchymal stem cell, comprising a step of contacting mesenchymal stem cell with an effective amount of a compound, a salt thereof, or a solvate thereof of a compound according to claim 1 to obtain the hepatocyte.

6. The method for producing the hepatocyte from the mesenchymal stem cell according to claim 5, comprising a step of contacting the mesenchymal stem cell with an effective amount of at least one compound, a salt thereof, or a solvate thereof of, the at least one compound being selected from the group consisting of compounds represented by formulae (3), (5), (6), and (7):

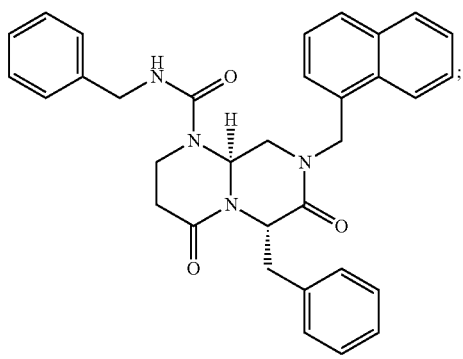
(3)

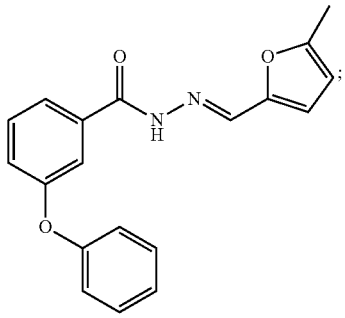
(5)

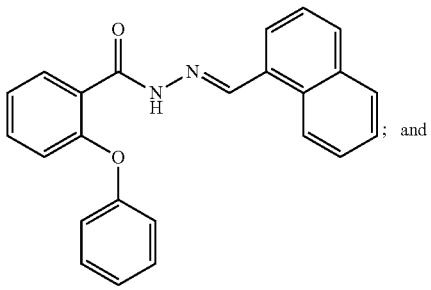
(6)
; and

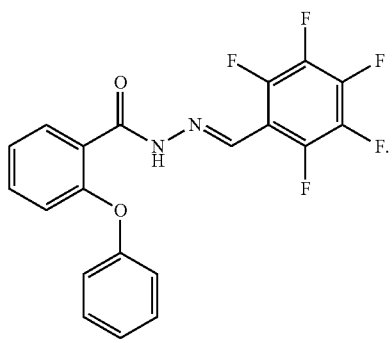
(7)

7. The method for producing the hepatocyte from the mesenchymal stem cell according to claim 5, wherein the mesenchymal stem cell is a bone marrow-derived cell.

8. A method for inhibiting the Wnt/β-catenin signaling pathway of a mesenchymal stem cell, comprising a step of contacting a mesenchymal stem cell with a compound, a salt thereof, or a solvate thereof of compound according to claim 1, which results in inhibition of the Wnt/β-catenin signaling pathway in the mesenchymal stem cell.

9. The method for inhibiting the Wnt/p-catenin signaling pathway of a mesenchymal stem cell according to claim 8, wherein the compound is selected from the group consisting of compounds represented by formulae (3), (5), (6), and (7):

(3)

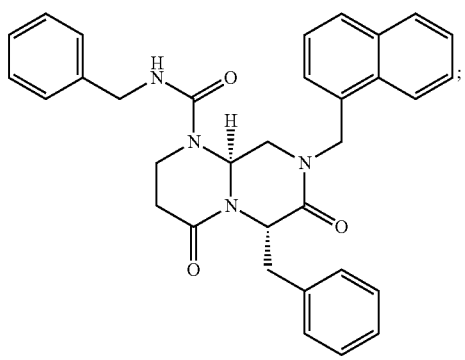

(5)

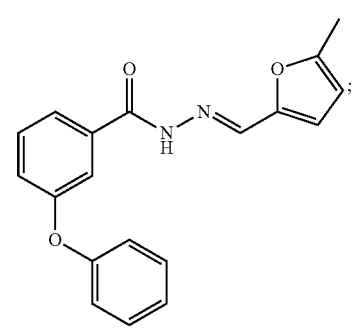

(6)

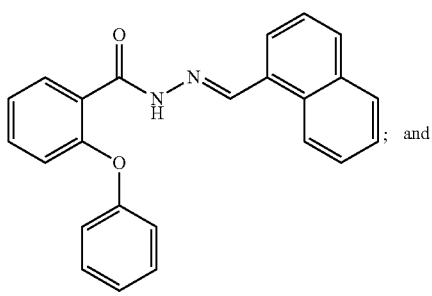
; and (7)

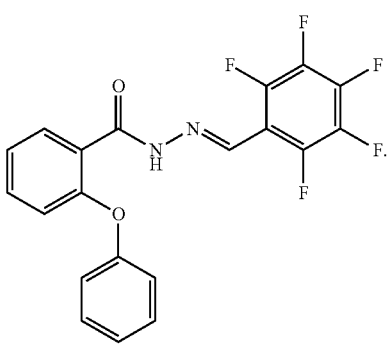

or a salt thereof, or a solvate thereof.

10. The method for producing a hepatocyte from the mesenchymal stem cell according to claim 8, wherein the mesenchymal stem cell is a bone marrow-derived cell.

11. A method for producing a transplantation material comprising contacting a mesenchymal stem cell with the compound, the salt thereof, or the solvate of the compound or of the salt thereof according to claim 1.

12. The production method according to claim 11, comprising culturing the mesenchymal stem cell in a medium comprising the compound, the salt thereof, or the solvate of the compound or of the salt thereof according to claim 1 to differentiate the mesenchymal stem cell into a hepatocyte.

13. The production method according to claim 12, wherein the transplantation material is a cell sheet.

* * * * *

SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ttggaaaaat cccactgcat                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctccaagctg ctcaaaaagc                                                    20

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
gtcttctcca ccatggagaa ggct                                               24

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
catgccagtg agcttcccgt tca                                                23

<210> SEQ ID NO 5
<211> LENGTH: 28
<212> TYPE: DNA

```
<213> ORGANISM: Artificial Sequence
<220> FEATURE:
<223> OTHER INFORMATION: Primer

<400> SEQUENCE: 5
caaggagctt gacagagaca cagttttt                                            28

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
gtgtccttga cttcaaaggg tctct                                               25

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
cgacttggga ttatgcctct gacc                                                24

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
cccaattcta tctgggccat tttga                                               25

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
aaggcacttg gcatctcccc a                                                   21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cagggcggca atggtgtagc                                                     20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gtccttcccc aggagccgac                                                     20
```

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtctccaccg cttgctccac                                              20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gcttcaagcc catccgcaca                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tgacaggact ggctgctgct                                              20

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
cagcaccatg ggacccacct cag                                          23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
ctctccagcc gcaagatgtt ggg                                          23

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
actttgagac cgaggggccc                                              20

<210> SEQ ID NO 18
<211> LENGTH: 20
<212> TYPE: DNA
<213> ORGANISM: Artificial Sequence
<220> FEATURE:

<223> OTHER INFORMATION: Primer

<400> SEQUENCE: 18
ggcacttcct gcacagcctc                                          20

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
cccagaagcg cagaagatt                                           19

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
aaggtttctt tctgatctgc cat                                      23

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
cttgtggcca actggctc                                            18

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
gcttcagcaa gttggcga                                            18

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ttccagaggc aagaccaacc                                          20

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
tgcctgagtc cactgcaaa                                           19

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
aggattctca ttcgttgacc ac                                          22

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tctgacactc ggttgtaggt                                             20

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
aaagttagaa tctgatgtct cagctcaa                                    28

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
ctttcctgat aatttcctca cattcttt                                    28

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
agccacatcg ctcagacac                                              19

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
gcccaatacg accaaatcc                                              19

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
ccagagctgt gcagatgag                                                    19

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
gtcagcaggc tggcattt                                                     18

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
cagctggagg cagttaacat                                                   20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
cgccttcgtc aggcatattg                                                   20

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
cccttcaata gcatgtcaag tgg                                               23

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
gttcccttgt agctgcgt                                                     18

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
ttgccttgct gctctacct                                                    19

<210> SEQ ID NO 38
<211> LENGTH: 22

```
<212> TYPE: DNA
<213> ORGANISM: Artificial Sequence
<220> FEATURE:
<223> OTHER INFORMATION: Primer

<400> SEQUENCE: 38
tccatgaact tcaccacttc gt                                          22

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
ctgaagggaa gaaccgcttg                                             20

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
agcctttctt tattgatctg ccaca                                       25

<210> SEQ ID NO 41
<211> LENGTH: 16
<212> TYPE: DNA
<213> ORGANISM: Artificial Sequence
<220> FEATURE:
<223> OTHER INFORMATION: Primer

<400> SEQUENCE: 41
ctgcgtctgc tgaggc                                                 16

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
tccacggctc aaccactg                                               18

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
tgggtcaagg caagagagag ta                                          22

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
```

-continued gattccttcc tgttgatttg acca                                          24

<210> SEQ ID NO 45
<211> LENGTH: 17
<212> TYPE: DNA
<213> ORGANISM: Artificial Sequence
<220> FEATURE:
<223> OTHER INFORMATION: Primer

<400> SEQUENCE: 45
gggtccggga gaagagc                                                  17

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
gccaggtaac ggttagcac                                                19

<210> SEQ ID NO 47
<211> LENGTH: 16
<212> TYPE: DNA
<213> ORGANISM: Artificial Sequence
<220> FEATURE:
<223> OTHER INFORMATION: Primer

<400> SEQUENCE: 47
ggaccggaaa gtccgt                                                   16

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
gctcctcctt gtttggtgt                                                19

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
aacgaaagaa acttcgacaa gaga                                          24

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
atgatccact ggaaagagga cc                                            22

<210> SEQ ID NO 51
<211> LENGTH: 17
<212> TYPE: DNA
<213> ORGANISM: Artificial Sequence
<220> FEATURE:
<223> OTHER INFORMATION: Primer

<400> SEQUENCE: 51
agggacagtg gagaggg                                                17

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
gcaagtgaga atccaagttt gtgt                                        24

<210> SEQ ID NO 53
<211> LENGTH: 17
<212> TYPE: DNA
<213> ORGANISM: Artificial Sequence
<220> FEATURE:
<223> OTHER INFORMATION: Primer

<400> SEQUENCE: 53
ttccattgtc ctgcccg                                                17

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
aagtgtgtgt acctggagtt atc                                         23

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
atgtgcaaat gtgccctca                                              19

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
tcgcttctga cattgcgct                                              19

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
cccagggacc tctctctaat c                                           21

<210> SEQ ID NO 58
<211> LENGTH: 16
<212> TYPE: DNA
<213> ORGANISM: Artificial Sequence
<220> FEATURE:
<223> OTHER INFORMATION: Primer

<400> SEQUENCE: 58
ggccaggagg gcattg                                                      16

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gttggtggac ccgctcagta                                                  20

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
aacagacgta agaaccagag gtag                                             24

<210> SEQ ID NO 61
<211> LENGTH: 16
<212> TYPE: DNA
<213> ORGANISM: Artificial Sequence
<220> FEATURE:
<223> OTHER INFORMATION: Primer

<400> SEQUENCE: 61
ggcagcagcg gcaatg                                                      16

<210> SEQ ID NO 62
<211> LENGTH: 18
<212> TYPE: DNA
<213> ORGANISM: Artificial Sequence
<220> FEATURE:
<223> OTHER INFORMATION: Primer

<400> SEQUENCE: 62
ccaccttggc ccggatca                                                    18

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
agccacatcg ctcagacac                                                   19

<210> SEQ ID NO 64
<211> LENGTH: 19
<212> TYPE: DNA

```
<213> ORGANISM: Artificial Sequence
<220> FEATURE:
<223> OTHER INFORMATION: Primer

<400> SEQUENCE: 64
gcccaatacg accaaatcc                                                19
```